United States Patent
Santella et al.

(10) Patent No.: US 8,536,198 B2
(45) Date of Patent: Sep. 17, 2013

(54) PIPERIDINE DERIVATIVES AS MODULATORS OF CHEMOKINE RECEPTOR ACTIVITY

(75) Inventors: Joseph B. Santella, Springfield, PA (US); John Hynes, Washington Crossing, PA (US); Daniel S. Gardner, Furlong, PA (US)

(73) Assignee: Bristol-Myers Squibb Company, Priceton, NJ (US)

(*) Notice: Subject to any disclaimer, the term of this patent is extended or adjusted under 35 U.S.C. 154(b) by 732 days.

(21) Appl. No.: 12/670,025

(22) PCT Filed: Jul. 23, 2008

(86) PCT No.: PCT/US2008/070804
§ 371 (c)(1),
(2), (4) Date: Jan. 21, 2010

(87) PCT Pub. No.: WO2009/015166
PCT Pub. Date: Jan. 29, 2009

(65) Prior Publication Data
US 2010/0222366 A1    Sep. 2, 2010

Related U.S. Application Data

(60) Provisional application No. 60/951,478, filed on Jul. 24, 2007, provisional application No. 61/081,529, filed on Jul. 17, 2008.

(51) Int. Cl.
| | | |
|---|---|---|
| C07D 413/12 | (2006.01) | |
| C07D 405/06 | (2006.01) | |
| C07D 401/12 | (2006.01) | |
| C07D 211/52 | (2006.01) | |
| A61K 31/501 | (2006.01) | |
| A61K 31/497 | (2006.01) | |
| A61K 31/4545 | (2006.01) | |
| A61K 31/454 | (2006.01) | |
| A61K 31/451 | (2006.01) | |

(52) U.S. Cl.
USPC ...... 514/330; 514/318; 514/326; 514/255.05; 514/256; 514/321; 514/273; 514/274; 544/406; 544/335; 546/194; 546/210; 546/217; 546/198

(58) Field of Classification Search
USPC ............. 514/318, 326, 330, 255.05, 256, 514/321; 544/406, 335; 546/194, 210, 217, 546/198
See application file for complete search history.

(56) References Cited

U.S. PATENT DOCUMENTS

| | | |
|---|---|---|
| 6,489,354 B1 | 12/2002 | Bao et al. |
| 7,601,844 B2 | 10/2009 | Carter et al. |
| 7,615,556 B2 | 11/2009 | Carter et al. |
| 2006/0004018 A1 | 1/2006 | Xue et al. |
| 2007/0208056 A1* | 9/2007 | Carter et al. ............ 514/317 |

FOREIGN PATENT DOCUMENTS

| | | |
|---|---|---|
| WO | WO 03/105853 | 12/2003 |
| WO | WO 2006/004741 | 1/2006 |
| WO | WO 2007/092681 | 8/2007 |

* cited by examiner

*Primary Examiner* — Joseph Kosack
*Assistant Examiner* — Matthew Coughlin
(74) *Attorney, Agent, or Firm* — Terence J. Bogie

(57) ABSTRACT

The present application describes modulators of MIP-1 of formula (I): or stereoisomers or pharmaceutically acceptable salts thereof, wherein m, Q, T, W, Z, R1, R3, R4, R5, R5a and R5b, are as set forth above. In addition, methods of treating and preventing inflammatory diseases such as asthma and allergic diseases, as well as autoimmune pathologies such as rheumatoid arthritis and atherosclerosis using the modulators are disclosed.

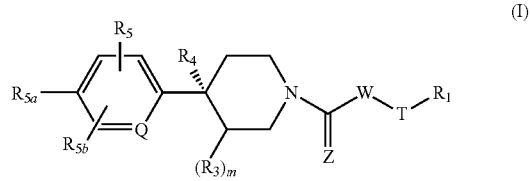

(I)

14 Claims, No Drawings

PIPERIDINE DERIVATIVES AS MODULATORS OF CHEMOKINE RECEPTOR ACTIVITY

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity* 2000, 12, 121): CCR-1 (or "CKR-1" or "CC-CKR-1") [MIP-1α, MCP-3, MCP-4, RANTES] (Ben-Barruch et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson et al., *Biochemistry* 1996, 35, 3362-3367); CCR-6 (or "CKR-6" or "CC-CKR-6") [LARC] (Baba et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [1-309] (Napolitano et al., *J. Immunol.* 1996, 157, 2759-2763); CCR-10 (or "CKR-10" or "CC-CKR-10") [MCP-1, MCP-3] (Bonini et al., *DNA and Cell Biol.* 1997, 16, 1249-1256); and CCR-11 [MCP-1, MCP-2, and MCP-4] (Schweickart et al., *J. Biol. Chem.* 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., *Current Opinion in Chemical Biology* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

Demonstration of the importance of the MIP-1α/CCR-1 interaction has been provided by experiments with genetically modified mice. MIP-1α–/– mice had normal numbers of leukocytes, but were unable to recruit monocytes into sites of viral inflammation after immune challenge (Cook, D. et al., *Science* 1995, 269, 1583-1585). Recently, MIP-1α–/– mice were shown to be resistant to collagen antibody induced arthritis (Chintalacharuvu, S. R., *Immun. Lett.* 2005, 202-204). Likewise, CCR-1–/– mice were unable to recruit neutrophils when challenged with MIP-1α in vivo; moreover, the peripheral blood neutrophils of CCR-1 null mice did not migrate in response to MIP-1α (Gao, B. et al., *J. Exp. Med.* 1997, 185, 1959-1968), thereby demonstrating the specificity of the MIP-1α/CCR-1 interaction. The viability and generally normal health of the MIP-1α–/– and CCR-1–/– animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis (Koch, A. et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. et al., *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It should also be noted that CCR-1 is also the receptor for the chemokines RANTES, MCP-3, HCC-1, Lkn-1/HCC-2, HCC-4, and MPIF-1 (Carter, P. H., *Curr. Opin Chem. Bio.* 2002, 6, 510-525). Since it is presumed that the new compounds of formula (I) described herein antagonize MIP-1α by binding to the CCR-1 receptor, it may be that these compounds of formula (I) are also effective antagonists of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

For example, demonstration of the chemotactic properties of RANTES in humans has been provided experimentally. Human subjects, when injected intradermally with RANTES, experienced an influx of eosinophils to the site of injection (Beck, L. A. et al., *J. Immun.* 1997, 159, 2962-2972). Likewise, a RANTES antibody has demonstrated the ability to ameliorate the symptoms of disease in the rat Adjuvant induced arthritis (AIA) model (Barnes, D. A. et al., *J. Clin Invest.* 1998, 101, 2910-2919). Similar results were obtained when using a peptide derived antagonist of the RANTES/CCR-1 interaction in both the rat AIA (Shahrara, S. et al., *Arthritis & Rheum.* 2005, 52, 1907-1919) and the mouse CIA (Plater-Zyberk, C. et al., *Imm. Lett.* 1997, 57, 117-120) disease models of joint inflammation.

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides novel antagonists or partial agonists/antagonists of MIP-1α or CCR-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

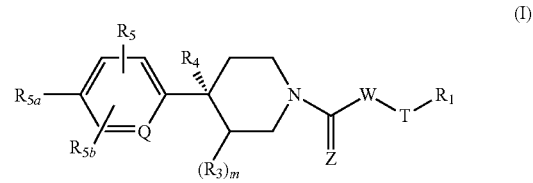

or stereoisomers or prodrugs or pharmaceutically acceptable salts thereof, wherein m, Q, T, W, Z, $R_1$, $R_3$, $R_4$, $R_5$, $R_{5a}$ and $R_{5b}$, are defined below, are effective modulators of MIP-1α and chemokine activity.

DETAILED DESCRIPTION OF THE PRESENT INVENTION

In one embodiment, the present invention provides novel compounds of formula (I):

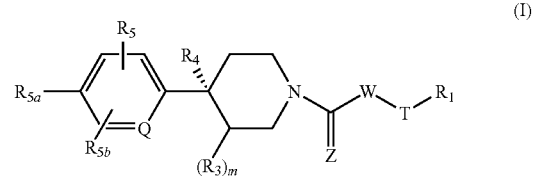

or a stereoisomer or pharmaceutically acceptable salt from thereof, wherein:

Q is CH or N;
Z is O or S;
W is

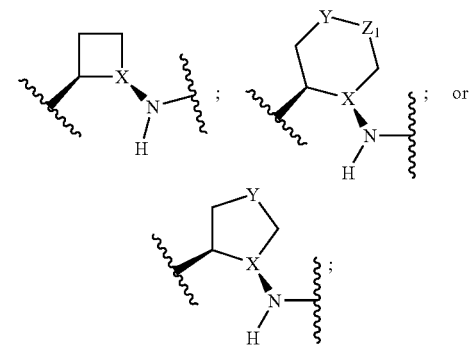

X is $C(R_8)$;
Y is $CH(R_{1a})$, $CH_2$, O, S, S(O), $S(O)_2$, $N(R_8)$, C(=O) or

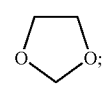

$Z_1$ is $CH(R_7)$, $CH_2$, O, S, $N(R_8)$, S(O) or $S(O)_2$;

T is a bond,

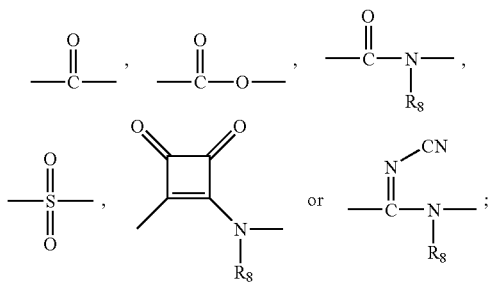

$R_1$ is alkyl, cycloalkyl, aryl, heterocyclyl or heteroaryl, all of which may be optionally substituted with 0-5 $R_{1a}$; provided that $R_1$ is not unsubstituted phenyl when T is

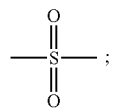

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O$(CR_8R_8)_rR_{10}$, —O(CF$_2)_r$CF$_3$, —O$(CR_8R_8)_rR_{10}$, —OH, —SH, —S$(CR_8R_8)_rR_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2)_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2)_r$CF$_3$, —C(=O)(CR$_8$R$_8)_r$R$_{10}$, —NR$_9$C(=O)H, —NR$_9$C(=O)(CR$_8$R$_8)_r$R$_{10}$, —OC(=O)(CR$_8$R$_8)_r$R$_{10}$, —C(=NR$_{14}$)NR$_9$R$_9$, —NHC(=NR$_{14}$)NR$_{14}$R$_{14}$, —S(=O)(CR$_8$R$_8)_r$R$_{10}$, —S(O)$_2$(CR$_8$R$_8)_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8)_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2)_r$CF$_3$, —C(=O)(CR$_8$R$_8)_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8)_r$R$_{10}$, —O(CF$_2)_r$CF$_3$, —O(CR$_8$R$_8)_r$R$_{10}$, —OH, —SH, —S(CR$_8$R$_8)_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2)_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2)_r$CF$_3$, —C(=O)(CR$_8$R$_8)_r$R$_{10}$, —NR$_9$C(=O)H, —NR$_9$C(=O)(CR$_8$R$_8)_r$R$_{10}$, —OC(=O)(CR$_8$R$_8)_r$R$_{10}$, —C(=NR$_{14}$)NR$_9$R$_9$, —NHC(=NR$_{14}$)NR$_{14}$R$_{14}$, —S(=O)(CR$_8$R$_8)_r$R$_{10}$, —S(O)$_2$(CR$_8$R$_8)_r$R$_{10}$, —NR$_9$C(=O)OR$_6$, —NR$_9$S(O$_2$)R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_4$ is hydrogen, F, OH, CN or —NH$_2$;

$R_5$ is hydrogen, halo, —CN or -Oalkyl;

$R_{5a}$ is hydrogen, halo, —CN or alkynyl;

$R_{5b}$ is hydrogen, halo, —CN or -Oalkyl;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8)_r$R$_{10}$, —O(CF$_2)_r$CF$_3$, —O(CR$_8$R$_8)_r$R$_{10}$, —OH, —SH, —S(CR$_8$R$_8)_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2)_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2)_r$CF$_3$, —C(=O)(CR$_8$R$_8)_r$R$_{10}$, —NR$_9$C(=O)H, —NR$_9$C(=O)(CR$_8$R$_8)_r$R$_{10}$, —OC(=O)(CR$_8$R$_8)_r$R$_{10}$, —S(=O)(CR$_8$R$_8)_r$R$_{10}$, —S(O)$_2$(CR$_8$R$_8)_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8)_r$R$_{10}$, —O(CF$_2)_r$CF$_3$, —O(CR$_8$R$_8)_r$R$_{10}$, —OH, —SH, —S(CR$_8$R$_8)_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2)_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2)_r$CF$_3$, —C(=O)(CR$_8$R$_8)_r$R$_{10}$, —NR$_9$C(=O)H, —NR$_9$C(=O)(CR$_8$R$_8)_r$R$_{10}$, —OC(=O)(CR$_8$R$_8)_r$R$_{10}$, —C(=NR$_{14}$)NR$_9$R$_9$, —NHC(=NR$_{14}$)NR$_{14}$R$_{14}$, —S(=O)(CR$_8$R$_8)_r$R$_{10}$, —S(O)$_2$(CR$_8$R$_8)_r$R$_{10}$, —NR$_9$C(=O)OR$_6$, —NR$_9$S(O$_2$)R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8)_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2)_r$CF$_3$, —C(=O)(CR$_8$R$_8)_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2;

r is 0-5;

provided that:

(1) $R^5$, $R^{5a}$ and $R^{5b}$ are not all H when T is a bond and $R^4$ is H or OH; and (2) $R^4$ is not piperidin-4-yl, pyridine-4-yl, or pyrimidin-4-yl, when T is a bond and $R^4$ is H.

In yet another embodiment, compounds of the present invention, or a stereoisomer or pharmaceutically acceptable salt from thereof, are those in which Q is CH.

In another embodiment, compounds of the present invention, or a stereoisomer or pharmaceutically acceptable salt from thereof, are those in which the compound is a compound of formula (Ia):

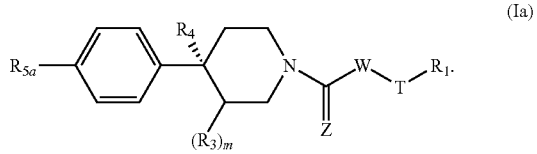

(Ia)

In yet another embodiment, compounds of the present invention, or a stereoisomer or pharmaceutically acceptable salt from thereof, are those in which:

Z is O or S;
W is

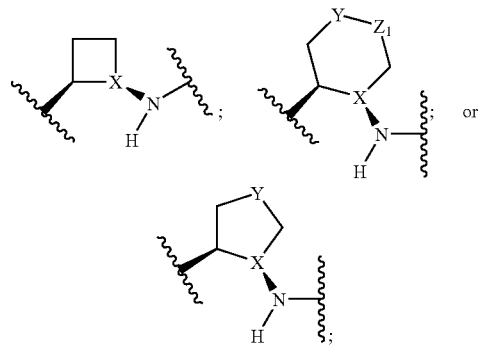

X is C(R$_8$);
Y is CH(R$_{1a}$), CH$_2$, O, S, S(O), S(O)$_2$, N(R$_8$), C(=O) or

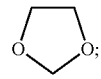

$Z_1$ is CH(R$_7$), CH$_2$, O, S, N(R$_8$), S(O) or S(O)$_2$;
T is

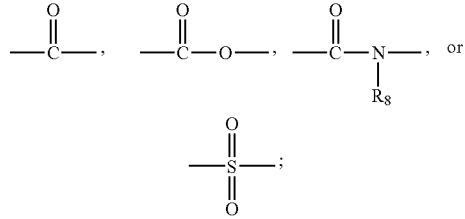

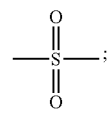

$R_1$ is alkyl, cycloalkyl, aryl, heterocyclyl or heteroaryl, all of which may be optionally substituted with 0-5 $R_{1a}$; provided that $R_1$ is not unsubstituted phenyl when T is

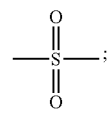

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_4$ is hydrogen, F, OH, CN or —NH$_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-4.

In still yet another embodiment, compounds of the present invention, or a stereoisomer or pharmaceutically acceptable salt from thereof, are those in which:

Z is O or S;
W is

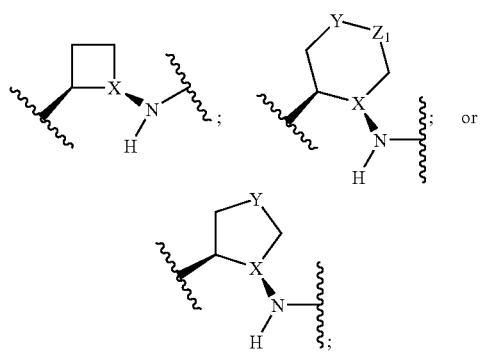

X is C(R$_8$);
Y is CH(R$_{1a}$), CH$_2$, O, S, S(O)$_2$, N(R$_8$), C(=O) or

Z$_1$ is CH(R$_7$), CH$_2$, O, S, N(R$_8$) or S(O)$_2$;
T is

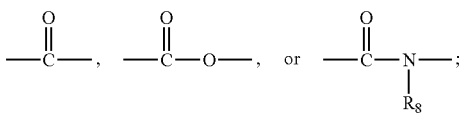

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is hydrogen, F, OH, CN or —NH$_2$;
R$_5$ is hydrogen, halo or —CN;
R$_{5a}$ is halo, —CN or alkynyl;
R$_{5b}$ is hydrogen, halo or —CN;
R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;
R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-3.

In one embodiment, compounds of the present invention, or a stereoisomer or pharmaceutically acceptable salt from thereof, are those in which:

Z is O;

W is

X is C(R$_8$);

Y is CH(R$_{1a}$), CH$_2$, O, S, S(O)$_2$, N(R$_8$) or C(=O);

Z$_1$ is CH(R$_7$), CH$_2$, O, S or N(R$_8$);

T is

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is hydrogen, F, OH, or —NH$_2$;

R$_5$ is hydrogen, halo or —CN;

R$_{5a}$ is halo, —CN or alkynyl;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt from thereof, are those in which:

Z is O;

W is

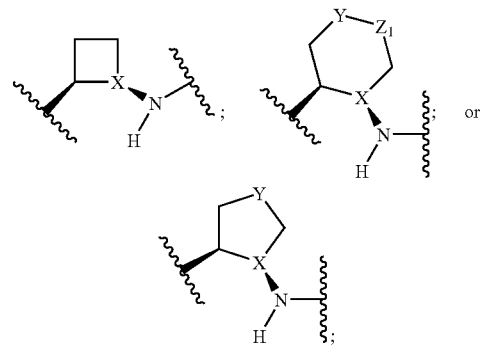

X is C(R$_8$);
Y is CH(R$_{1a}$), CH$_2$, O, S, S(O)$_2$, N(R$_8$), or C(=O);
Z$_1$ is CH(R$_7$), CH$_2$, O or N(R$_8$);
T is

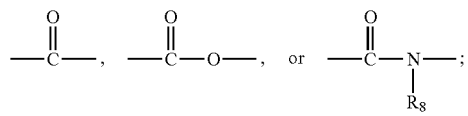

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is hydrogen, F, OH, or —NH$_2$;

R$_5$ is hydrogen, halo or —CN;

R$_{5a}$ is halo or —CN;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

In yet another embodiment, compounds of the present invention, or a stereoisomer or pharmaceutically acceptable salt from thereof, are those in which:

Z is O;

W is

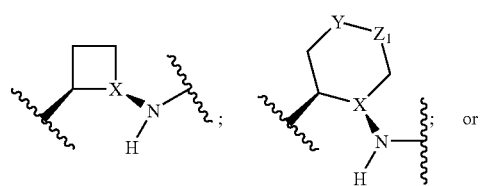

-continued

[structure with Y, X, N-H]

X is C(R$_8$);
Y is CH(R$_{1a}$), CH$_2$, O, S or S(O)$_2$;
Z$_1$ is CH(R$_7$), CH$_2$ or O;
T is $$-\overset{O}{\underset{\|}{C}}-, \quad -\overset{O}{\underset{\|}{C}}-O-, \quad \text{or} \quad -\overset{O}{\underset{\|}{C}}-\underset{R_8}{N}-;$$

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is F, OH, or —NH$_2$;

R$_5$ is hydrogen, halo or —CN;
R$_{5a}$ is halo or —CN;
R$_{5b}$ is hydrogen, halo or —CN;
R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R₁₀, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R₁₀ₐ, and the heterocyclyl and heterocyclylalkyl contain 1-4 heteroatoms selected from N, O, and S;

R₁₀ₐ, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO₂, —C(=O)O(CR₈R₈)ᵣR₁₄, —O(CF₂)ᵣCF₃, —O(CR₈R₈)ᵣR₁₄, —OH, —SH, —S(CR₈R₈)ᵣR₁₄, —C(=O)NR₁₄R₁₄, —NR₁₄R₁₄, —S(O)₂NR₁₄R₁₄, —NR₁₄S(O)₂(CF₂)ᵣCF₃, —C(=O)NR₁₄S(O)₂R₆, —S(O)₂NR₁₄C(=O)OR₆, —S(O)₂NR₁₄C(=O)NR₁₄R₁₄, —C(=O)NR₁₄S(O)₂(CF₂)ᵣCF₃, —C(=O)(CR₈R₈)ᵣR₁₄, —NR₁₄C(=O)H, —NR₁₄C(=O)(CR₈R₈)ᵣR₁₄, —OC(=O)(CR₈R₈)ᵣR₁₄, —S(=O)(CR₈R₈)ᵣR₁₄, —S(O)₂(CR₈R₈)ᵣR₁₄, —NR₁₄C(=O)OR₆, —NR₁₄S(O₂)R₆, —OC(=O)NR₁₄R₁₄, aryloxy or arylalkyl;

R₁₄, at each occurrence, is independently selected from hydrogen, alkyl, cycloalkyl or phenyl;

m is 0-2; and r is 0-2.

In still yet another embodiment, compounds of the present invention, or a stereoisomer or pharmaceutically acceptable salt from thereof, are those in which:

Z is O;

W is

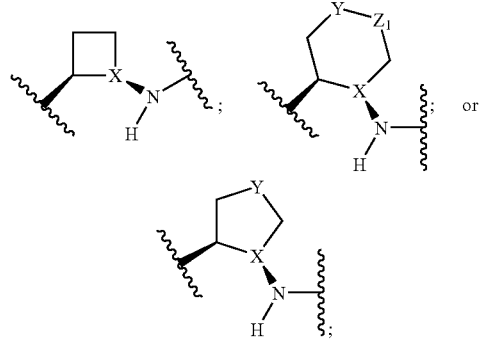

X is C(R₈);
Y is CH(R₁ₐ), CH₂, O or S;
Z₁ is CH(R₇) or CH₂;
T is

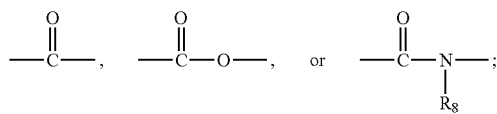

R₁ is alkyl, cycloalkyl, aryl, heterocyclyl or heteroaryl, all of which may be optionally substituted with 0-5 R₁ₐ;

R₁ₐ, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, —NR₉S(O₂)R₆, =O, —OC(=O)NR₉R₉, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R₁ᵦ;

R₁ᵦ, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, —NR₉S(O₂)R₆, aryloxy, arylalkyl or arylalkyloxyalkyl;

R₃, at each occurrence, is independently OH or alkyl; or two R₃'s together with the carbon atom to which they are attached may form a 3- to 6-membered ring;

R₄ is F or OH;

R₅ is hydrogen, halo or —CN;

R₅ₐ is halo or —CN;

R₅ᵦ is hydrogen, halo or —CN;

R₆, at each occurrence, is independently alkyl, cycloalkyl, cycloalkylalkyl, aryl, arylalkyl, heteroaryl or heteroarylalkyl;

R₇, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, —NR₉S(O₂)R₆, =O, —OC(=O)NR₉R₉, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R₇ᵦ;

R₇ᵦ, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO₂, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —S(=O)(CR₈R₈)ᵣR₁₀, —S(O)₂(CR₈R₈)ᵣR₁₀, —NR₉C(=O)OR₆, —NR₉S(O₂)R₆, aryloxy, arylalkyl or arylalkyloxyalkyl;

R₈, at each occurrence, is independently hydrogen or alkyl;

R₉, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R₉ₐ, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 0-2; and r is 0-2.

In one embodiment, compounds of the present invention, or a stereoisomer or pharmaceutically acceptable salt from thereof, are those in which:

Z is O;

W is

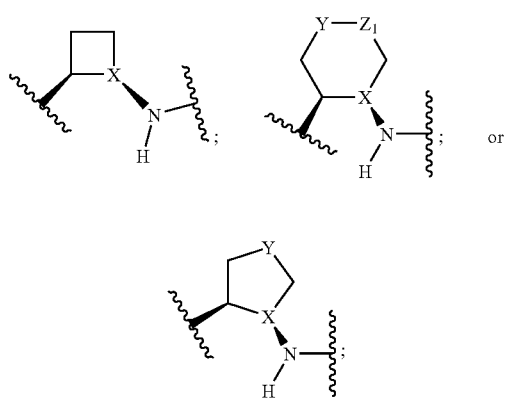

X is C(R$_8$);

Y is CH(R$_{1a}$), CH$_2$ or O;

Z$_1$ is CH(R$_7$) or CH$_2$;

T is

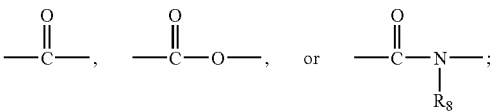

$R_1$ is alkyl, cycloalkyl, aryl, heterocyclyl or heteroaryl, all of which may be optionally substituted with 0-5 R$_{1a}$;

$R_{1a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$;

$R_{1b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

$R_3$, at each occurrence, is alkyl;

$R_4$ is OH;

$R_5$ is hydrogen or halo;

$R_{5a}$ is halo or —CN;

$R_{5b}$ is hydrogen or halo;

$R_6$, at each occurrence, is independently alkyl, cycloalkyl, aryl or heteroaryl;

$R_7$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

$R_{7b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt from thereof, are those in which:

Z is O;

W is

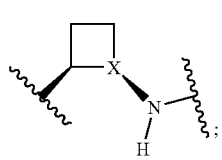 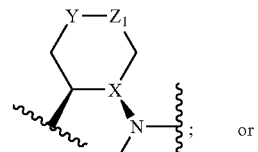 or

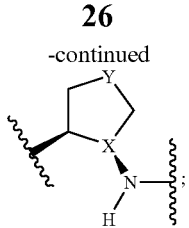

X is C(R$_8$);
Y is CH(R$_{1a}$) or CH$_2$;
Z$_1$ is CH(R$_7$) or CH$_2$;
T is

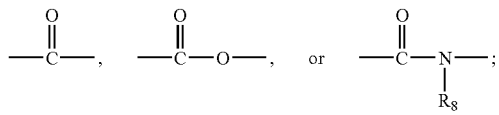

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, or aryloxy, wherein the alkyl, aryl, cycloalkyl, heteroaryl, heterocyclyl and aryloxy may be optionally substituted with 0-3 R$_{1b}$;

R$_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, or aryloxy;

R$_3$, at each occurrence, is alkyl;
R$_4$ is OH;
R$_5$ is hydrogen or halo;
R$_{5a}$ is halo;
R$_{5b}$ is hydrogen or halo;
R$_6$, at each occurrence, is independently alkyl, cycloalkyl, aryl or heteroaryl;
R$_7$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$ or aryloxy, wherein the alkyl, aryl, cycloalkyl, heteroaryl, heterocyclyl and aryloxy may be optionally substituted with 0-3 R$_{7b}$;

R<sub>7b</sub>, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$ or aryloxy;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$ or aryloxy;

R$_{14}$, at each occurrence, is independently selected from hydrogen, alkyl, cycloalkyl or phenyl;

m is 0-2; and r is 0-2.

In another embodiment, compounds of the present invention, or a stereoisomer or pharmaceutically acceptable salt from thereof, are those in which:

Z is O;

W is

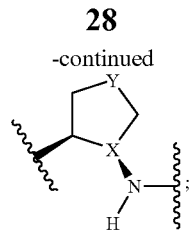

-continued

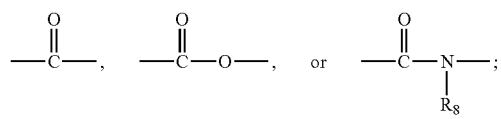

X is CH;
Y is CH$_2$;
Z$_1$ is CH$_2$;
T is $$-\overset{O}{\underset{}{C}}-, \quad -\overset{O}{\underset{}{C}}-O-, \quad \text{or} \quad -\overset{O}{\underset{\underset{R_8}{|}}{C}}-N-;$$

R$_1$ is alkyl, cycloalkyl, aryl or heteroaryl, all of which may be optionally substituted with 0-5 R$_{1a}$;

R$_{1a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, —OC(=O)NR$_9$R$_9$, or aryloxy, wherein the alkyl, aryl, cycloalkyl, heteroaryl, heterocyclyl and aryloxy may be optionally substituted with 0-3 R$_{1b}$;

R$_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, or aryloxy;

R$_3$, at each occurrence, is alkyl;

R$_4$ is OH;

R$_5$ is hydrogen or halo;

R$_{5a}$ is chloro;

R$_{5b}$ is hydrogen or halo;

R$_6$, at each occurrence, is independently alkyl, cycloalkyl, aryl or heteroaryl;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)

$NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$, or aryloxy;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, $-CN$, $-NO_2$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, $-OC(=O)NR_{14}R_{14}$ or aryloxy;

$R_{14}$, at each occurrence, is independently selected from hydrogen, alkyl, cycloalkyl or phenyl;

m is 0-2; and r is 0-2.

In one embodiment, compounds of the present invention, or a stereoisomer or pharmaceutically acceptable salt from thereof, are those in which:

Z is O;

W is

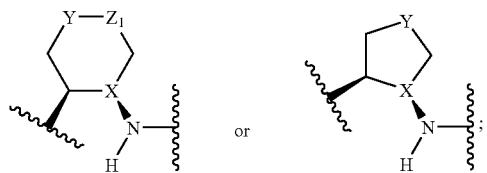

X is CH;
Y is $CH_2$;
$Z_1$ is $CH_2$;
T is

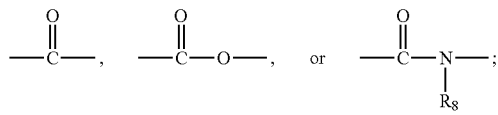

$R_1$ is alkyl, aryl or heteroaryl, all of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, $-CN$, $-NO_2$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-S(=O)(CR_8R_8)_rR_{10}$, $-S(O)_2(CR_8R_8)_rR_{10}$, $-NR_9C(=O)OR_6$, $-NR_9S(O)_2R_6$, or $-OC(=O)NR_9R_9$, wherein the alkyl, aryl, cycloalkyl, heteroaryl and heterocyclyl may be optionally substituted with 0-3 $R_{1b}$;

$R_{1b}$, at each occurrence, is independently selected from alkyl, haloalkyl, aryl, cycloalkyl, heteroaryl, heterocyclyl, halo, $-CN$, $-NO_2$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-S(=O)(CR_8R_8)_rR_{10}$, $-S(O)_2(CR_8R_8)_rR_{10}$, $-NR_9C(=O)OR_6$, or $-NR_9S(O)_2R_6$;

$R_3$, at each occurrence, is alkyl;
$R_4$ is OH;
$R_5$ is hydrogen or halo;
$R_{5a}$ is chloro;
$R_{5b}$ is hydrogen or halo;
$R_6$, at each occurrence, is independently alkyl, cycloalkyl, aryl or heteroaryl;
$R_8$, at each occurrence, is independently hydrogen or alkyl;
$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, heteroaryl, heterocyclyl, halo, $-CN$, $-NO_2$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, or $-OC(=O)NR_{14}R_{14}$;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heteroaryl, heterocyclyl, halo, $-CN$, $-NO_2$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-S(=O)(CR_8R_8)_rR_{14}$, $-S(O)_2(CR_8R_8)_rR_{14}$, $-NR_{14}C(=O)OR_6$, $-NR_{14}S(O_2)R_6$, or $-OC(=O)NR_{14}R_{14}$;

$R_{14}$, at each occurrence, is independently selected from hydrogen, alkyl, cycloalkyl or phenyl;

m is 0 or 2; and r is 0-2.

In one embodiment, compounds of the present invention, or a stereoisomer or pharmaceutically acceptable salt from thereof, are those in which:

Z is O;

W is

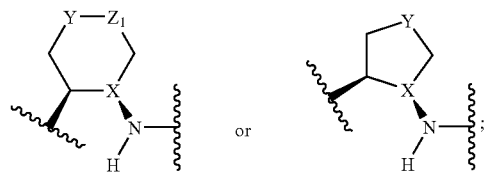

X is CH;
Y is CH$_2$;
Z is CH$_2$;
T is

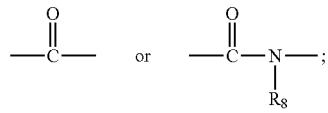

R$_1$ is alkyl or phenyl, both of which may be optionally substituted with 0-5 R$_{1a}$;

R$_{1a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$ or aryloxy, wherein the alkyl, aryl, cycloalkyl, heteroaryl, heterocyclyl or aryloxy may be optionally substituted with 0-3 R$_{1b}$;

R$_{1b}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, or aryloxy;

R$_3$ is methyl;
R$_4$ is OH;
R$_5$ is hydrogen or halo;
R$_{5a}$ is chloro;
R$_{5b}$ is hydrogen or halo;
R$_6$, at each occurrence, is independently alkyl, cycloalkyl, aryl or heteroaryl;
R$_8$, at each occurrence, is independently hydrogen or alkyl;
R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$ or aryloxy;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$ or aryloxy;

R$_{14}$, at each occurrence, is independently selected from hydrogen, alkyl, cycloalkyl or phenyl;
m is 2; and
r is 0-2.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent as known to one of ordinary skill in the art.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

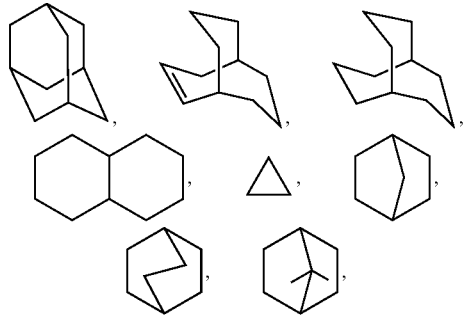

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example:

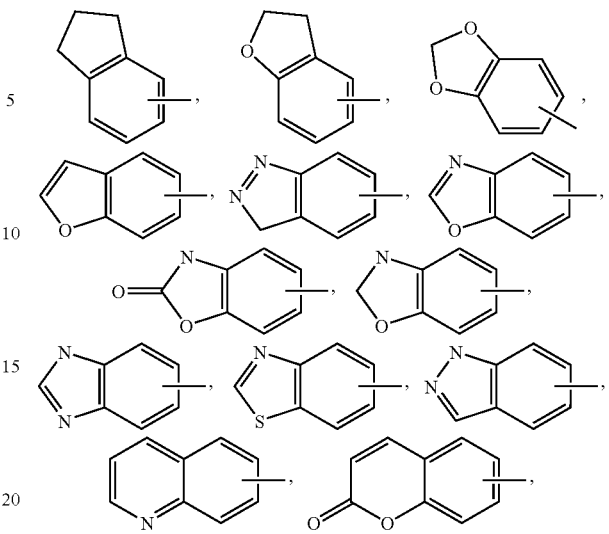

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl,indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., p. 1418 (Mack Publishing Company, Easton, Pa., 1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry,* Camille G. Wermuth et al., Ch. 31 (Academic Press, 1996);
b) *Design of Prodrugs,* edited by H. Bundgaard (Elsevier, 1985);
c) *A Textbook of Drug Design and Development,* P. Krogsgaard-Larsen and H. Bundgaard, eds. Ch. 5, pp. 113-191 (Harwood Academic Publishers, 1991); and
d) *Hydrolysis in Drug and Prodrug Metabolism,* Bernard Testa and Joachim M. Mayer (Wiley-VCH, 2003).
Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* Third Edition (Wiley and Sons, 1999)).

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Chemokine receptor antagonists of the present invention can be prepared from the protected amino acid derivative 1.1 by coupling with a piperidine 1.2 (see syntheses disclosed in International Patent Application No. WO 04/043965) under standard amide bond forming conditions to yield 1.3 as shown in Scheme 1. Deprotection of the nitrogen can provide an amine 1.4 which can be reacted further with derivatizing reagents to provide (I).

Scheme 1

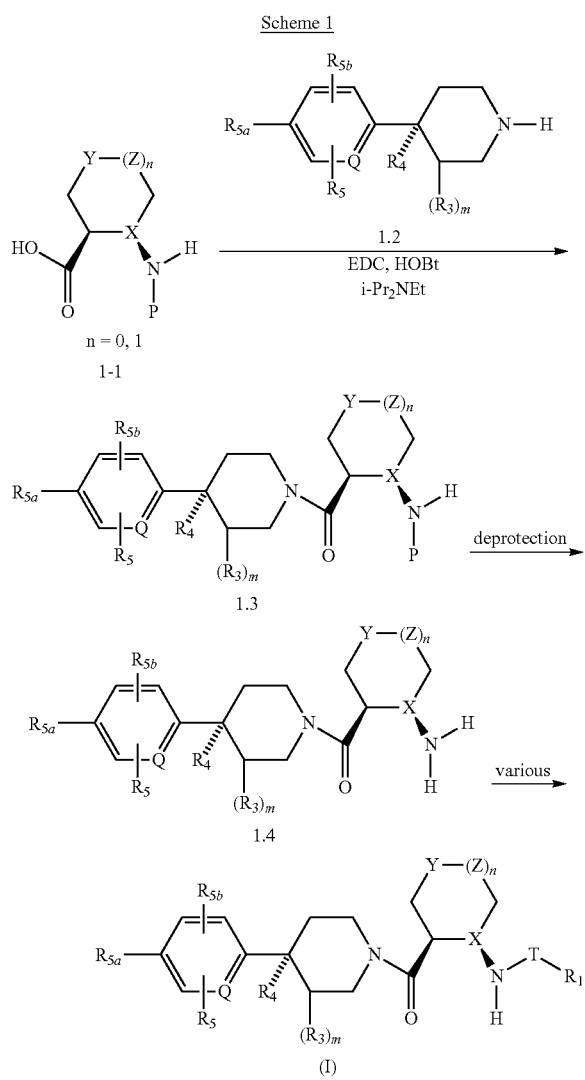

Alternatively, compounds of the present invention can be synthesized as shown in Scheme 2. Coupling of the functionalized amino acid derivative 2.1 with piperidine 1.2 under standard amide bond forming conditions can provide compound I.

Scheme 2

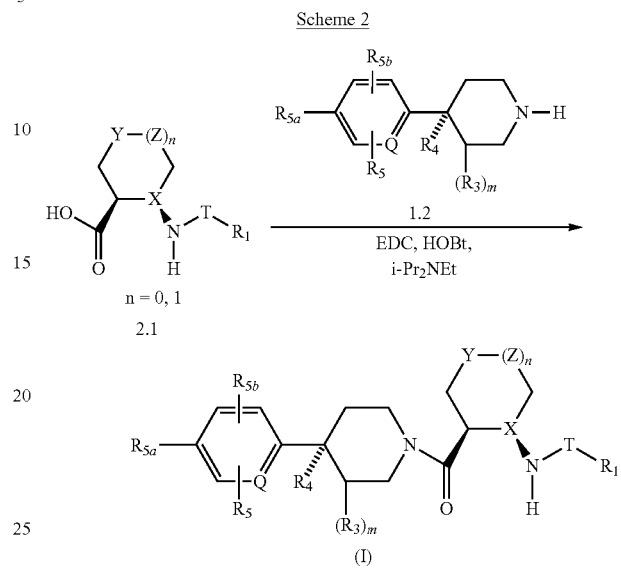

The linkers represented by W in the scope of this application are available commercially or can be synthesized by the methods disclosed in Cimarelli, C. et al., *J. Org. Chem.* 1996, 61, 5557-5563 and Hanselmann, R. et al., *J. Org. Chem.* 2003, 68, 8739-8741 and modifications thereof. For example, the cyclohexyl β-amino acid template (W is a 6-membered ring and X, Y, Z, =CH$_2$) may be synthesized as shown in Scheme 3. Ketoester 3.1 can be condensed with chiral amine 3.2 to form 3.3. Reduction, either with STAB or as shown here via catalytic hydrogenation can yield the major aminoester diastereomer shown (3.4) together with a small amount of minor diastereomer. Crystallization with an acid such as toluenesulfonic acid can produce the salt 3.5. Hydrogenolysis of the α-methylbenzyl group can yield aminoester 3.6. Hydrolysis with HCl followed by protection with BOC and coupling with piperidine 3.9 can yield 3.10. Deprotection of the BOC group can yield amine 3.11 which can further be derivatized as described in Scheme 1.

Scheme 3

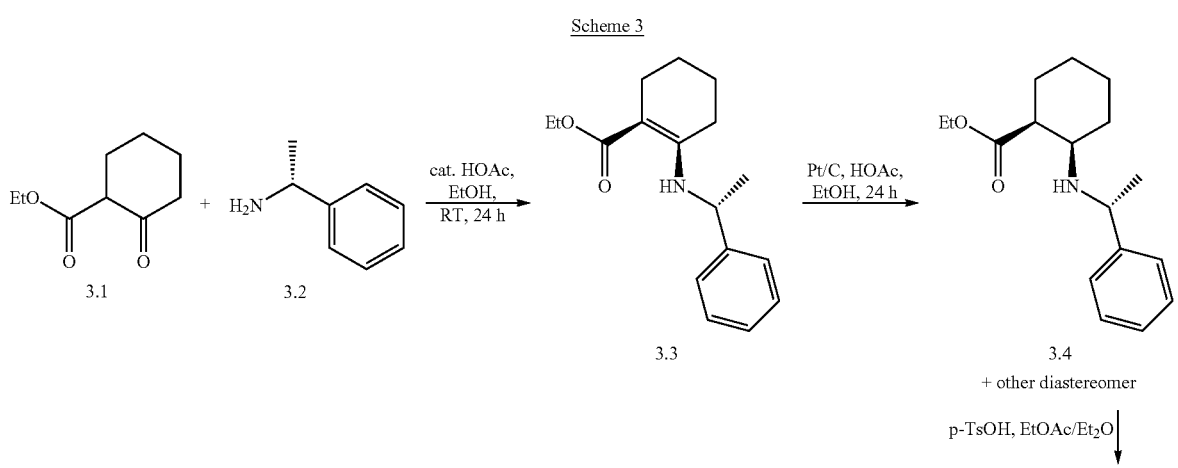

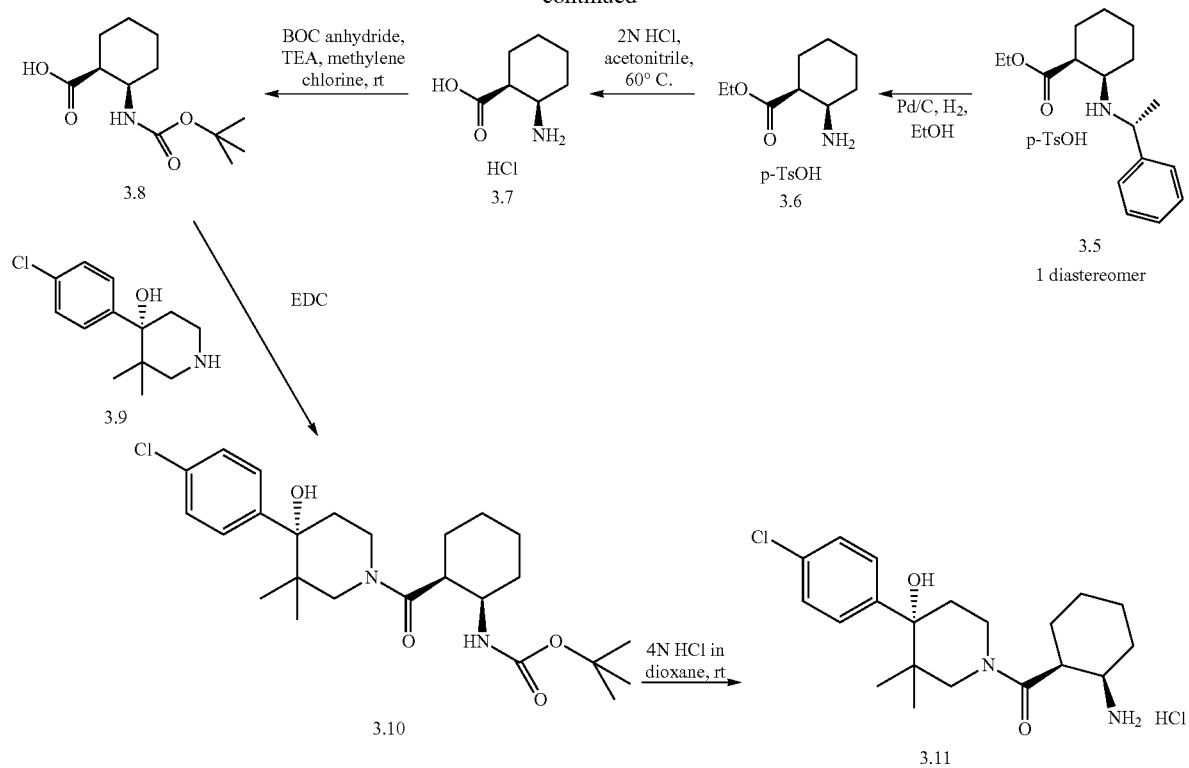

A resin supported synthesis can also be employed using the reactions outlined in Scheme 4. Coupling of an amine ester to a properly functionalized resin can give 4.1 which upon amine functionalization can form 4.2. Standard saponification can yield the pendant acid derivatized resin 4.3. Amide bond formation with amine 1.2 can furnish analog 4.4. Removal from the resin using acid can furnish the piperidine (I) from 4.4.

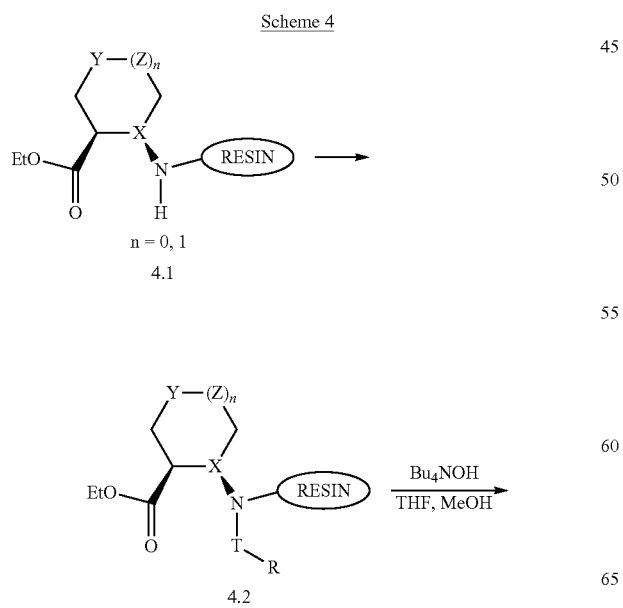

Compounds of the invention can also be prepared according to the methods outlined in Scheme 5. An appropriately functionalized amine 1.4 can be reacted with an isothiocyanate followed by alkylation in the presence of a base with iodomethane to furnish 5.1. Compound 5.1 can be further reacted with, for example a hydrazine or a hydroxylamine derivative, to furnish the substituted triazole or the oxadiazole of the present invention.

*Reactions* (2nd Edition) 2004, 2, 699-760; Anderson, K. W. et al., "Palladium-Catalyzed Amination of Aryl Nonaflates", *J. Org. Chem.* 2003, 68(25), 9563-9573; Kwong, F. Y. et al., *Org. Lett.* 2002, 5(6), 793-796; Wolfe, J. et al., *J. Org. Chem.*

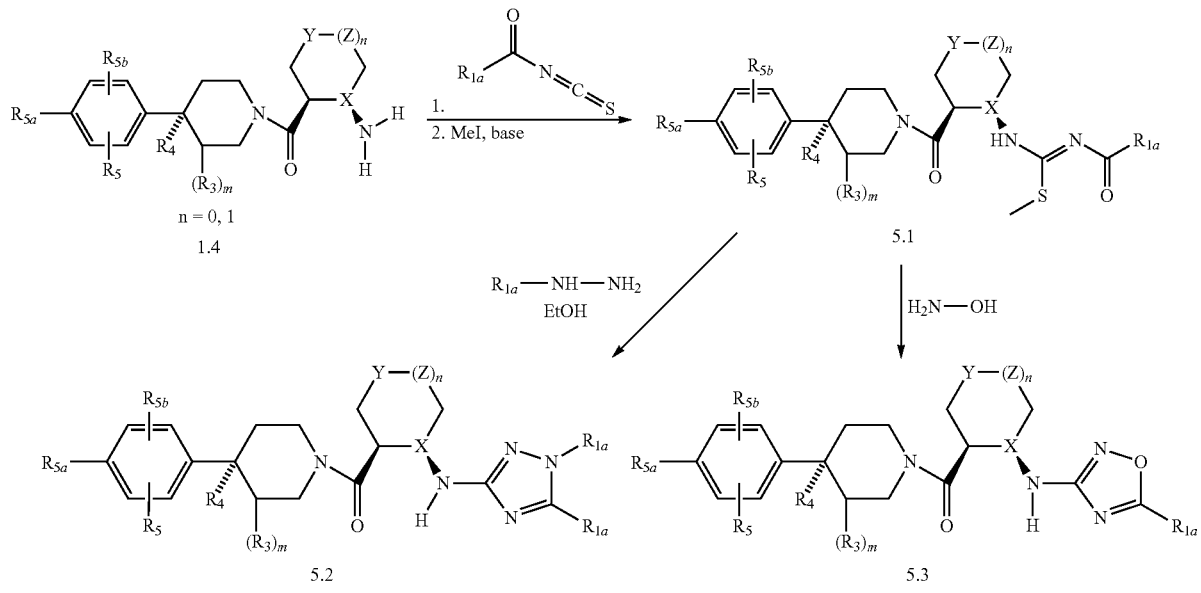

Scheme 5

Furthermore, compounds of the present invention can be prepared by reaction of amine 1.4 with an appropriate boronic acid-containing aryl or heteroaryl group in the presence of a catalyst to yield coupled product 6.2 (Scheme 6) (for review of the Chan-Lam Reaction, see Chan, D. M. T. et al., "Recent Advances in Copper-Promoted C-Heteroatom Bond Cross-Coupling Reactions with Boronic Acids and Derivatives" in *Boronic Acids*, Hall, D. G., ed., ((Wiley-VCH Verlag GmbH & Co., Weinheim, 2005). ISBN 3-527-30991-8). Other N-arylation or N-heteroarylation methods include reaction of an amine and an aryl iodide (or bromide) or a heteroaryl iodide (or bromide) in the presence of a palladium catalyst (see Charles, M. D. et al., *Org. Lett.* 2005, 7(18), 3965-3968; Jiang, L. et al., "Palladium-catalyzed aromatic carbon-nitrogen bond formation" in *Metal-Catalyzed Cross-Coupling*

1997, 62, 6066-6078; Wolfe, J. et al., *J. Am. Chem. Soc.* 1996, 118, 7215-7216, and references therein). Activated halogens on aryl rings and on heterocycles can be displaced by amine 1.4 to yield the N-arylated/heteroarylated products 6.2 and 6.3, respectively. For example, fluorophenyls with ortho- or para-nitro groups or other electron-withdrawing groups undergo the nucleophilic aromatic substitution reaction in polar solvents such as DMF or DMSO. Heterocyclic halogens substituted on carbon located alpha to neighboring heteroatoms can often be displaced by amines in a polar solvent with heating or in a microwave reactor. For a review on these aryl/heteroaryl displacement reactions, see Dimethyl Sulfoxide (DMSO) Technical Bulletin, Crown Zellerbach Corporation, Chemical Products Division.

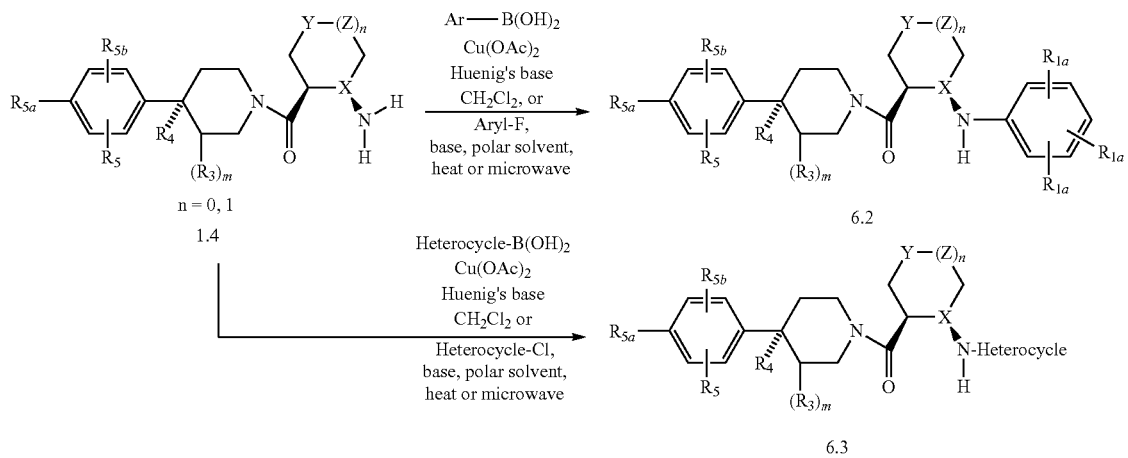

Scheme 6

Alternatively, compounds of the present invention can be synthesized as shown in Scheme 7. Reacting a properly functionalized analog of compounds of the present invention under a variety of conditions known to those skilled in the art can provide additional compounds of the present invention. It is to be assumed that the examples shown in Scheme 7 are merely representative of a variety of transformations and interconversions of functionality that are possible with the knowledge of one skilled in the art of organic synthesis. For example, it is to be understood that phenylboronic acids or phenyltrialkyltin can be replaced with heteroaryl or protected heteroaryl and possibly other moieties and that the phenyl is only used as an example.

Furthermore, compound 1.4 can be reacted with an anhydride or an acid chloride to provide the amide 8.1 (Scheme 8). It can also be reacted with a sulfonyl chloride to yield sulfonamide 8.2. Likewise, 1.4 can be reacted with a haloacetyl halide, such as chloroacetyl chloride, followed by a nucleophile, such as a heterocyclic anion or a basic heterocycle, to give the substituted amide 8.3. Other non-heterocyclic nucleophiles which can also be reacted and are familiar to one skilled in the art include but are not limited to azide, cyano, $R_1$—$S^-$, $R_1$-amino, etc. Some of these can be further elaborated into other functionality within the scope of this application by methods familiar to one skilled in the art.

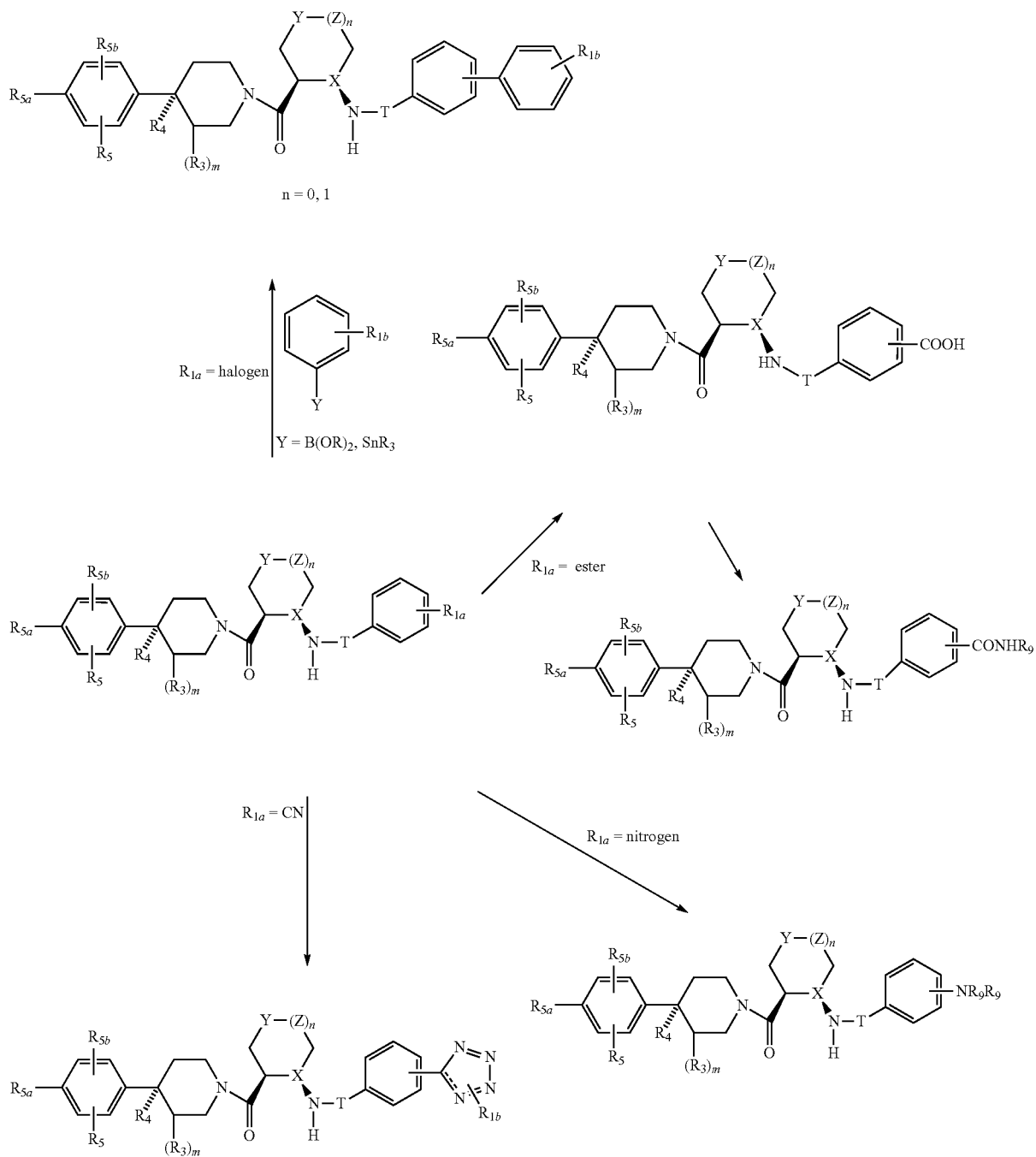

Scheme 8

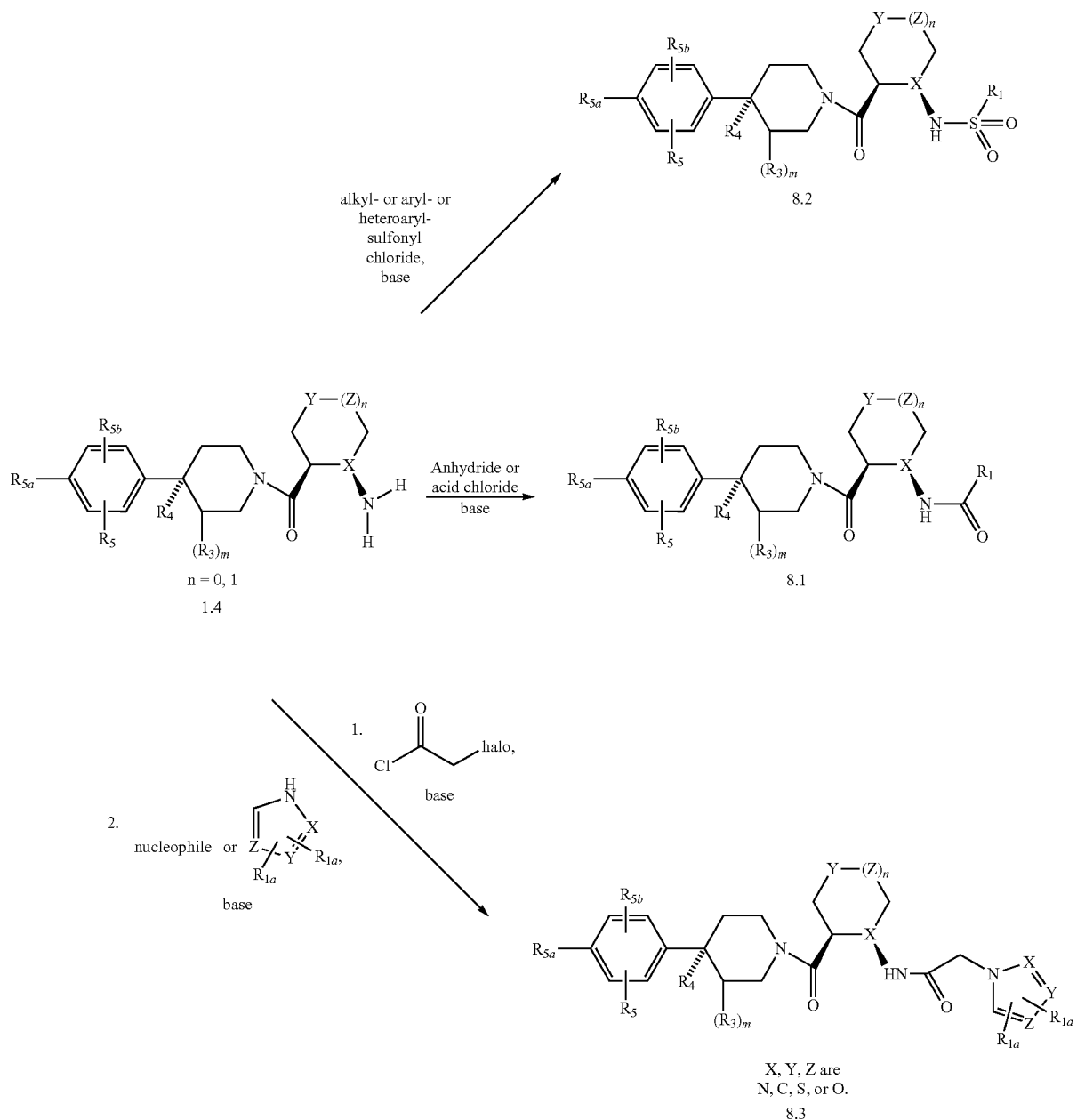

Scheme 9 outlines methods to synthesize T=—CO—O— (carbamates) and —CO—NR[8]— (ureas). For example, amine 1.4 can be reacted with a chloroformate in the presence of a base such as triethylamine or Hunig's in an aprotic solvent to yield carbamate 9.1. If this carbamate is a phenyl carbamate or a 4-nitrophenylcarbamate or a pentafluorophenylcarbamate or any other phenylcarbamate with an electron withdrawing group(s), then the phenoxy of the carbamate may be displaced by an amine at RT to reflux temperature of the inert solvent to yield urea 9.2. Likewise, amine 1.4 may be reacted in an inert solvent with an isocyanate to yield 9.2 where $R_8$=H, or may be reacted in an inert solvent in the presence of a base such as triethylamine or Hunig's base with a carbamoyl chloride to yield 9.2 where $R_8 \neq H$. Furthermore, cyanoguanidines (T=—(C=N—CN)$NR_8$—) can be synthesized by the method of K. S. Atwal et al. and references contained therein (*J. Med. Chem.* 1998, 41, 217-275) (not shown). Squaric acid-type isosteres can be synthesized by the method of Poindexter, G. S. et al., (*Bioorg. Med. Chem.* 2004, 12, 507-521) (not shown).

Scheme 9

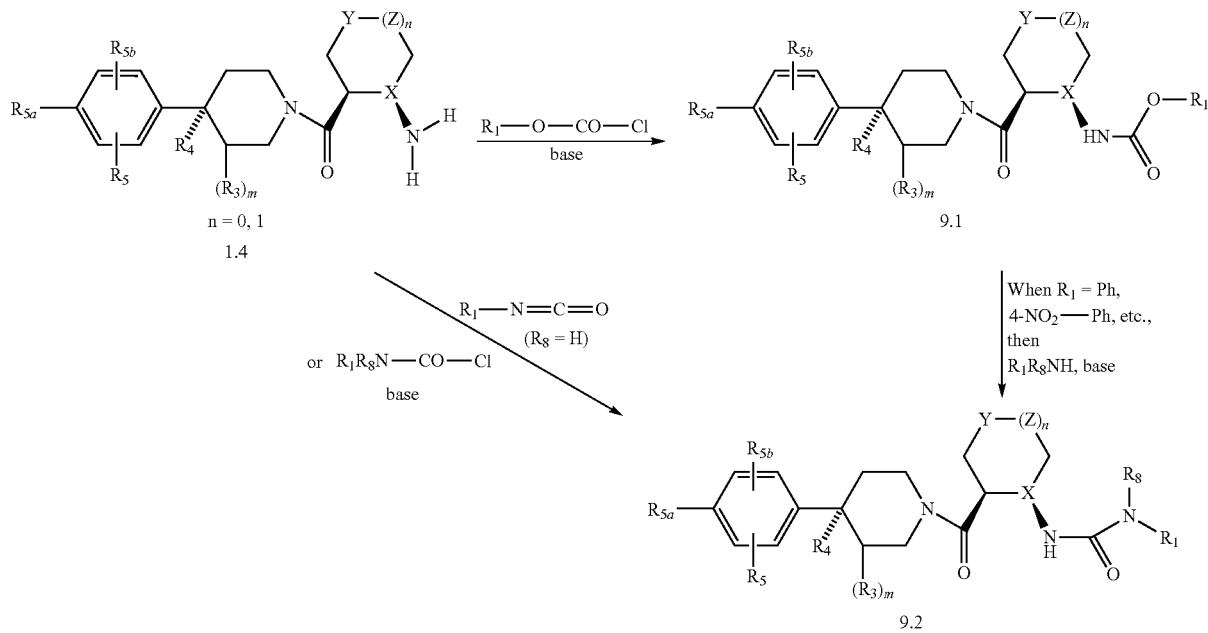

EXAMPLES

Abbreviations used in the Examples are defined as follows: "1×" for once, "2×" for twice, "3×" for thrice, "5×" for five times, "Boc" for tert-butyloxycarbonyl, "BOP" for Benzotriazole-1-yl-oxy-tris-(dimethylamino)-phosphonium hexafluorophosphate, "° C." for degrees Celsius, "psi" for pounds per square inch, "Et$_2$O" for diethyl ether, "Cbz" for benzyloxycarbonyl, "CH$_3$MgBr" for methyl magnesium bromide, "DCM" for dichloromethane, "DMF" for N,N-dimethylformamide, "DIPEA" for N,N-diisopropylethylamine, "NaOH" for sodium hydroxide, "EDC" for N-(3-dimethylaminopropyl)-N-ethylcarbodiimide hydrochloride, "MgSO$_4$" for magnesium stearate, "Pt/C" for platinum on carbon, "Pd/C" for palladium on carbon "EtOAc" for ethyl acetate, "K$_2$HPO$_4$" for potassium hydrogen phosphate, "eq" or "equiv." for equivalent or equivalents, "aq." for aqueous, "g" for gram or grams, "HOBt" for 1-hydroxybenzotriazole, "LC" for liquid chromatography, "mg" for milligram or milligrams, "mL" for milliliter or milliliters, "µL" for microliter or microliters, "h" for hour or hours, "mmol" for millimolar, "M" for molar, "N" for normal, "HCl" for hydrochloric acid, "MeCN" for acetonitrile", "MeOH" for methanol, "KOH" for potassium hydroxide, "min" for minute or minutes, "MS" for mass spectroscopy, "rt." or "RT" for room temperature, "TFA" for trifluoroacetic acid, "THF" for tetrahydrofuran, "LiOH" for lithium hydroxide, "NaBH$_4$" for sodium borohydride, "Pd(OH)$_2$" for palladiumhydroxide, "HBr" for hydrogen bromide, "NaNO$_2$" for sodium nitrite, "p-TsOH" for p-Toluenesulfonic acid, "Pd(OAc)$_2$" for palladium acetate, "Pd$_2$(dba)$_3$" for tris(dibenzylidineacetone)dipalladium (0), "S-Phos" for 2-dicyclohexylphosphino-2',6'-dimthoxy-1,1'-biphenyl, "grad" for gradient, and "v/v" for volume to volume ratio. "D", "L", "R" and "S" are stereochemical designations familiar to those skilled in the art. Chemical names were derived using ChemDraw Ultra, version 8.0.8. When this program failed to provide a name for the exact structure in question, an appropriate name was assigned using the same methodology utilized by the program.

Example 1 tert-Butyl (1R,2S)-2-((S)-4-(4-chlorophenyl)-4-hydroxy-3,3-dimethylpiperidine-1-carbonyl)cyclohexylcarbamate

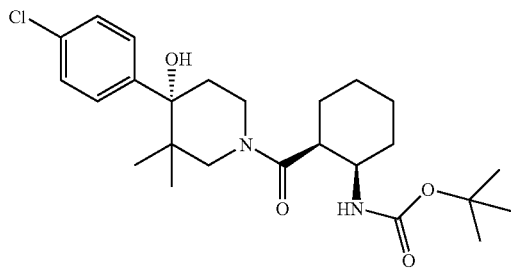 [SMILES: CC(C)(C)OC(=O)N[C@@H]1CCCC[C@@H]1C(=O)N1CC[C@](O)(c2ccc(Cl)cc2)C(C)(C)C1]

Step 1: (1S,2R)-Ethyl 2-((R)-1-phenylethylamino)cyclohexanecarboxylate

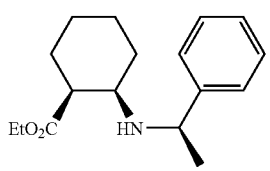 [SMILES: CCOC(=O)[C@H]1CCCC[C@H]1N[C@H](C)c1ccccc1]

Ethyl 2-oxocyclohexanecarboxylate ((5.00 mL, 31.3 mmol, 1 eq), R-(+)-methylbenzylamine (4.77 mL, 37.5 mmol, 1.2 eq), glacial acetic acid (0.054 mL, 0.94 mmol, 0.03 eq) and ethanol (20 mL) were mixed and stirred at RT for 48 h. The entire contents were poured into a flask containing 5% Pt/C (1.05) which had been previously carefully wetted down with ethanol (50 mL) under nitrogen. Glacial acetic acid (4.5 mL) was then added thereto and the entire mixture hydrogenated on a Parr shaker apparatus for about 16 hours at 55 psi. The mixture was carefully filtered through fiberglass filter paper under nitrogen. The filtrate was concentrated and the residue dissolved in EtOAc. The mixture was washed with 5% $K_2HPO_4$ (aq) until the pH was 8 (total of 3 washes). The organic layer was then washed with brine (1×), dried over $MgSO_4$ and the solvent removed in vacuo. The resulting residue was flash chromatographed over silica gel in 9:1 hexanes/EtOAc to 7:3 hexanes/EtOAc. The fractions were collected and the solvent concentrated to yield 6.69 grams of a clear, colorless oil. LCMS shows two peaks in an 82:8 ratio. MS $(ESI^+)$=276.29/278.32 $(M+H)^+$.

Step 2: (1S,2R)-Ethyl 2-((R)-1-phenylethylamino) cyclohexanecarboxylate, p-TsOH salt

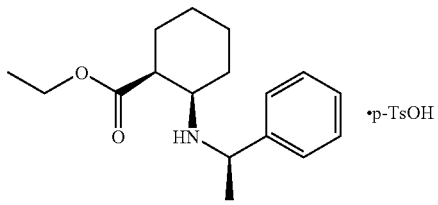 [SMILES: CCOC(=O)[C@H]1CCCC[C@H]1N[C@H](C)c1ccccc1]

(1S,2R)-Ethyl 2-(1-phenylethylamino)cyclohexanecarboxylate (6.50 g, 23.60 mmol) was dissolved in ethyl acetate (40 mL) with stirring at 25° C. p-Toluenesulfonic acid (4.49 g, 23.60 mmol) was added in 1 portion thereto. Solids precipitated within 1 minute and $Et_2O$ (40 mL) was added to help with stirring. The mixture was stirred for 20 minutes. The solids were then filtered, rinsed with $Et_2O$ (40 mL) and then pumped under high vacuum to give (1S,2R)-ethyl 2-(1-phenylethylamino)cyclohexanecarboxylate, tosylic acid (8.5 g, 19.03 mmol, 81% yield) as a white fluffy solid. MS $(ESI^+)$=276.20 $(M+H)^+$.

Step 3: (1S,2R)-Ethyl 2-aminocyclohexanecarboxylate, p-TsOH salt

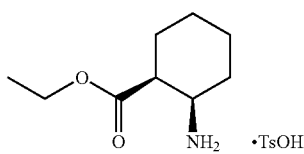

10% Pd/C (Degussa, 50% wet, 0.87 g) was carefully wetted down under argon with ethanol, then (1S,2R)-ethyl 2-((R)-1-phenylethylamino)cyclohexane-carboxylate, tosylic acid (8.7 g, 19.4 mmol) in ethanol (75 mL) was added. The mixture was then hydrogenated for 20 hours at 50 psi in a Parr shaker apparatus. Under argon, the catalyst was filtered off. The filtrate was resubjected to hydrogenation, this time with 1.70 grams of 10% Pd/C (Degussa, 50% wet). After 6 hours, the reaction was analyzed by LCMS, which detected little change. Under argon, the reaction was carefully filtered through a fiberglass filter paper. The filtrate was concentrated to give a colorless oil. The oil was resubjected to 10% Pd/C (Degussa, 50% wet, 1.70 grams) in 50 mL of ethanol and hydrogenated for 20 hours at 50 psi. Under argon, the reaction was carefully filtered through a fiberglass filter paper. The filtrate was concentrated to give (1S,2R)-ethyl 2-aminocyclohexanecarboxylate tosylic acid (5.4 g, 15.7 mmol, 81% yield) as a colorless oil. MS $(ESI^+)$=172.16 $(M+H)^+$.

Step 4: (1S,2R)-2-Aminocyclohexanecarboxylic acid, HCl salt

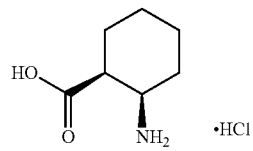

(1S,2R)-Ethyl 2-aminocyclohexanecarboxylate, tosylic acid (5.4 g, 15.7 mmol) was dissolved in acetonitrile (10 mL) at RT with stirring then 2N HCl (40 mL, 80 mmol) was added. The colorless solution was then warmed to 60° C. and stirred for 20 hours. The reaction was concentrated 3 times from isopropanol. The precipitating solids were collected by filteration and rinsed with isopropanol. The filtrate was concentrated to reduce the volume during which time more solids precipitated. These were filtered, rinsed with isopropanol, and dried to yield (1S,2R)-2-aminocyclohexanecarboxylic acid, HCl salt (1.7 g, 9.46 mmol, 60.2% yield) as a white solid. MS $(ESI^+)$=144.10 $(M+H)^+$.

Step 5: (1S,2R)-2-(tert-Butoxycarbonylamino)cyclohexanecarboxylic acid

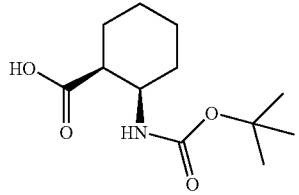 [SMILES: CC(C)(C)OC(=O)N[C@@H]1CCCC[C@@H]1C(=O)O]

(1S,2R)-2-Aminocyclohexanecarboxylic acid, HCl salt (1.7 g, 9.46 mmol) and triethylamine (1.319 mL, 9.46 mmol) were mixed in methylene chloride (20 mL) at 5° C. with stirring followed by the addition of BOC-anhydride (2.197 mL, 9.46 mmol). The mixture was stirred for 3 hours. The reaction was worked up by rinsing (2×) with 1N HCl. The organic layer was dried over sodium sulfate and concentrated to give (1S,2R)-2-(tert-butoxycarbonylamino)cyclohexanecarboxylic acid (2.2 g, 9.04 mmol, 96% yield) as a white glass. MS $(ESI^+)$=188.11 $(M+H-t-butyl)^+$.

Step 6: Example 1

(S)-4-(4-Chlorophenyl)-3,3-dimethylpiperidin-4-ol (prepared in a similar manner as described in International Patent Application No. WO 04/043965, 1.715 g, 7.15 mmol), (1S, 2R)-2-(tert-butoxycarbonylamino)cyclohexanecarboxylic acid (1.74 g, 7.15 mmol), HOBt (1.314 g, 8.58 mmol), EDC (1.645 g, 8.58 mmol) and triethylamine (1.994 mL, 14.30 mmol) were mixed in methylene chloride (25 mL) at 25° C.

and stirred for 20 hours. The reaction was worked up by adding methylene chloride and then rinsing with saturated sodium carbonate (1×). The methylene chloride layer was dried over sodium sulfate and concentrated to give an amber oil. The amber oil was purified on a preparatory LC, in 100% hexanes to 100% EtOAc over 60 minutes, loading crude material (in 10 mL of methylene chloride) onto a 330 gram prepacked silica gel column. Faster eluting fractions were collected to yield Example 1 (2.85 g, 6.13 mmol, 86%) as a white glass. MS (ESI$^+$)=465.23 (M+H)$^+$. $^1$H NMR (CD$_3$OD, 400 MHz) (NMR shows several rotamers) δ 7.50-7.45 (m, 2H), 7.32-7.27 (m, 2H), 6.32-6.00 (m, 0.5H), 4.20-3.92 (m, 2H), 3.68-3.56 (m, 1H), 3.18-3.01 (m, 2H), 2.88-2.43 (m, 1H), 1.90-1.27 (m, 16H), 0.85-0.63 (m, 6H). [LCMS method: Inj. Vol.=10 uL; Start % B=0; Final % B=100; Gradient Time=2 min; Flow Rate=5 ml/min; Wavelength=220; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=2.07 minutes.]

Example 2

N-((1R,2S)-2-((S)-4-(4-Chlorophenyl)-4-hydroxy-3,3-dimethylpiperidine-1-carbonyl)cyclohexyl)benzamide

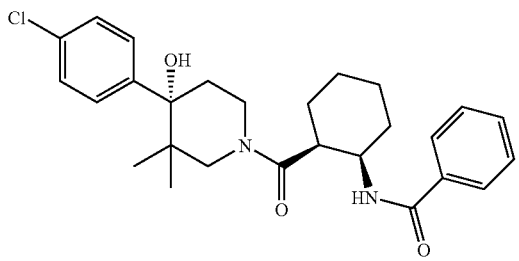 [SMILES: CC1(C)CN(C(=O)[C@H]2CCCC[C@H]2NC(=O)c2ccccc2)CC[C@]1(O)c1ccc(Cl)cc1]

Step 1: ((1S,2R)-2-Aminocyclohexyl)((S)-4-(4-chlorophenyl)-4-hydroxy-3,3-dimethylpiperidin-1-yl)methanone, HCl salt

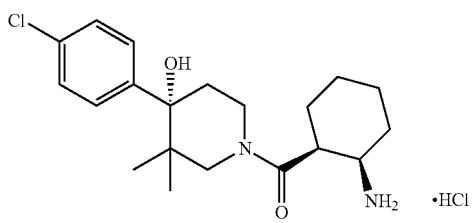 [SMILES: CC1(C)CN(C(=O)[C@H]2CCCC[C@H]2N)CC[C@]1(O)c1ccc(Cl)cc1 ; Cl]

tert-Butyl (1R,2S)-2-((S)-4-(4-chlorophenyl)-4-hydroxy-3,3-dimethylpiperidine-1-carbonyl)cyclohexylcarbamate (2.8 g, 6.02 mmol) was dissolved in dioxane (10 mL) at 25° C. with stirring and then 4N HCl in dioxane (7.53 mL, 30.1 mmol) was added. The mixture was stirred for 3 hours. Work up entailed concentrating the reaction (5×) from methylene chloride to obtain ((1S,2R)-2-aminocyclohexyl)((S)-4-(4-chlorophenyl)-4-hydroxy-3,3-dimethylpiperidin-1-yl)methanone, HCl salt (2.40 g, 5.98 mmol, 99% yield) as a white solid. MS (ESI$^+$)=365.27 (M+H−t-butyl)$^+$.

Step 2: Example 2

((1S,2R)-2-Aminocyclohexyl)((S)-4-(4-chlorophenyl)-4-hydroxy-3,3-dimethylpiperidin-1-yl)methanone, HCl salt (25 mg, 0.062 mmol), benzoic acid (7.61 mg, 0.062 mmol), HOBt (19.08 mg, 0.125 mmol), EDC (23.88 mg, 0.125 mmol) and triethylamine (0.043 mL, 0.311 mmol) were mixed in methylene chloride (3 mL) at 25° C. and stirred for 20 hours. The reaction was worked up by adding methylene chloride followed by rinsing with saturated sodium carbonate (1×). The methylene chloride layer was dried over sodium sulfate and concentrated to give a colorless oil. The colorless oil was purified by preparative HPLC/MS to yield Example 2 (20 mg, 0.034 mmol, 55.1% yield) as a white solid. MS (ESI$^+$)=469.26 (M+H)$^+$. $^1$H NMR (CD$_3$OD, 500 MHz) (NMR shows several rotamers) δ 7.79-7.75 (m, 2H), 7.58-7.44 (m, 4H), 7.38-7.22 (m, 3H), 4.55 (m, 0.5H), 4.39 (m, 0.5H), 4.19 (m, 0.5H), 4.04-3.96 (m, 1H), 3.67-3.58 (m, 1H), 3.43-3.35 (m, 1.5H), 3.13-2.98 (m, 1H), 2.73 (m, 0.5H), 2.52-2.41 (m, 1H), 2.20 (m, 0.5H), 2.04 (m, 0.5H), 1.92 (m, 0.5H), 1.81-1.65 (m, 3.5H), 1.58-1.43 (m, 3.5H), 0.79 (s, 0.5×3H), 0.77 (s, 0.5×3H), 0.74 (s, 0.5×3H), 0.65 (s, 0.5×3H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=2.01 minutes.]

Example 3

Methyl 3-((1R,2S)-2-((S)-4-(4-chlorophenyl)-4-hydroxy-3,3-dimethylpiperidine-1-carbonyl)cyclohexylcarbamoyl)benzoate

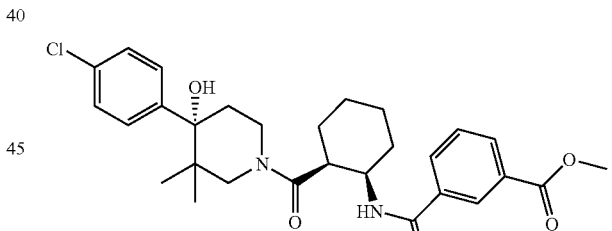

((1S,2R)-2-Aminocyclohexyl)((S)-4-(4-chlorophenyl)-4-hydroxy-3,3-dimethylpiperidin-1-yl)methanone, HCl salt (50 mg, 0.125 mmol), 3-(methoxycarbonyl)benzoic acid (22.44 mg, 0.125 mmol), HOBt (38.2 mg, 0.249 mmol), EDC (47.8 mg, 0.249 mmol) and triethylamine (0.087 mL, 0.623 mmol) were mixed in methylene chloride (3 mL) at 25° C. and stirred for 20 hours. The reaction was worked up by adding methylene chloride followed by rinsing with saturated sodium carbonate (1×). The methylene chloride layer was dried over sodium sulfate and concentrated to give a colorless oil. The colorless oil was purified over silica gel in 3:1 to 1:1 hexanes/EtOAc to 100% EtOAc to yield Example 3 (60 mg, 0.114 mmol, 91% yield) as a white glass. MS (ESI$^+$)=525.55 (M+H)$^+$. $^1$H NMR (CD$_3$OD, 400 MHz) (NMR shows several rotamers) δ 8.39 (s, 1H), 8.20 (d, 0.5H, J=8.0 Hz), 8.16 (d, 0.5H, J=8.0 Hz), 8.00 (d, 0.5H, J=8.0 Hz), 7.98 (d, 0.5H, J=8.0 Hz), 7.62 (app. t, 0.5H, J=8.0 Hz), 7.58 (app. t, 0.5H, J=8.0 Hz), 7.48 (d, 1H, J=8.0 Hz), 7.35 (d, 1H, J=8.0 Hz), 7.30 (d, 1H, J=8.0 Hz), 7.23 (d, 1H, J=8.0 Hz), 4.56 (m, 0.5H), 4.42 (m, 0.5H), 4.20 (m, 0.5H), 4.08-3.90 (m, 1H), 3.96 (s, 0.5×3H), 3.94 (s, 0.5×3H), 3.68-3.56 (m, 1H), 3.46-3.34 (m, 2H), 3.15-3.00 (m, 1H), 2.74 (m, 0.5H), 2.50 (m, 1H), 2.20 (m, 0.5H), 2.06 (m, 1H), 1.90 (m, 0.5H), 1.82-1.66 (m, 3.5H), 1.66-1.43 (m, 3.5H), 0.78 (s, 0.5×3H), 0.77 (s, 0.5×3H), 0.74 (s, 0.5×3H), 0.65 (s, 0.5×3H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=2.02 minutes.]

Example 4

3-((1R,2S)-2-((S)-4-(4-Chlorophenyl)-4-hydroxy-3,3-dimethylpiperidine-1-carbonyl)cyclohexylcarbamoyl)benzoic acid

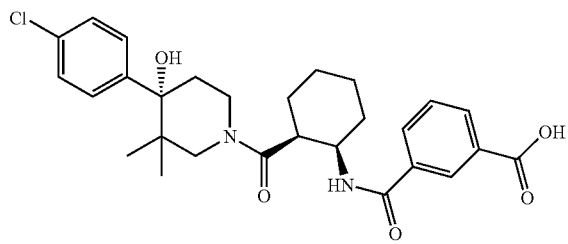 [SMILES: CC1(C)CN(C(=O)[C@H]2CCCC[C@H]2NC(=O)c2cccc(C(=O)O)c2)CC[C@]1(O)c1ccc(Cl)cc1]

Methyl 3-((1R,2S)-2-((S)-4-(4-chlorophenyl)-4-hydroxy-3,3-dimethylpiperidine-1-carbonyl)cyclohexylcarbamoyl)benzoate (55 mg, 0.104 mmol) was dissolved in methanol (3 mL) at 25° C. with stirring and then 1.000 N NaOH (0.209 mL, 0.209 mmol) was added thereto. The mixture was stirred for 20 hours, diluted with water and then the MeOH was evaporated. The basic aqueous mixture was acidified to pH=3 with 1N HCl. The resulting solids were dissolved and extracted with methylene chloride (2×). The organic layers were combined, dried over sodium sulfate and concentrated to Example 4 (50 mg, 0.097 mmol, 93% yield) as a white glass. MS (ESI$^+$)=513.17 (M+H)$^+$. $^1$H NMR (CD$_3$OD, 400 MHz) (NMR shows several rotamers) δ 8.39 (m, 1H), 8.20 (d, 0.5H, J=8.0 Hz), 8.16 (d, 0.5H, J=8.0 Hz), 8.05 (d, 0.5H, J=8.0 Hz), 8.03 (d, 0.5H, J=8.0 Hz), 7.98 (d, 0.5H, J=8.0 Hz), 7.96 (d, 0.5H, J=8.0 Hz), 7.60 (app. t, 0.5H, J=8.0 Hz), 7.56 (app. t, 0.5H, J=8.0 Hz), 7.47 (d, 1H, J=8.0 Hz), 7.35 (d, 1H, J=8.0 Hz), 7.29 (d, 1H, J=8.0 Hz), 7.23 (d, 1H, J=8.0 Hz), 4.57 (m, 0.5H), 4.42 (m, 0.5H), 4.20 (m, 0.5H), 4.04-3.96 (m, 1H), 3.67-3.55 (m, 1H), 3.46-3.34 (m, 2H), 3.14-2.98 (m, 1H), 2.73 (m, 0.5H), 2.57-2.44 (m, 1H), 2.26-2.15 (m, 0.5H), 2.08-1.98 (m, 1H), 1.98-1.85 (m, 0.5H), 1.85-1.61 (m, 3.5H), 1.61-1.41 (m, 3.5H), 0.77 (s, 0.5×3H), 0.76 (s, 0.5×3H), 0.73 (s, 0.5×3H), 0.65 (s, 0.5×3H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=2.06 minutes.]

Example 5

Phenyl (1R,2S)-2-((S)-4-(4-chlorophenyl)-4-hydroxy-3,3-dimethylpiperidine-1-carbonyl)cyclohexylcarbamate

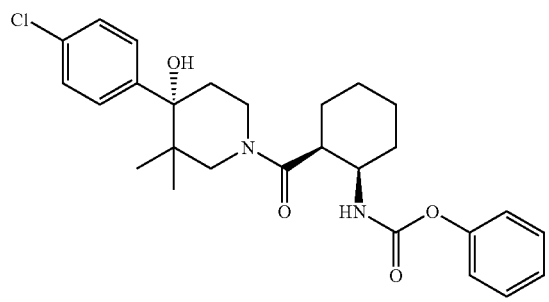 [SMILES: CC1(C)CN(C(=O)[C@H]2CCCC[C@H]2NC(=O)Oc2ccccc2)CC[C@]1(O)c1ccc(Cl)cc1]

((1S,2R)-2-Aminocyclohexyl)((S)-4-(4-chlorophenyl)-4-hydroxy-3,3-dimethylpiperidin-1-yl)methanone, HCl salt (250 mg, 0.623 mmol) (as described in Example 2, Step 1) and triethylamine (0.174 mL, 1.246 mmol) were dissolved in methylene chloride (10 mL) at RT with stirring, and then cooled to 0° C. A solution of methylene chloride and phenyl carbonochloridate (98 mg, 0.623 mmol) was added dropwise thereto. The reaction mixture was stirred for 1 hour, and then EtOAc was added. The resulting mixture was rinsed with 1N HCl (1×) and saturated sodium bicarbonate (1×). The organic layer was dried over sodium sulfate and concentrated to give a colorless oil. The colorless oil was purified over silica gel in 3:1 to 1:1 hexanes/EtOAc to 100% EtOAc to yield Example 5 (280 mg, 0.577 mmol, 93% yield) as a white glass. MS (ESI$^+$)=485.15 (M+H)$^+$.

Example 6

1-((1R,2S)-2-((S)-4-(4-Chlorophenyl)-4-hydroxy-3,3-dimethylpiperidine-1-carbonyl)cyclohexyl)-3-(2-hydroxy-2-methylpropyl)urea

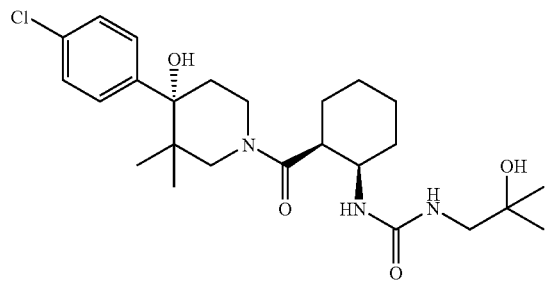

Example 5 (30 mg, 0.062 mmol), 1-amino-2-methylpropan-2-ol (5.51 mg, 0.062 mmol) and triethylamine (0.017 mL, 0.124 mmol) were mixed in acetonitrile (3 mL) at RT and then microwaved at 150° C. for 30 minutes. The solvent was evaporated. The resulting residue was then purified over silica gel in 100% EtOAc to 4:1 methylene chloride/MeOH to yield Example 6 (25 mg, 0.052 mmol, 84% yield) as a white glass. MS (ESI$^+$)=480.18 (M+H)$^+$. $^1$H NMR (CD$_3$OD, 400 MHz)

(NMR shows several rotamers) δ 7.43-7.34 (m, 2H), 7.22 (d, 2H, J=8.0 Hz), 6.15-5.95 (m, 1H), 4.50-4.40 (m, 0.5H), 4.10-3.95 (m, 1H), 3.90-3.75 (m, 1.5H), 3.66-3.44 (m, 1H), 3.15-3.02 (m, 2H), 3.02-2.90 (m, 2H), 2.64 (m, 0.5H), 2.47 (m, 0.5H), 2.15-205 (m, 0.5H), 1.80-1.69 (m, 1.5H), 1.69-1.30 (m, 7H), 1.07 (s, 6H), 0.76-0.62 (m, 6H). [LCMS method: Inj. Vol.=10 uL; Start % B=0; Final % B=100; Gradient Time=4 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=3.59 minutes.]

Example 7 tert-Butyl (1R,2S)-2-((S)-4-(4-chlorophenyl)-4-hydroxy-3,3-dimethylpiperidine-1-carbonyl)cyclopentylcarbamate

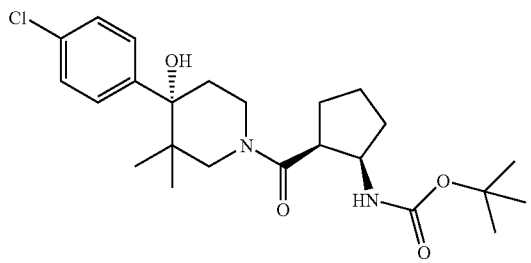 [SMILES: CC(C)(C)OC(=O)N[C@@H]1CCC[C@@H]1C(=O)N1CC[C@](O)(c2ccc(Cl)cc2)C(C)(C)C1]

Step 1: (1S,2R)-2-(tert-Butoxycarbonylamino)cyclopentanecarboxylic acid

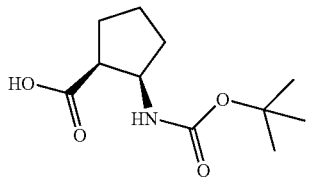 [SMILES: CC(C)(C)OC(=O)N[C@@H]1CCC[C@@H]1C(=O)O]

(1S,2R)-2-Aminocyclopentanecarboxylic acid, HCl (515 mg, 3.11 mmol) was dissolved in water (5.00 mL) at 25° C. with stirring and then KOH (349 mg, 6.22 mmol) was added. A solution of BOC-anhydride (0.722 mL, 3.11 mmol) in dioxane (5 mL) was then added and the reaction mixture was stirred for 20 hours. After this time, the reaction mixture was concentrated and the remaining aqueous phase was extracted with chloroform (3×). The chloroform extracts were combined, dried over sodium sulfate and concentrated to give (1S,2R)-2-(tert-butoxycarbonylamino)cyclopentanecarboxylic acid (550 mg, 2.399 mmol, 77% yield) as a viscous colorless oil. MS (ESI$^+$)=230.30 (M+H)$^+$.

Step 2: Example 7

(S)-4-(4-Chlorophenyl)-3,3-dimethylpiperidin-4-ol (105 mg, 0.436 mmol), (1S,2R)-2-(tert-butoxycarbonylamino)cyclopentanecarboxylic acid (100 mg, 0.436 mmol), HOBt (134 mg, 0.872 mmol), EDC (167 mg, 0.872 mmol) and triethylamine (0.304 mL, 2.181 mmol) were mixed in methylene chloride (15 mL) at 25° C. and stirred for 20 hours. The reaction was worked up by adding methylene chloride then rinsing with saturated sodium carbonate (1×). The methylene chloride layer was dried over sodium sulfate and concentrated to give a colorless oil. The colorless oil was purified over silica gel in 3:1 to 1:1 hexanes/EtOAc to 100% EtOAc to yield Example 7 (44 mg, 0.098 mmol, 22.37% yield) as a white glass. MS (ESI$^+$)=451.27 (M+H)$^+$. $^1$H NMR (CD$_3$OD, 500 MHz) (NMR shows several rotamers) δ 7.49-7.43 (m, 2H), 7.32-7.25 (m, 2H), 6.28 (m, 1H), 4.55 (m, 0.5H), 4.35 (m, 0.5H), 4.24 (m, 0.5H), 4.17 (m, 0.5H), 4.10-3.99 (m, 1.5), 3.67-3.32 (m, 2H), 3.17-3.02 (m, 1H), 2.80-2.66 (m, 0.5H), 2.62-2.53 (m, 0.5H), 2.15-1.90 (m, 2H), 1.90-1.74 (m, 2H), 1.74-1.47 (m, 3.5H), 1.44 (s, 0.5×9H), 1.43 (s, 0.5×9H), 0.84-0.68 (m, 6H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=2.03 minutes.]

Example 8

N-((1R,2S)-2-((S)-4-(4-Chlorophenyl)-4-hydroxy-3,3-dimethylpiperidine-1-carbonyl)cyclopentyl)benzamide

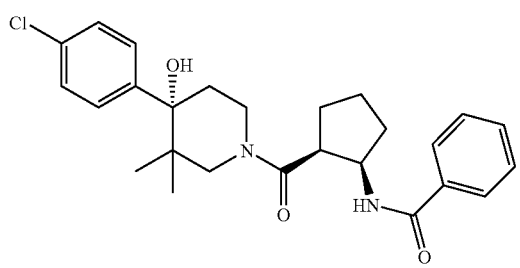 [SMILES: CC1(C)CN(C(=O)[C@H]2CCC[C@H]2NC(=O)c2ccccc2)CC[C@]1(O)c1ccc(Cl)cc1]

Step 1: ((1S,2R)-2-Aminocyclopentyl)((S)-4-(4-chlorophenyl)-4-hydroxy-3,3-dimethylpiperidin-1-yl)methanone

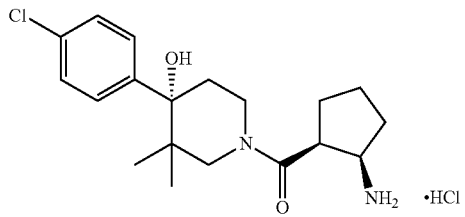 [SMILES: CC1(C)CN(C(=O)[C@H]2CCC[C@H]2N)CC[C@]1(O)c1ccc(Cl)cc1 ; Cl]

tert-Butyl (1R,2S)-2-((S)-4-(4-chlorophenyl)-4-hydroxy-3,3-dimethylpiperidine-1-carbonyl)cyclopentylcarbamate (180 mg, 0.399 mmol) was dissolved in dioxane (2 mL) at 25° C. with stirring and then 4N HCl in dioxane (0.499 mL, 1.996 mmol) was added and the resulting mixture was stirred for 3 hours. After this time, the reaction mixture was concentrated (5×) from methylene chloride to obtain ((1S,2R)-2-aminocyclopentyl)((S)-4-(4-chlorophenyl)-4-hydroxy-3,3-dimethylpiperidin-1-yl)methanone, HCl salt (150 mg, 0.387 mmol, 97% yield) as a white glass. MS (ESI$^+$)=351.21 (M+H)$^+$.

Step 2: Example 8

((1S,2R)-2-Aminocyclopentyl)((S)-4-(4-chlorophenyl)-4-hydroxy-3,3-dimethylpiperidin-1-yl)methanone, HCl (35 mg, 0.090 mmol), benzoic acid (11.03 mg, 0.090 mmol), HOBt (27.7 mg, 0.181 mmol), EDC (34.6 mg, 0.181 mmol) and triethylamine (0.063 mL, 0.452 mmol) were mixed in methylene chloride (3 mL) at 25° C. and stirred for 3 days. At the conclusion of this period, the reaction was worked up by adding methylene chloride and then rinsing with saturated sodium carbonate (1×). The methylene chloride layer was dried over sodium sulfate and concentrated to give a colorless oil. The colorless oil was purified by preparative HPLC/MS to yield Example 8 (22 mg, 0.039 mmol, 42.8% yield) as a white solid. MS (ESI$^+$)=455.08 (M+H)$^+$. $^1$H NMR (CD$_3$OD, 500 MHz) (NMR shows several rotamers) δ 7.90 (d, 0.5H, J=8.0 Hz), 7.80 (d, 0.5H, J=8.0 Hz), 7.76-7.72 (m, 1H), 7.58-7.40 (m, 4H), 7.35-7.22 (m, 2H), 7.19 (s, 1H), 4.84-4.48 (m, 1H), 4.13-3.98 (m, 1.5H), 3.63-3.50 (m, 3.5H), 3.17-2.97 (m, 0.5H), 2.97-2.85 (m, 1H), 2.70-2.37 (m, 1H), 2.26-2.01 (m, 2H), 2.01-1.91 (m, 2.5H), 1.91-1.80 (m, 1H), 1.73-1.59 (m, 1H), 1.54-1.40 (m, 1H), 0.83-0.65 (m, 6H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=1.96 minutes.]

Example 9

1-((1R,2S)-2-((S)-4-(4-Chlorophenyl)-4-hydroxy-3,3-dimethylpiperidine-1-carbonyl)cyclopentyl)-3-phenylurea

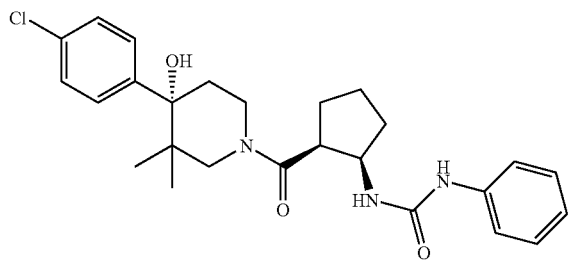 [SMILES: CC1(C)CN(C(=O)[C@H]2CCC[C@H]2NC(=O)Nc2ccccc2)CC[C@]1(O)c1ccc(Cl)cc1]

((1S,2R)-2-Aminocyclopentyl)((S)-4-(4-chlorophenyl)-4-hydroxy-3,3-dimethylpiperidin-1-yl)methanone, HCl salt (25 mg, 0.065 mmol) was stirred in THF (3 mL) at 25° C. Triethylamine (0.018 mL, 0.129 mmol) was added thereto followed by phenyl isocyanate (7.05 µl, 0.065 mmol). The mixture was stirred for 1 hour. The reaction was then concentrated and purified by preparatory HPLC/MS to yield Example 9 (20 mg, 0.034 mmol, 53% yield) as a white solid. MS (ESI$^+$)=470.26 (M+H)$^+$. $^1$H NMR (CD$_3$OD, 500 MHz) (NMR shows several rotamers) δ 7.37 (d, 1H, J=8 Hz), 7.28-7.09 (m, 7H), 6.92-6.84 (m, 1H), 4.47 (m, 0.5H), 4.37 (m, 1H), 4.23 (m, 0.5H), 3.97 (m, 1.5H), 3.54-3.33 (m, 2.5H), 3.09-2.91 (m, 1H), 2.61 (m, 1H), 2.09-1.98 (m, 1H), 1.98-1.71 (m, 4H), 1.66-1.48 (m, 2H), 1.46-1.33 (m, 1H), 0.71-0.63 (m, 6H). [LCMS method: Inj. Vol.=10 uL; Start % B=0; Final % B=100; Gradient Time=2 min; Flow Rate=5 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire S5 C18 4.6×50 mm (2 min. grad); Retention Time=1.96 minutes.]

Example 10

N-((7S,8R)-7-((S)-4-(4-Chlorophenyl)-4-hydroxy-3,3-dimethylpiperidine-1-carbonyl)-1,4-dioxaspiro[4.5]decan-8-yl)benzamide

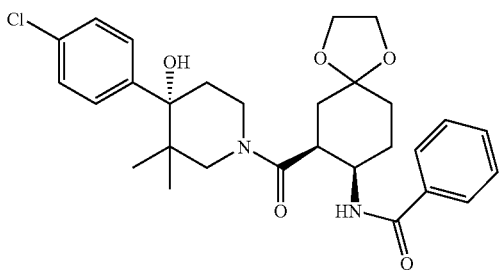 [SMILES: CC1(C)CN(C(=O)[C@H]2CC3(CC[C@H]2NC(=O)c2ccccc2)OCCO3)CC[C@]1(O)c1ccc(Cl)cc1]

Step 1: (7S,8R)-Ethyl 8-((R)-1-phenylethylamino)-1,4-dioxaspiro[4.5]decane-7-carboxylate

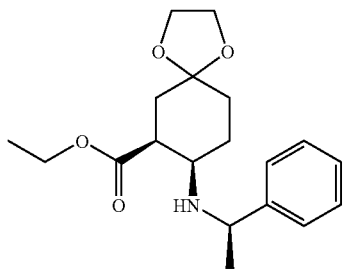 [SMILES: CCOC(=O)[C@H]1CC2(CC[C@H]1N[C@H](C)c1ccccc1)OCCO2]

5% Pt/C (Sigma-Aldrich catalog #205931, 0.80 g, 30.2 mmol) was carefully wetted down under argon with ethanol. Acetic acid (5.30 mL, 93 mmol) was added thereto followed by (R)-ethyl 8-(1-phenylethylamino)-1,4-dioxaspiro[4.5]dec-7-ene-7-carboxylate (prepared in a similar manner as that described in International Patent Application No. WO 2005/048932, 10.0 g, 30.2 mmol) in ethanol (50 mL). The reaction was then hydrogenated at 50 psi for about 16 hours with stirring in a Parr Shaker apparatus. The catalyst was carefully filtered under argon and the filtrate concentrated to yield an amber oil. The oil was dissolved in EtOAc then rinsed with 5% Na$_2$HPO$_4$ until pH=8-9 (5 rinses). The EtOAc layer was dried over sodium sulfate and concentrated to give (7S,8R)-ethyl 8-((R)-1-phenylethylamino)-1,4-dioxaspiro[4.5]decane-7-carboxylate (5.40 g, 16.2 mmol, 54% yield) as an amber oil. MS (ESI$^+$)=334.25 (M+H)$^+$.

Step 2: (7S,8R)-Ethyl 8-((R)-1-phenylethylamino)-1,4-dioxaspiro[4.5]decane-7-carboxylate, p-TsOH salt

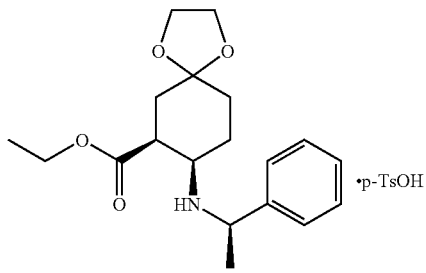 [SMILES: CCOC(=O)[C@H]1CC2(CC[C@H]1N[C@H](C)c1ccccc1)OCCO2]

(7S,8R)-Ethyl 8-((R)-1-phenylethylamino)-1,4-dioxaspiro[4.5]decane-7-carboxylate (7.80 g, 23.39 mmol) was dissolved in ethyl acetate (40 mL) at 25° C. with stirring. Et₂O (40 mL) was then added followed by the addition of p-toluenesulfonic acid-monohydrate (4.45 g, 23.39 mmol) in one portion. Precipitation occurred almost immediately. The mixture was stirred for ½ hour, after which the precipitate was collected by filteration. The solids were rinsed with Et₂O and then dried under high vacuum to yield (7S,8R)-ethyl 8-((R)-1-phenylethylamino)-1,4-dioxaspiro[4.5]decane-7-carboxylate, p-toluenesulfonic acid (10.3 g, 20.37 mmol, 87% yield) as an off-white solid. MS (ESI⁺)=334.30 (M+H)⁺.

Step 3: (7S,8R)-Ethyl 8-amino-1,4-dioxaspiro[4.5]decane-7-carboxylate, p-toluenesulfonic acid salt

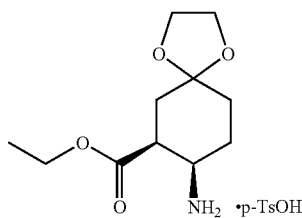 [SMILES: CCOC(=O)[C@H]1CC2(CC[C@H]1N)OCCO2]

10% Pd/C (Degussa, 50% wet, 1.0 g, 9.40 mmol) was carefully wetted down under argon with ethanol, and then (7S,8R)-ethyl 8-((R)-1-phenylethylamino)-1,4-dioxaspiro[4.5]decane-7-carboxylate p-toluenesulfonic acid salt (10.3 g, 20.37 mmol) in ethanol (75 mL) was added. The mixture was then hydrogenated on a Parr Shaker apparatus for about 16 hours at 50 psi. Under argon, the reaction was carefully filtered through a fiberglass filter paper. The filtrate was concentrated to give (7S,8R)-ethyl 8-amino-1,4-dioxaspiro[4.5]decane-7-carboxylate p-toluenesulfonic acid salt (8.10 g, 20.18 mmol, 99% yield) as a tacky white glass. MS (ESI⁺)=230.12 (M+H)⁺.

Step 4: (7S,8R)-Ethyl 8-benzamido-1,4-dioxasoiro[4.5]decane-7-carboxylate

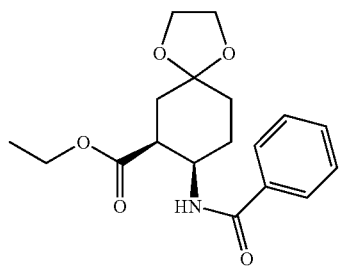 [SMILES: CCOC(=O)[C@H]1CC2(CC[C@H]1NC(=O)c1ccccc1)OCCO2]

(7S,8R)-Ethyl 8-amino-1,4-dioxaspiro[4.5]decane-7-carboxylate, p-toluenesulfonic acid salt (1.0 g, 2.491 mmol), benzoic acid (0.304 g, 2.491 mmol), HOBt (0.458 g, 2.99 mmol), EDC (0.573 g, 2.99 mmol) and triethylamine (0.694 mL, 4.98 mmol) were mixed in acetonitrile (20 mL) at 25° C. and stirred for 20 hours. The acetonitrile was concentrated to give a light colored oil. The oil was dissolved in methylene chloride and washed with saturated sodium carbonate (1×). The methylene chloride layer was dried over sodium sulfate and concentrated to give a colorless oil. The colorless oil was purified over silica gel in 3:1 to 1:1 hexanes/EtOAc to 100% EtOAc to yield (7S,8R)-ethyl 8-benzamido-1,4-dioxaspiro[4.5]decane-7-carboxylate (740 mg, 2.22 mmol, 99% yield). MS (ESI⁺)=334.25 (M+H)⁺.

Step 5: (7S,8R)-8-Benzamido-1,4-dioxaspiro[4.5]decane-7-carboxylic acid

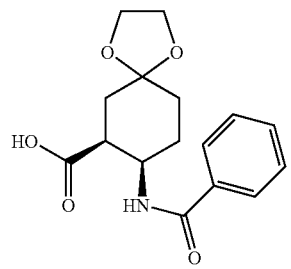 [SMILES: O=C(N[C@@H]1CCC2(C[C@@H]1C(=O)O)OCCO2)c1ccccc1]

(7S,8R)-Ethyl 8-benzamido-1,4-dioxaspiro[4.5]decane-7-carboxylate (740 mg, 2.22 mmol) was dissolved in THF (10 mL) at 25° C. with stirring. 0.5N LiOH (8.88 mL, 4.44 mmol) was then added thereto and the mixture stirred for 3 hours. The reaction was worked up by adding water and then removing the THF in vacuo. The remaining basic aqueous mixture was then acidified to pH=3 with 1N HCl. The aqueous mixture was extracted (2×) with methylene chloride. The methylene chloride extracts were combined, dried over sodium sulfate and concentrated to give (7S,8R)-8-benzamido-1,4-dioxaspiro[4.5]decane-7-carboxylic acid (678 mg, 2.22 mmol, 100% yield) as a white glass. MS (ESI⁺)=306.19 (M+H)⁺.

Step 6: Example 10

(S)-4-(4-Chlorophenyl)-3,3-dimethylpiperidin-4-ol (25 mg, 0.104 mmol), (7S,8R)-8-benzamido-1,4-dioxaspiro[4.5]decane-7-carboxylic acid (31.8 mg, 0.104 mmol), HOBt (19.16 mg, 0.125 mmol), EDC (23.99 mg, 0.125 mmol) and triethylamine (0.029 mL, 0.209 mmol) were mixed in methylene chloride (3 mL) at 25° C. and stirred for 20 hours. The reaction was worked up by adding methylene chloride followed by rinsing with saturated sodium carbonate (1×). The methylene chloride layer was dried over sodium sulfate and concentrated to give a colorless oil. The colorless oil was purified over silica gel in 3:1 to 1:1 hexanes/EtOAc to 100% EtOAc to 9:1 methylene chloride/methanol to yield Example 10 (28 mg, 0.053 mmol, 51% yield) as a white solid. MS (ESI⁺)=527.17 (M+H)⁺. ¹H NMR (CD₃OD, 400 MHz) (NMR shows several rotamers) δ 7.81 (d, 0.5H, J=8.0 Hz), 7.74 (d, 1.5H, J=8.0 Hz), 7.60-7.40 (m, 5H), 7.33-7.25 (m, 2H), 4.62-4.55 (m, 0.5H), 4.55-4.47 (m, 0.5H), 4.34-4.27 (m, 0.5H), 4.07-3.91 (m, 7H), 3.78-3.67 (m, 0.5H), 3.67-3.58 (m, 0.5H), 3.54-3.38 (m, 1.5H), 3.16-2.98 (m, 1H), 2.82-2.70 (m, 0.5H), 2.62-2.50 (m, 0.5H), 2.40-2.19 (m, 1.5H), 2.11-1.97 (m, 1.5H), 1.97-1.44 (m, 5H), 0.86-0.71 (m, 6H). [LCMS method: Inj. Vol.=10 uL; Start % B=0; Final % B=100; Gradient Time=2 min; Flow Rate=5 ml/min; Wavelength=220 nm; Solvent A=10% MeOH-90% H₂O-0.1% TFA; Solvent B=90% MeOH-10% H₂O-0.1% TFA; Column 1=Waters Sunfire S5 C18 4.6×50 mm (2 min. grad); Retention Time=1.93 minutes.]

Example 11

N-((1R,2S)-2-((S)-4-(4-Chlorophenyl)-4-hydroxy-3,3-dimethylpiperidine-1-carbonyl)-4-oxocyclohexyl)benzamide

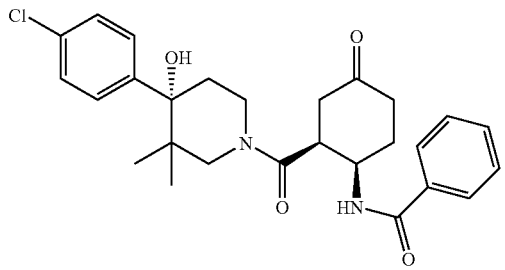 [SMILES: CC1(C)CN(C(=O)[C@H]2CC(=O)CC[C@H]2NC(=O)c2ccccc2)CC[C@]1(O)c1ccc(Cl)cc1]

Step 1:
(1S,2R)-2-Benzamido-5-oxocyclohexanecarboxylic acid

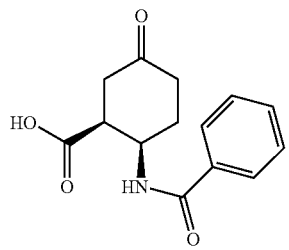 [SMILES: O=C1CC[C@@H](NC(=O)c2ccccc2)[C@@H](C(=O)O)C1]

(7S,8R)-8-Benzamido-1,4-dioxaspiro[4.5]decane-7-carboxylic acid (750 mg, 2.456 mmol) was dissolved in acetonitrile (10 mL) at 25° C. with stirring. 1N HCl (12.28 mL, 12.28 mmol) was then added thereto and the reaction stirred at 25° C. for about 16 hours. The reaction was concentrated to remove the acetonitrile. White solids precipitated and ethyl acetate and THF were added to dissolve the solids. The resulting mixture was rinsed (3×) with water. The organic layer was dried over sodium sulfate and concentrated to give (1S,2R)-2-benzamido-5-oxocyclohexanecarboxylic acid (430 mg, 1.646 mmol, 67.0% yield) as a white solid. MS (ESI⁺)=262.11 (M+H)⁺.

Step 2: Example 11

(S)-4-(4-Chlorophenyl)-3,3-dimethylpiperidin-4-ol (262 mg, 1.091 mmol), (1S,2R)-2-benzamido-5-oxocyclohexanecarboxylic acid (285 mg, 1.091 mmol), HOBt (200 mg, 1.309 mmol), EDC (251 mg, 1.309 mmol) and triethylamine (0.304 mL, 2.182 mmol) were mixed in methylene chloride (3 mL) at 25° C. and stirred for 3 hours. After this time, the reaction was worked up by adding methylene chloride and then rinsing with saturated sodium carbonate (1×). The methylene chloride layer was dried over sodium sulfate and concentrated to give an off-white glass. The off-white glass was purified over silica gel in 1:1 hexanes/EtOAc to 100% EtOAc to yield Example 11 (430 mg, 0.89 mmol, 82% yield) as a white solid. MS (ESI⁺)=483.15 (M+H)⁺. ¹H NMR (CD₃OD, 400 MHz) (NMR shows several rotamers) δ 7.84 (d, 2H, J=8.0 Hz), 7.59-7.39 (m, 6H), 7.39-7.30 (m, 1H), 7.27 (d, 2H, J=8.0 Hz), 4.70-4.60 (m, 1H), 4.21-4.14 (m, 1H), 4.06-3.98 (m, 1H), 3.94-3.85 (m, 1H), 3.58-3.34 (m, 1H), 3.11-3.04 (m, 1H), 2.75-2.60 (m, 2H), 2.60-2.49 (m, 3H), 2.41-2.31 (m, 0.5H), 2.10-2.01 (m, 0.5H), 1.51-1.36 (m, 1H), 1.28-1.20 (m, 0.5H), 0.75 (s, 3H), 0.72 (s, 3H). [LCMS method: Inj. Vol.=10 uL; Start % B=0; Final % B=100; Gradient Time=2 min; Flow Rate=5 ml/min; Wavelength=220 nm; Solvent A=10% MeOH-90% H₂O-0.1% TFA; Solvent B=90% MeOH-10% H₂O-0.1% TFA; Column 1=Waters Sunfire S5 C18 4.6×50 mm (2 min. grad); Retention Time=1.76 minutes.]

Example 12

N-((1R,2S)-2-((S)-4-(4-Chlorophenyl)-4-hydroxy-3,3-dimethylpiperidine-1-carbonyl)-4-(methylamino)cyclohexyl)benzamide, TFA salt

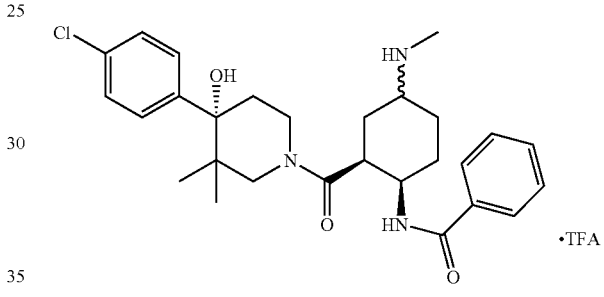

N-((1R,2S)-2-((S)-4-(4-Chlorophenyl)-4-hydroxy-3,3-dimethylpiperidine-1-carbonyl)-4-oxocyclohexyl)benzamide (30 mg, 0.062 mmol) was dissolved in methylene chloride (3 mL) at 25° C. with stirring and then 2.0 M monomethylamine in THF (0.155 mL, 0.311 mmol) was added thereto. The mixture was stirred for 3 hours. Powdered 4A molecular sieves and 2.0 M monomethylamine in THF (0.155 mL, 0.311 mmol) were added thereto and stirred for about 16 hours in a sealed vial. Sodium triacetoxyborohydride (19.75 mg, 0.093 mmol) was then added and the contents stirred for an additional 20 hours. The product was purified by preparatory HPLC/MS to yield Example 12 (7.0 mg, 0.011 mmol, 18% yield). MS (ESI⁺)=498.17 (M+H)⁺. ¹H NMR (CD₃OD, 400 MHz) (NMR shows several rotamers) δ 7.75-7.65 (m, 2H), 7.52-7.31 (m, 6H), 7.23-7.10 (m 2H), 4.39-4.34 (m, 0.5H), 4.04-3.88 (m, 1H), 3.54.3.37 (m, 1H), 3.30-3.23 (m, 3H), 3.05-2.90 (m, 2H), 2.66-2.56 (m, 4H), 2.11-1.99 (m, 1H), 1.79-1.64 (m, 0.5H), 1.48-1.28 (m, 1H), 0.68-0.64 (m, 6H). [LCMS method: Inj. Vol.=10 uL; Start % B=0; Final % B=100; Gradient Time=4 min; Flow Rate=4 ml/min; Wavelength=220 nm; Solvent A=10% MeOH-90% H₂O-0.1% TFA; Solvent B=90% MeOH-10% H₂O-0.1% TFA; Column 1=Waters Sunfire C18 4.6×50 mm (4 min. grad); Retention Time=3.59 minutes.]

Example 13

N-((1R,2S)-2-((S)-4-(4-Chlorophenyl)-4-hydroxy-3,3-dimethylpiperidine-1-carbonyl)-4-hydroxycyclohexyl)benzamide

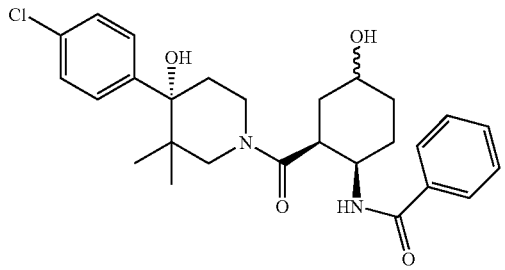

N-((1R,2S)-2-((S)-4-(4-Chlorophenyl)-4-hydroxy-3,3-dimethylpiperidine-1-carbonyl)-4-oxocyclohexyl)benzamide (30 mg, 0.062 mmol) was dissolved in MeOH (2 mL) at 25° C. with stirring and then NaBH$_4$ (2.350 mg, 0.062 mmol) was added. The mixture was stirred for 20 hours. The MeOH was removed in vacuo and then 1 N HCl was added. The aqueous mixture was extracted (2×) with methylene chloride. The organic layers were combined, dried over sodium sulfate and concentrated to give Example 13 (28 mg, 0.058 mmol, 93% yield) as a white solid. MS (ESI$^+$)=485.33 (M+H)$^+$. $^1$H NMR (CD$_3$OD, 400 MHz) (NMR shows several rotamers) δ 8.10-7.89 (m, 1H), 7.89-7.68 (m, 2H), 7.64-7.39 (m, 5H), 7.39-7.22 (m, 2H), 4.60-4.37 (m, 1H), 4.25-4.17 (m, 0.5H), 4.09-3.97 (m, 2H), 3.83-3.43 (m, 3H), 3.18-2.99 (m, 1H), 2.81-2.67 (m, 1H), 2.62-2.44 (m, 0.5H), 2.42-2.30 (m, 0.5H), 2.22-2.10 (m, 1H), 2.04-1.38 (m, 5.5H), 1.33-1.05 (m, 1H), 0.90-0.65 (m, 6H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.08 minutes.]

Example 14

Methyl 5-((1R,2S)-2-((S)-4-(4-chlorophenyl)-4-hydroxy-3,3-dimethylpiperidine-1-carbonyl)cyclohexylcarbamoyl)biphenyl-3-carboxylate

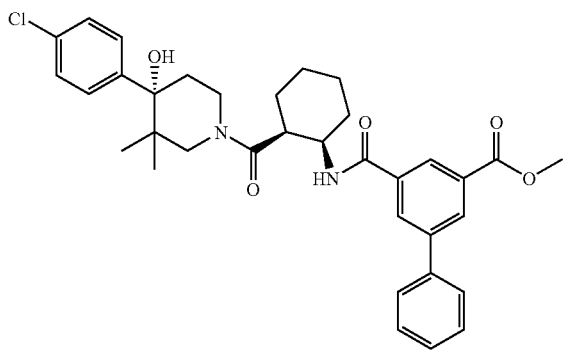 [SMILES: COC(=O)c1cc(C(=O)N[C@@H]2CCCC[C@@H]2C(=O)N2CC[C@](O)(c3ccc(Cl)cc3)C(C)(C)C2)cc(-c2ccccc2)c1]

Step 1: Preparation of 3-amino-5-(methoxycarbonyl)benzoic acid

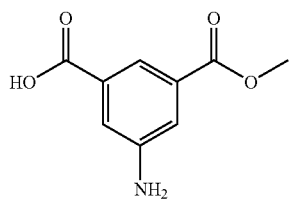

20% Pd(OH)$_2$ (0.50 g) was carefully wetted down under argon with methanol (5 mL) and then 3-(methoxycarbonyl)-5-nitrobenzoic acid (5.00 g, 22.2 mmol) in methanol (20 mL) was added. The mixture was then hydrogenated on a Parr Shaker apparatus for 5 hours at 50 psi. Under argon, the reaction was carefully filtered through a fiberglass filter paper. The filtrate was concentrated to give 3-amino-5-(methoxycarbonyl)benzoic acid (4.0 g, 20.5 mmol, 92% yield) of off-white solids as product. MS found: (M−H)$^+$=194.

Step 2: Preparation of 3-bromo-5-(methoxycarbonyl)benzoic acid

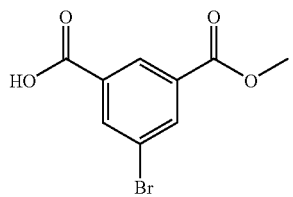

3-Amino-5-(methoxycarbonyl)benzoic acid (1.0 g, 5.12 mmol, 1 eq.) was dissolved in 15% HBr (22.5 mL) at RT, then cooled to 0° C. with stirring. A 2.5 M aqueous solution of NaNO$_2$ (2.3 mL, 5.64 mmol, 1.1 eq.) was added slowly via an addition funnel to generate the diazonium salt. In a separate flask, CuBr was partially dissolved in 15% HBr (9 mL) and cooled to 0° C. with stirring, to which the diazonium salt solution was subsequently added. A slight exotherm was observed. The reaction was stirred at RT for 30 minutes then carefully heated at 70° C. for 1 hour. The reaction was worked up by filtering off insoluble material as crude product. The solids were dissolved in water/EtOAc and the layers separated. The aqueous layer was extracted again with EtOAc. The organic layers were combined, dried over sodium sulfate and concentrated to give an off-white solid. The product was purified over silica gel in 1:1 hexanes/EtOAc to 100% EtOAc to 4:1 methylene chloride/MeOH to yield 3-bromo-5-(methoxycarbonyl)benzoic acid (0.90 g, 3.47 mmol, 68% yield) as a white solid. MS found: (M−H)$^+$=257/259.

Step 3: Preparation of 5-(methoxycarbonyl)biphenyl-3-carboxylic acid

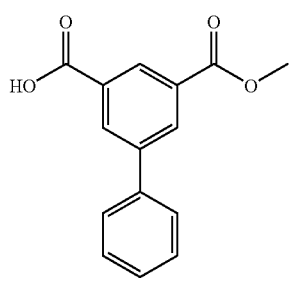

3-Bromo-5-(methoxycarbonyl)benzoic acid (100 mg, 0.386 mmol, 1 equiv.), phenyl boronic acid (47 mg, 0.386 mmol, 1 equiv.), and Pd(OAc)$_2$ (3 mg, 0.0012 mmol, 0.03 equiv.) were mixed in DMF (2 mL) at RT with stirring, followed by 1.5 M cesium carbonate (0.77 mL, 1.16 mmol, 3 equiv.). The mixture was heated at 40° C. for 3 hours. The reaction was worked up by adding water and adjusting the pH to 3 with 1N HCl. The aqueous layer was extracted (3×) with EtOAc/THF. The organic layers were combined, dried over sodium sulfate and concentrated to give 140 mg of an off-white solid. The product was purified over silica gel in 3:1 to 1:1 hexanes/EtOAc to 100% EtOAc to yield 5-(methoxycarbonyl)biphenyl-3-carboxylic acid (40 mg, 0.156 mmol, 40% yield) as a white solid. MS found: (M−H)$^+$=255.

Step 4: Example 14

((1S,2R)-2-Aminocyclohexyl)((S)-4-(4-chlorophenyl)-4-hydroxy-3,3-dimethylpiperidin-1-yl)methanone, HCl (50 mg, 0.125 mmol), 5-(methoxycarbonyl)biphenyl-3-carboxylic acid (31.9 mg, 0.125 mmol), HOBt (22.89 mg, 0.149 mmol), EDC (28.7 mg, 0.149 mmol) and triethylamine (0.035 mL, 0.249 mmol) were mixed and stirred in methylene chloride (3 mL) at 25° C. for 20 hours. The reaction was worked up by adding methylene chloride then rinsing with saturated sodium carbonate (1×). The methylene chloride layer was dried over sodium sulfate and concentrated to give a colorless oil. The colorless oil was purified over silica gel in 3:1 to 1:1 hexanes/EtOAc to 100% EtOAc to yield Example 14 (48 mg, 0.080 mmol, 63.9% yield) as a white glass. MS (ESI$^+$)=603.38 (M+H)$^+$. $^1$H NMR (CD$_3$OD, 400 MHz) (NMR shows several rotamers) δ 8.22 (s, 1H), 7.93-7.82 (m, 1H), 7.76 (app. t, 1H, J=8 Hz), 7.48 (d, 2H, J=8.0 Hz), 7.36 (d, 2H, J=8.0 Hz), 7.30 (d, 2H, J=8.0 Hz), 7.23 (d, 2H, J=8.0 Hz), 4.62-4.53 (m, 0.5H), 4.49-4.40 (m, 0.5H), 4.26-4.16 (m, 0.5H), 4.06-4.00 (m, 1H), 3.97 (s, 0.5×3H), 3.95 (s, 0.5×3H), 3.70-3.52 (m, 1H), 3.50-3.34 (m, 1H), 3.16-2.97 (m, 1H), 2.80-2.68 (m, 0.5H), 2.58-2.40 (m, 1H), 2.33-2.01 (m, 0.5H), 1.98-1.86 (m, 0.5H), 1.86-1.61 (m, 4H), 1.61-1.37 (m, 6H), 1.33-1.15 (m, 2H), 0.79 (s, 0.5×3H), 0.77 (s, 0.5×3H), 0.74 (s, 0.5×3H), 0.66 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.46 minutes.]

Example 15

Preparation of 5-((1R,2S)-2-((S)-4-(4-chlorophenyl)-4-hydroxy-3,3-dimethylpiperidine-1-carbonyl)cyclohexylcarbamoyl)biphenyl-3-carboxylic acid

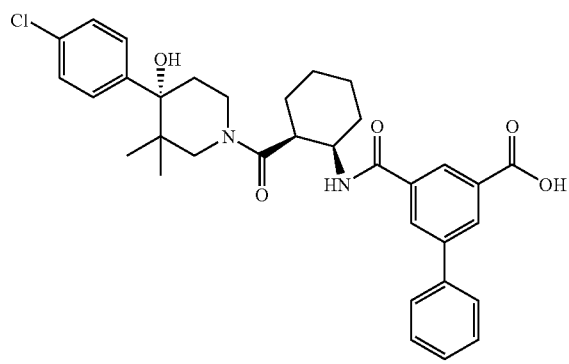 [SMILES: CC1(C)CN(C(=O)[C@H]2CCCC[C@H]2NC(=O)c2cc(C(=O)O)cc(-c3ccccc3)c2)CC[C@]1(O)c1ccc(Cl)cc1]

Example 14 was dissolved in methanol (3 mL) at 25° C. with stirring then 1.000 N NaOH (0.133 mL, 0.133 mmol) was added. The mixture was stirred for 20 hours. After this time, the reaction was worked up by adding water and then removing the MeOH in vacuo. The basic aqueous mixture was acidified to pH=3 with 1N HCl. The resulting precipitated solids were dissolved in methylene chloride and the aqueous and organic layers were separated. The aqueous layer was extracted once more with methylene chloride. The organic layers were combined, dried over sodium sulfate and concentrated to Example 15 (35 mg, 0.059 mmol, 90% yield) as a white solid. MS (ESI$^+$)=589.29 (M+H)$^+$. $^1$H NMR (CD$_3$OD, 400 MHz) (NMR shows several rotamers) δ 8.14 (t, 2H, J=8 Hz), 8.09-8.00 (m, 2H), 7.94-7.64 (m, 4H), 7.64-7.54 (m, 1H), 7.47 (d, 1H, J=8.0 Hz), 7.30 (d, 1H, J=8.0 Hz), 7.22 (d, 1H, J=8.0 Hz), 7.15 (d, 1H, J=8.0 Hz), 4.60-4.54 (m, 0.5H), 4.50-4.40 (m, 0.5H), 4.27-4.17 (m, 0.5H), 4.06-3.97 (m, 1H), 3.70-3.55 (m, 1.5H), 3.50-3.34 (m, 1H), 3.16-2.97 (m, 1H), 2.80-2.68 (m, 0.5H), 2.58-2.30 (m, 1H), 2.25-2.15 (m, 0.5H), 2.12-2.00 (m, 0.5H), 1.86-1.64 (m, 3.5H), 1.64-1.33 (m, 3.5H), 1.35-1.24 (m, 1H), 0.77 (app. s, 3H), 0.74 (s, 0.5×3H), 0.64 (s, 0.5×3H). [LCMS method: Inj. Vol.=10 uL; Start % B=0; Final % B=100; Gradient Time=2 min; Flow Rate=4 ml/min; Wavelength=220; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.45 minutes.]

Example 16

Preparation of methyl 3'-((1R,2S)-2-((S)-4-(4-chlorophenyl)-4-hydroxy-3,3-dimethylpiperidine-1-carbonyl)cyclohexylcarbamoyl)biphenyl-3-carboxylate

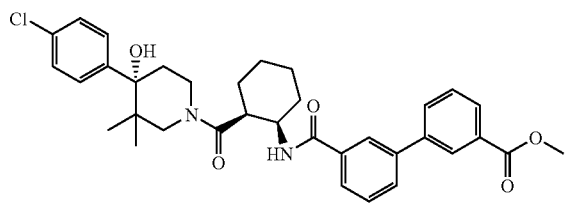 [SMILES: COC(=O)c1cccc(-c2cccc(C(=O)N[C@@H]3CCCC[C@@H]3C(=O)N3CC[C@](O)(c4ccc(Cl)cc4)C(C)(C)C3)c2)c1]

Step 1: Preparation of 3'-(methoxycarbonyl)biphenyl-3-carboxylic acid

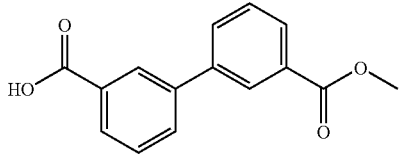 [SMILES: COC(=O)c1cccc(-c2cccc(C(=O)O)c2)c1]

3-Iodobenzoic acid (1.0 g, 4.03 mmol, 1 equiv.), 3-(methoxycarbonyl)phenylboronic acid (0.73 g, 4.03 mmol, 1 equiv.), and Pd(OAc)$_2$ (27 mg, 0.12 mmol, 0.03 equiv.) were mixed in DMF (10 mL) at RT with stirring, followed by the addition of 1.5M cesium carbonate (8.06 mL, 1.16 mmol, 3 equiv.). The mixture was heated at 40° C. for 4 hours. At the conclusion of this period, the reaction was worked up by adding water and adjusting the pH to 3 with 1N HCl. The aqueous mixture was extracted (3×) with EtOAc/THF. The organic layers were rinsed (3×) with water. The organic layer was dried over sodium sulfate and concentrated to give an off-white solid. The solid was stirred in hexanes (10 mL), filtered and dried under high vacuum to give 3'-(methoxycarbonyl)biphenyl-3-carboxylic acid (860 mg, 3.36 mmol, 83% yield) as a white solid. MS (ESI$^+$)=257.23 (M+H)$^+$.

Step 2: Example 16

((1S,2R)-2-Aminocyclohexyl)((S)-4-(4-chlorophenyl)-4-hydroxy-3,3-dimethylpiperidin-1-yl)methanone, HCl (50 mg, 0.125 mmol), 3'-(methoxycarbonyl)biphenyl-3-carboxylic acid (31.9 mg, 0.125 mmol), HOBt (22.89 mg, 0.149 mmol), EDC (28.7 mg, 0.149 mmol) and triethylamine (0.035 mL, 0.249 mmol) were mixed in methylene chloride (3 mL) at 25° C. and stirred for 20 hours. At the conclusion of this period, the reaction was worked up by adding methylene chloride then rinsing with saturated sodium carbonate (1×). The methylene chloride layer was dried over sodium sulfate and concentrated to give a colorless oil. The oil was purified over silica gel in 3:1 to 1:1 hexanes/EtOAc to 100% EtOAc to yield Example 16 (60 mg, 0.099 mmol, 80% yield) as a white solid. MS (ESI$^+$)=603.33 (M+H)$^+$. $^1$H NMR (CD$_3$OD, 400 MHz) (NMR shows several rotamers) δ 8.36 (s, 0.5H), 8.32 (s, 0.5H), 8.15-7.75 (m, 5H), 7.67-7.54 (m, 2H), 7.47 (d, 1H, J=8.0 Hz), 7.30 (d, 1H, J=8.0 Hz), 7.14 (d, 1H, J=8.0 Hz), 7.09 (d, 1H, J=8.0 Hz), 4.62-4.53 (m, 0.5H), 4.50-4.41 (m, 0.5H), 4.27-4.17 (m, 0.5H), 4.14-3.98 (m, 1H), 3.94 (s, 1.5H), 3.92 (s, 1.5H), 3.71-3.53 (m, 1H), 3.48-3.33 (m, 1.5H), 3.16-2.96 (m, 1H), 2.73 (m, 0.5H), 2.58-2.44 (m, 0.5H), 2.35 (m, 0.5H), 2.26-2.16 (m, 0.5H), 2.16-2.01 (m, 1H), 1.98-1.65 (m, 4H), 1.65-1.33 (m, 4H), 0.77 (app. s, 3H), 0.75 (s, 0.5×3H), 0.63 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.45 minutes.]

Example 17

Preparation of 3'-((1R,2S)-2-((S)-4-(4-chlorophenyl)-4-hydroxy-3,3-dimethylpiperidine-1-carbonyl)cyclohexylcarbamoyl)biphenyl-3-carboxylic acid

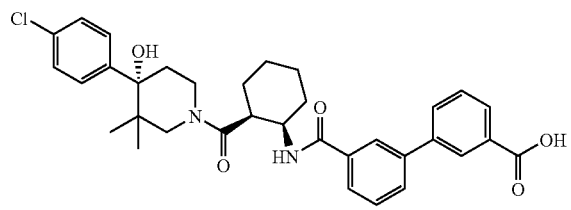 [SMILES: CC1(C)CN(C(=O)[C@H]2CCCC[C@H]2NC(=O)c2cccc(-c3cccc(C(=O)O)c3)c2)CC[C@]1(O)c1ccc(Cl)cc1]

Example 16 (55 mg, 0.091 mmol) was dissolved in methanol (3 mL) at 25° C. with stirring and then 1.000 N NaOH (0.182 mL, 0.182 mmol) was added. The mixture was stirred for 20 hours. After this time, the reaction was worked up by adding water and then removing the MeOH in vacuo. The basic aqueous mixture was acidified to pH=3 with 1N HCl. The precipitated solids were dissolved in methylene chloride and the aqueous and organic layers were separated. The aqueous layer was extracted once more with methylene chloride. The organic layers were combined, dried (sodium sulfate) and concentrated to give Example 17 (45 mg, 0.076 mmol, 84% yield) as a white solid. MS (ESI$^+$)=589.36 (M+H)$^+$. $^1$H NMR (CD$_3$OD, 400 MHz) (NMR shows several rotamers) δ 8.38 (s, 0.5H), 8.33 (s, 0.5H), 8.17-7.74 (m, 6H), 7.67-7.54 (m, 2H), 7.47 (d, 1H, J=8.0 Hz), 7.0 (d, 1H, J=8.0 Hz), 7.19 (d, 1H, J=8.0 Hz), 7.13 (d, 1H, J=8.0 Hz), 4.62-4.54 (m, 0.5H), 4.50-4.41 (m, 0.5H), 4.27-4.17 (m, 0.5H), 4.09-3.97 (m, 1H), 3.68-3.54 (m, 1H), 3.49-3.33 (m, 2H), 3.12-2.98 (m, 1H), 2.74 (m, 0.5H), 2.56-2.45 (m, 0.5H), 2.36 (m, 0.5H), 2.26-2.16 (m, 0.5H), 2.13-2.01 (m, 1H), 2.01-1.87 (m, 0.5H), 1.87-1.64 (m, 3.5H), 1.64-1.33 (m, 3.5H), 0.76 (app. s, 3H), 0.74 (s, 0.5×3H), 0.62 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.34 minutes.]

Example 18

Mixture of N-((3R,4R)-3-((S)-4-(4-chlorophenyl)-4-hydroxy-3,3-dimethylpiperidine-1-carbonyl)tetrahydro-2H-pyran-4-yl)benzamide and N-((3S,4S)-3-((S)-4-(4-chlorophenyl)-4-hydroxy-3,3-dimethylpiperidine-1-carbonyl)tetrahydro-2H-pyran-4-yl)benzamide

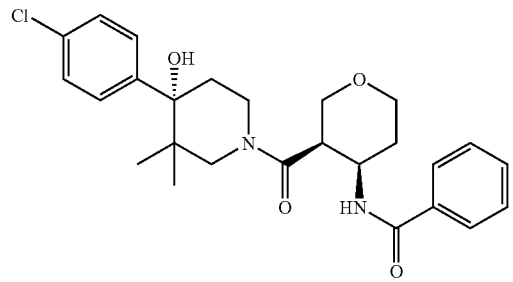 [SMILES: CC1(C)CN(C(=O)[C@H]2COCC[C@H]2NC(=O)c2ccccc2)CC[C@]1(O)c1ccc(Cl)cc1]

Step 1: Preparation of a mixture of (3R,4R)-methyl 4-benzamidotetrahydro-2H-pyran-3-carboxylate and (3S,4S)-methyl 4-benzamidotetrahydro-2H-pyran-3-carboxylate

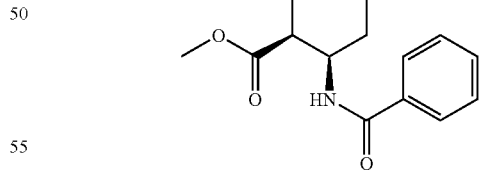

A mixture of (3S,4S)- and (3R,4R)-methyl 4-aminotetrahydro-2H-pyran-3-carboxylate, HBr (prepared in a similar manner as described in International Patent application No. WO 2003/024899, 500 mg, 2.083 mmol), benzoic acid (254 mg, 2.083 mmol), HOBt (383 mg, 2.499 mmol), EDC (479 mg, 2.499 mmol) and triethylamine (0.581 mL, 4.17 mmol) were mixed in methylene chloride (10 mL) at 25° C. and stirred for 20 hours. At the conclusion of this period, the reaction was worked up by adding methylene chloride and then rinsing the mixture with saturated sodium carbonate (1×). The methylene chloride layer was dried over sodium sulfate and concentrated to give an off-white solid. The off-white solid was purified over silica gel in 3:1 to 1:1 hexanes/EtOAc to 100% EtOAc to yield a mixture of (3R,4R)-methyl 4-benzamidotetrahydro-2H-pyran-3-carboxylate and (3S,4S)-methyl 4-benzamidotetrahydro-2H-pyran-3-carboxylate (500 mg, 1.899 mmol, 91% yield) as a white solid. MS (ESI$^+$)=264.24 (M+H)$^+$.

Step 2: Preparation of (3S,4S)- and (3R,4R)-4-benzamidotetrahydro-2H-pyran-3-carboxylic acid

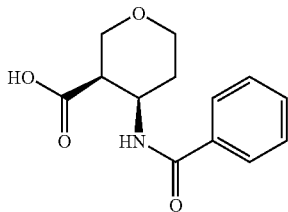 [SMILES: O=C(N[C@@H]1CCOC[C@@H]1C(=O)O)c1ccccc1]

A mixture of (3R,4R)-methyl 4-benzamidotetrahydro-2H-pyran-3-carboxylate and (3S,4S)-methyl 4-benzamidotetrahydro-2H-pyran-3-carboxylate (500 mg, 1.899 mmol) was dissolved in tetrahydrofuran (10 mL) at 25° C. and 0.5N LiOH (7.60 mL, 3.80 mmol) was added thereto. Upon completion of addition, the reaction was stirred for 20 hours. After this time, the reaction was worked up by adding water and then removing the THF in vacuo. The basic aqueous mixture was acidified to pH=3 with 1N HCl. The resulting solids were dissolved and extracted 2 times with methylene chloride. The organic layers were combined, dried over sodium sulfate and concentrated to give an oily white solid. The solid was stirred in Et$_2$O, filtered, and dried under high vacuum to yield (3S,4S)- and (3R,4R)-4-benzamidotetrahydro-2H-pyran-3-carboxylic acid (350 mg, 1.404 mmol, 73.9% yield) as a white solid. MS (ESI$^+$)=250.23 (M+H)$^+$.

Step 3: Example 18

(S)-4-(4-Chlorophenyl)-3,3-dimethylpiperidin-4-ol (25 mg, 0.104 mmol), a mixture of (3R,4R)- and (3S,4S)-4-benzamidotetrahydro-2H-pyran-3-carboxylic acid (26.0 mg, 0.104 mmol), HOBt (19.16 mg, 0.125 mmol), EDC (23.99 mg, 0.125 mmol) and triethylamine (0.029 mL, 0.209 mmol) were mixed in methylene chloride (3 mL) at 25° C. and stirred for 4 days. At the conclusion of this period, the reaction was worked up by adding methylene chloride and then rinsing with saturated sodium carbonate (1×). The methylene chloride layer was dried over sodium sulfate and concentrated to give a colorless oil. The colorless oil was purified by preparative HPLC to yield Example 18 (34 mg, 0.058 mmol, 55.7% yield) as a white solid. MS (ESI$^+$)=471.09 (M+H)$^+$. $^1$H NMR (CD$_3$OD, 400 MHz) (NMR shows several rotamers) δ 7.79 (d, 1H, J=8.0 Hz), 7.76 (d, 1H, J=8.0 Hz), 7.62-7.43 (m, 4H), 7.38-7.23 (m, 3H), 4.65-4.53 (m, 1H), 4.42-4.34 (m, 0.5H), 4.19-4.10 (m, 0.5H), 4.10-3.89 (m, 2.5H), 3.89-3.82 (m, 0.5H), 3.76-3.68 (m, 1H), 3.68-3.58 (m, 1.5H), 3.53-3.47 (m, 1H), 3.11 (m, 0.5H), 3.01 (d, 0.5H, J=8 Hz), 2.76 (m, 0.5H), 2.66-2.54 (m, 0.5H), 2.54-2.41 (m, 0.5H), 2.26-2.14 (m, 0.5H), 2.00-1.85 (m, 0.5H), 1.82-1.72 (m, 0.5H), 1.58-1.43 (m, 1H), 0.79 (s, 0.5×3H), 0.77 (s, 0.5×3H), 0.75 (s, 0.5×3H), 0.65 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Solvent B=90% MeOH-10% H$_2$O-0.1% TFA; Column 1=Waters Sunfire C18 4.6×50 mm (4 min. grad); Retention Time=2.12 minutes.]

Example 19

Benzyl (1R,2S)-2-((S)-4-(4-chlorophenyl)-4-hydroxy-3,3-dimethylpiperidine-1-carbonyl)cyclohexylcarbamate

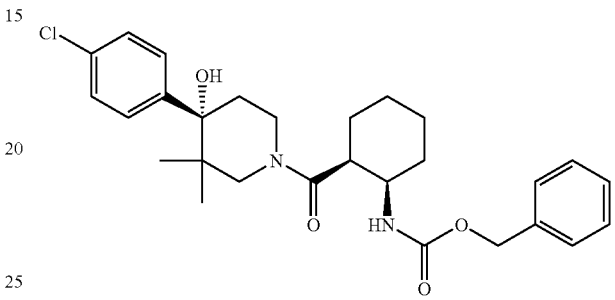

((1S,2R)-2-Aminocyclohexyl)((S)-4-(4-chlorophenyl)-4-hydroxy-3,3-dimethylpiperidin-1-yl)methanone, HCl salt (20 mg, 0.05 mmol) was added as a solution in THF to a vessel containing benzyl carbonochloridate (18 mg, 0.11 mmol). To this mixture was added THF (250 μL) and 50 μL of N',N'-diisopropylethylamine Upon completion of addition, the reaction was shaken for 20 hours and then purified by preparatory HPLC/MS without workup to yield Example 19 (27 mg, 0.05 mmol, 100% yield). MS (ESI$^+$)=499.13 (M+H)$^+$.

Example 20

N-((1R,2S)-2-((S)-4-(4-Chlorophenyl)-4-hydroxy-3,3-dimethylpiperidine-1-carbonyl)cyclohexyl)propionamide

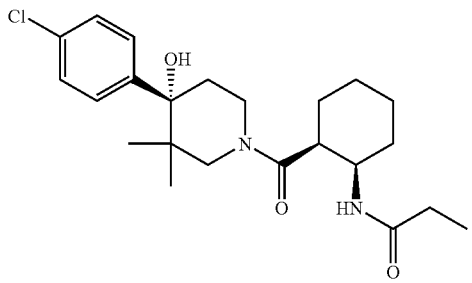 [SMILES: CCC(=O)N[C@@H]1CCCC[C@@H]1C(=O)N1CC[C@](O)(c2ccc(Cl)cc2)C(C)(C)C1]

((1S,2R)-2-Aminocyclohexyl)((S)-4-(4-chlorophenyl)-4-hydroxy-3,3-dimethylpiperidin-1-yl)methanone, HCl salt (16 mg, 0.04 mmol), propionic acid (41 mg, 0.55 mmol), HOBt (6.8 mg, 0.05 mmol), EDC (6.8 mg, 0.05 mmol) and N',N'-diisopropylethylamine (0.035 mL, 0.2 mmol) were mixed in DMF (0.6 mL) at 25° C. The reaction was shaken for 20 hours and then purified by preparatory HPLC/MS without workup to yield Example 20 (10.6 mg, 0.025 mmol, 63% yield). MS (ESI$^+$)=421.08 (M+H)$^+$.

Example 21

3-(2-(Benzyloxymethyl)-2H-tetrazol-5-yl)-N-((1R,2S)-2-((S)-4-(4-chlorophenyl)-4-hydroxy-3,3-dimethylpiperidine-1-carbonyl)cyclohexyl)benzamide

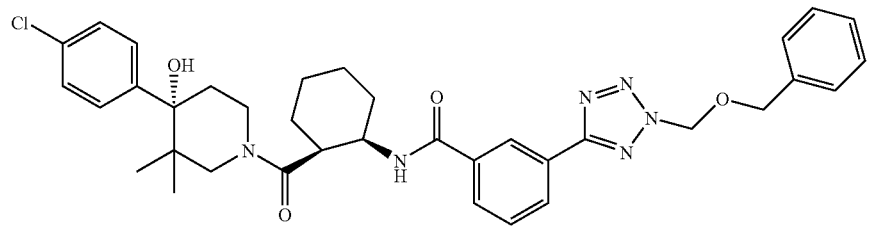 [SMILES: CC1(C)CN(C(=O)[C@H]2CCCC[C@H]2NC(=O)c2cccc(-c3nnn(COCc4ccccc4)n3)c2)CC[C@]1(O)c1ccc(Cl)cc1]

Step 1: 2-(Benzyloxymethyl)-2H-tetrazole

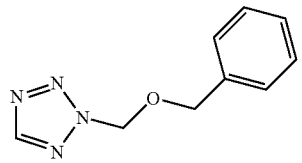 [SMILES: c1ccc(COCn2ncnn2)cc1]

A suspension of 1-H-tetrazole (2.0 g, 28.5 mmol) and potassium carbonate (5.9 g, 42.7 mmol) in DMF (30 mL) was treated with benzyl chloromethyl ether (5.36 g, 34.2 mmol), and the reaction mixture was stirred for 4 hours. After this time, the reaction mixture was analyzed by LC/MS, which indicated that the reaction was not complete. As a result, the reaction was treated with benzyl chloromethyl ether (0.5 g, 3.19 mmol) and stirred for about 16 additional hours. At the conclusion of this period, the mixture was filtered, and the filtrate was concentrated in vacuo to yield a residue. The residue was diluted with diethyl ether (200 mL), washed 5× with water (50 mL), once with brine, dried over sodium sulfate, and then concentrated in vacuo. The resulting residue was purified over a 6×20 mm silica gel column, eluting with 20% then 30% ethyl acetate/hexanes to yield 2-(benzyloxymethyl)-2H-tetrazole (2.39 g, 44% yield) and 1-(benzyloxymethyl)-2H-tetrazole (2.56 g, 47% yield).

Step 2: 2-(Benzyloxymethyl)-5-(tributylstannyl)-2H-tetrazole

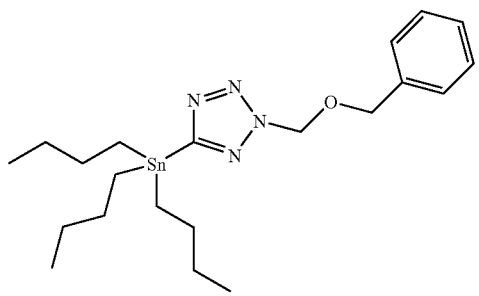 [SMILES: CCC[CH2][Sn]([CH2]CCC)([CH2]CCC)[c]1nnn(COCc2ccccc2)n1]

In a flame-dried three-neck flask, a solution of 2-(benzyloxymethyl)-2H-tetrazole (2.01 g, 10.57 mmol) and tetramethylethylenediamine (3.16 mL, 21.4 mmol) in diethyl ether (30 mL) was cooled to −78° C. Once at the prescribed temperature, the mixture was treated with the dropwise addition of n-butyllithium (1.6 M in hexanes, 7.3 mL, 11.62 mmol), which caused the color of the solution to turn dark red. Upon completion of addition, the mixture was stirred for 10 minutes, and then transferred via cannula to a solution of tributyltin chloride (2.9 mL, 10.57 mmol) in diethyl ether (20 mL) which had been pre-cooled to −78° C. Upon completion of the transfer, the reaction was stirred for 45 minutes, and then quenched with saturated ammonium chloride solution. The mixture was allowed to come to room temperature, and the aqueous and organic layers were separated. The aqueous phase was extracted 3× with ethyl acetate, and the combined organic phases were washed with brine, dried over sodium sulfate, and concentrated in vacuo to yield a residue. The residue was purified over silica gel, eluting with 1% then 5% then 10% ethyl acetate/hexanes to yield 2-(benzyloxymethyl)-5-(tributylstannyl)-2H-tetrazole (3.0 g, 60% yield) as a colorless oil.

Step 3: 3-(2-(Benzyloxymethyl)-2H-tetrazol-5-yl)benzoate

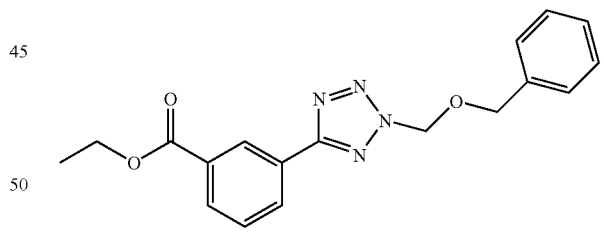

A solution of ethyl-3-bromobenzoate (0.47 g, 2.05 mmol) and 2-(benzyloxymethyl)-5-(tributylstannyl)-2H-tetrazole in toluene (20 mL) was degassed under vacuum and argon. To this solution was added copper (I) iodide (20 mg, 0.20 mmol) and tetrakis(triphenylphosphine)palladium(0) (115 mg, 0.10 mmol). Upon completion of addition, the mixture was again degassed under vacuum and argon. The flask and condenser were covered in foil to exclude light, and the reaction was heated at reflux temperature for 3 hours. After cooling to room temperature, the mixture was filtered and the filtrate was concentrated in vacuo to yield a residue. The residue was purified over a 3.5×12 cm silica gel column, eluting with 5% then 10% then 15% ethyl acetate/hexanes to yield 3-(2-(benzyloxymethyl)-2H-tetrazol-5-yl)benzoate as a colorless oil, which contained 5% of a tributyltin impurity. MS (ESI$^+$)=339.22, (M+H)$^+$. The oil was used as-is in the next step.

Step 4: 3-(2-(Benzyloxymethyl)-2H-tetrazol-5-yl)benzoic acid

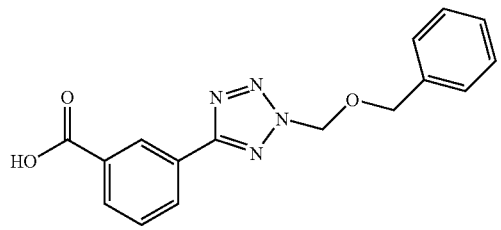 [SMILES: O=C(O)c1cccc(-c2nnn(COCc3ccccc3)n2)c1]

A solution of ethyl 3-(2-(benzyloxymethyl)-2H-tetrazol-5-yl)benzoate (653 mg, 1.93 mmol) in THF (10 mL) was treated with a 0.5 M aqueous lithium hydroxide solution (5.8 mL, 2.9 mmol), and the reaction was stirred for about 16 hours. After this time, analysis by LC/MS indicated that the reaction had not gone to completion. As such, the mixture was treated with additional 0.5 M aqueous lithium hydroxide solution (1 mL, 0.5 mmol), and the reaction was stirred for an additional 6 hours. After this time, the THF was removed under reduced pressure, and the aqueous solution was treated with 1 N HCl (3.5 mL, 3.5 mmol). The resulting mixture was extracted 3× with ethyl acetate, and the combined organic phases were dried over sodium sulfate and concentrated in vacuo to yield 3-(2-(benzyloxymethyl)-2H-tetrazol-5-yl) benzoic acid as a colorless powder, which was used as-is in the next step.

Step 5: Example 21

A mixture of ((1S,2R)-2-aminocyclohexyl)((S)-4-(4-chlorophenyl)-4-hydroxy-3,3-dimethylpiperidin-1-yl)methanone, HCl (63 mg, 0.157 mmol), 3-(2-(benzyloxymethyl)-2H-tetrazol-5-yl)benzoic acid (53.6 mg, 0.173 mmol), HOBt (52.9 mg, 0.345 mmol), and EDC (66.2 mg, 0.345 mmol) in methylene chloride (2 mL) was stirred for 30 minutes, then treated with triethylamine (0.109 mL, 0.785 mmol). The reaction was allowed to stir for 1 h at room temperature. The reaction mixture was then purified over a 12 g silica gel column, eluting at 30 mL/min with a 0-40% ethyl acetate/hexanes gradient over 10 minutes followed by 40% ethyl acetate/hexanes for 5 minutes followed by a 40-100% ethyl acetate/hexanes gradient over 10 minutes to yield Example 21 (76 mg, 0.116 mmol, 73.7% yield) as a colorless powder. MS (ESI$^+$)=657.0 (M+H)$^+$. $^1$H NMR (CD$_3$OD, 500 MHz) (NMR shows several rotamers) δ 8.52 (s, 0.5H), 8.51 (s, 0.5H), 8.33 (d, 0.5H, J=7.8 Hz), 8.29 (d, 0.5H, J=7.8 Hz), 7.91 (t, 1H, J=8.7 Hz), 7.66 (m, 1H), 7.47 (d, 1H, J=8.7 Hz), 7.37-7.22 (m, 7H), 7.15 (d, 1H, J=8.7 Hz), 6.07 (s, 2H), 4.75 (s, 1H), 4.73 (s, 1H), 4.64-4.55 (m, 1H), 4.48-4.40 (m, 0.25H), 4.22 (ddd, J=9.9, 4.8, 4.6 Hz, 0.25H), 4.08-3.97 (m, 0.75H), 3.69-3.56 (m, 1H), 3.51-3.35 (m, 1.5H), 3.19-3.00 (m, 1H), 2.74 (td, J=13.4, 4.4 Hz, 0.5H), 2.61-2.43 (m, 1H), 2.29-2.17 (m, 0.5H), 2.12-2.02 (m, 0.5H), 1.99-1.90 (m, 0.5H), 1.87-1.65 (m, 3.5H), 1.63-1.41 (m, 3.5H), 0.78 (s, 1.5H), 0.76 (s, 1.5H), 0.74 (s, 1.5H), 0.68 (s, 1.5H).

Example 22

N-((1R,2S)-2-((S)-4-(4-Chlorophenyl)-4-hydroxy-3,3-dimethylpiperidine-1-carbonyl)cyclohexyl)-3-(2H-tetrazol-5-yl)benzamide

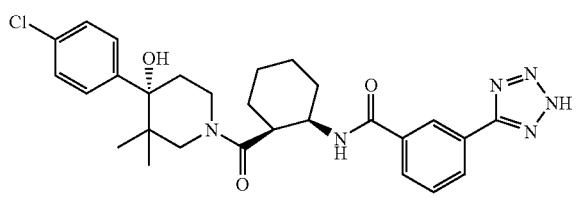 [SMILES: CC1(C)CN(C(=O)[C@H]2CCCC[C@H]2NC(=O)c2cccc(-c3nn[nH]n3)c2)CC[C@]1(O)c1ccc(Cl)cc1]

A solution of Example 21 (65 mg, 0.099 mmol) in methanol (5 mL) was treated with 6 N HCl (1 mL, 6.00 mmol), and the mixture was heated for about 16 hours at 50° C. The mixture was concentrated in vacuo to yield a residue. The residue was taken up in isopropanol (5 mL) and then concentrated to remove residual water and HCl. The resulting residue was purified over a 12 g silica gel column, eluting at 30 mL/min with a 0-10% methanol/ethyl acetate gradient over 25 minutes to yield Example 22 (33 mg, 0.061 mmol, 62.1% yield) as a colorless glass. MS (ESI$^+$)=537.3 (M)$^+$. $^1$H NMR (CD$_3$OD, 500 MHz) (NMR shows several rotamers) δ 8.43 (s, 0.5H), 8.38 (s, 0.5H), 8.21 (t, J=8.1 Hz, 1H), 7.94 (t, J=8.1 Hz, 1H), 7.70 (t, J=7.7 Hz, 0.5H), 7.67 (t, J=7.7 Hz, 0.5H), 7.48 (d, J=8.5 Hz, 1H), 7.34 (d, J=8.5 Hz, 1H), 7.30 (d, J=8.8 Hz, 1H), 7.18 (d, J=8.8 Hz, 1H), 4.57 (d, J=11.0 Hz, 0.5H), 4.48 (br. S, 0.5H), 4.29-4.19 (m, 0.5H), 4.06-3.97 (m, 1H), 3.70-3.56 (m, 1H), 3.46-3.36 (m, 1.5H), 3.10 (t, J=12.8 Hz, 0.5H), 3.03 (d, J=12.9 Hz 0.5H), 2.80-2.70 (m, 0.5H), 2.58-2.42 (m, 1H), 2.23-2.13 (m, 0.5H), 2.12-2.03 (m, 0.5H), 1.99-1.90 (m, 0.5H), 1.84-1.41 (m, 7H), 1.34-1.21 (m, 0.5H)) 0.91-0.86 (m, 0.5H), 0.78 (s, 1.5H), 0.76 (s, 1.5H), 0.74 (s, 1.5H), 0.69 (s, 1.5H). [LCMS method: Inj. Vol.=10 uL; Start % B=0; Final % B=100; Gradient Time=4 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=3.65 min.]

Example 23

3-(2-(Benzyloxymethyl)-2H-tetrazol-5-yl)-N-((1R,2S)-2-((S)-4-(4-chlorophenyl)-4-hydroxy-3,3-dimethylpiperidine-1-carbonyl)cyclopentyl)benzamide

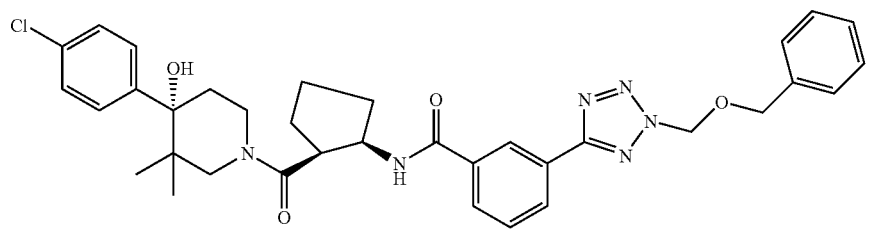 [SMILES: CC1(C)CN(C(=O)[C@H]2CCC[C@H]2NC(=O)c2cccc(-c3nnn(COCc4ccccc4)n3)c2)CC[C@]1(O)c1ccc(Cl)cc1]

Example 23 was prepared from ((1S,2R)-2-aminocyclopentyl)((S)-4-(4-chlorophenyl)-4-hydroxy-3,3-dimethylpiperidin-1-yl)methanone, HCl and 3-(2-(benzyloxymethyl)-2H-tetrazol-5-yl)benzoic acid using similar conditions as described in Example 21. MS (ESI⁺)=643.2 (M)⁺. ¹H NMR (CD₃OD, 500 MHz) (NMR shows several rotamers) δ 8.49 (s, 0.3H), 8.46 (s, 0.7H), 8.28 (d, J=7.7 Hz, 0.3H), 8.23 (d, J=7.7 Hz, 0.7H), 7.87 (d, J=8.5 Hz, 0.3H), 7.82 (d, J=7.7 Hz, 0.7H), 7.64 (t, J=7.7 Hz, 0.3H), 7.58 (t, J=7.8 Hz, 0.7H), 7.38 (d, J=8.8 Hz, 1.4H), 7.30-7.16 (m, 7H), 7.10 (d, J=8.8 Hz, 0.6H), 6.01 (s, 2H), 4.73 (q, J=7.4 Hz, 0.7H), 4.68 (s, 1.4H), 4.66 (s, 0.6H), 4.62-4.55 (m, 0.3H), 4.54-4.50 (q, J=7.4 Hz, 0.3H), 4.08-3.96 (m, 1.4H), 3.61-3.44 (m, 2.3H), 3.11-3.02 (m, 0.3H), 2.91 (d, J=12.9 Hz, 0.7H), 2.64 (td, J=13.5, 4.5 Hz, 0.7H), 2.45 (td, J=13.5, 4.5 Hz, 0.3H), 2.23-1.74 (m, 5H), 1.69-1.56 (m, 1H), 1.50-1.36 (m, 1H), 0.73 (s, 1H), 0.67-0.63 (m, 5H). [LCMS method: Inj. Vol.=10 uL; Start % B=0; Final % B=100; Gradient Time=4 min; Flow Rate=4 ml/min; Wavelength=220 nm; Solvent A=10% MeOH-90% H₂O-0.1% TFA; Solvent B=90% MeOH-10% H₂O-0.1% TFA; Column 1=Waters Sunfire C18 4.6×50 mm (4 min. grad); Retention Time=4.15 min.]

Example 24

N-((1R,2S)-2-((S)-4-(4-Chlorophenyl)-4-hydroxy-3,3-dimethylpiperidine-1-carbonyl)cyclopentyl)-3-(2H-tetrazol-5-yl)benzamide

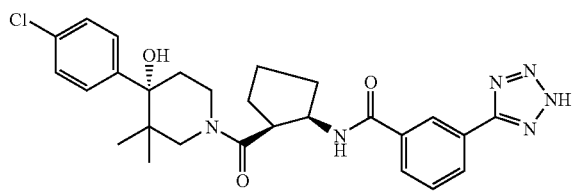 [SMILES: CC1(C)CN(C(=O)[C@H]2CCC[C@H]2NC(=O)c2cccc(-c3nn[nH]n3)c2)CC[C@]1(O)c1ccc(Cl)cc1]

Example 24 was prepared from 3-(2-(benzyloxymethyl)-2H-tetrazol-5-yl)-N-((1R,2S)-2-((S)-4-(4-chlorophenyl)-4-hydroxy-3,3-dimethylpiperidine-1-carbonyl)cyclopentyl)benzamide using similar conditions as described in Example 22. MS (ESI⁺)=523 (M)⁺. ¹H NMR (CD₃OD, 500 MHz) (NMR shows several rotamers) (NMR indicates contamination with 0.5 eq. (mol) of benzyl alcohol—chemical shifts for contaminant not reported) δ 8.46 (s, 0.3H), 8.39 (s, 0.7H), 8.24 (d, J=8.0 Hz, 0.3H), 8.20 (d, J=8.0 Hz, 0.7H), 7.97 (d, J=8.3 Hz, 0.3H), 7.91 (d, J=8.3 Hz, 0.7H), 7.73 (t, J=7.8 Hz, 0.3H), 7.67 (t, J=7.7 Hz, 0.7H), 7.45 d, J=8.8 Hz, 1.4H), 7.33 d, J=8.8 Hz, 0.6H), 7.28 (d, J=8.5 Hz, 1.4H), 7.19 (d, J=8.5 Hz, 0.6H), 4.79 (q, J=7.4 Hz, 0.7H), 4.62-4.54 (m, 0.6H), 4.15-4.06 (m, 0.7H), 4.02 (d, J=12.7 Hz, 0.7H), 3.66-3.51 (m, 2.3H), 3.18-3.06 (m, 0.3H), 2.94 (d, J=12.4 Hz, 0.7H), 2.71 (td, J=13.5, 4.7 Hz, 0.7H), 2.49 (td, J=13.3, 4.4 Hz, 0.3H), 2.29-1.80 (m, 5H), 1.76-1.63 (m, 1H), 1.53 (d, J=14.0 Hz, 0.7H), 1.50-1.44 (m, 0.3H), 0.80 (s, 0.8H), 0.77-0.68 (m, 5.2H). [LCMS method: Inj. Vol.=10 uL; Start % B=0; Final % B=100; Gradient Time=2 min; Flow Rate=5 ml/min; Wavelength=220 nm; Solvent A=10% MeOH-90% H₂O-0.1% TFA; Solvent B=90% MeOH-10% H₂O-0.1% TFA; Column 1=Sunfire S5 C18 4.6×30 mm (2 min grad); Retention Time=1.90 minutes.]

Example 25

N-((1R,2S)-2-((S)-4-(4-Chlorophenyl)-4-hydroxy-3,3-dimethylpiperidine-1-carbonyl)cyclohexyl)-3-(hydroxymethyl)benzamide

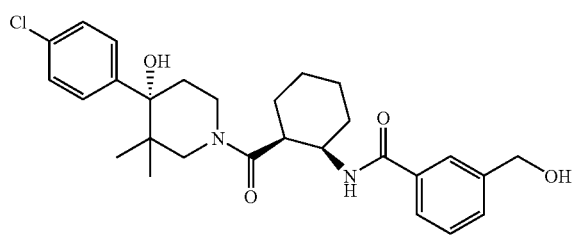 [SMILES: CC1(C)CN(C(=O)[C@H]2CCCC[C@H]2NC(=O)c2cccc(CO)c2)CC[C@]1(O)c1ccc(Cl)cc1]

Step 1: Methyl 3-(hydroxymethyl)benzoate

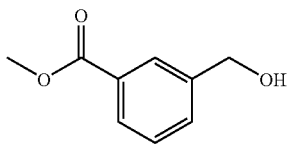

A solution of 3-(methoxycarbonyl)benzoic acid (1.05 g, 5.83 mmol) in THF (25 mL) was cooled to 0° C., and then treated with the dropwise addition of 2.0 M borane-methylsulfide complex in THF (14.57 mL, 29.1 mmol) at a rate which did not allow the temperature to exceed 5° C. The mixture was stirred at 0° C. for 15 minutes, and then allowed to warm to room temperature where it stirred for 4 hours. After this time, the reaction was cooled to 0° C. and then quenched with the addition of small pieces of ice, causing vigorous gas evolution. When gas evolution had ceased, the mixture was diluted with brine and extracted 3× with ethyl acetate. The combined organic phases were washed 3× with diluted bleach to remove residual methyl sulfide, 3× with saturated sodium carbonate to remove any unreacted acid, 1× with water, 1× with brine, dried over sodium sulfate and then concentrated in vacuo to yield the methyl 3-(hydroxymethyl)benzoate (845 mg, 5.09 mmol, 87% yield) as a colorless oil.

Step 2: 3-(Hydroxymethyl)benzoic acid

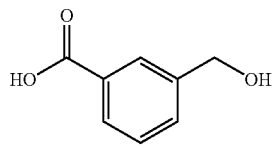 [SMILES: O=C(O)c1cccc(CO)c1]

A solution of methyl 3-(hydroxymethyl)benzoate (845 mg, 5.09 mmol) in methanol (15 mL) was treated with 1 M NaOH (aq) (15.300 mL, 15.30 mmol), and the reaction was stirred for about 16 hours at room temperature. At the conclusion of

Step 3: Example 25

Example 25 was prepared from ((1S,2R)-2-aminocyclohexyl)((S)-4-(4-chlorophenyl)-4-hydroxy-3,3-dimethylpiperidin-1-yl)methanone, HCl and 3-(hydroxymethyl)benzoic acid using similar conditions as described in Example 21, step 5. MS (ESI$^+$)=499.3 (M)$^+$. $^1$H NMR (CD$_3$OD, 500 MHz) (NMR shows several rotamers) δ 7.76 (s, 0.5H), 7.74 (s, 0.5H), 7.66 (t, J=8.0 Hz, 1H), 7.57-7.50 (m, 1H), 7.49-7.40 (m, 2H), 7.35 (d, J=8.8 Hz, 1H), 7.30 (d, J=8.5 Hz, 1H), 7.24 (d, J=8.5 Hz, 1H), 4.68 (s, 1H), 4.66 (s, 1H), 4.55 (m, 0.5H), 4.42-4.35 (m, 0.5H), 4.18 (ddd, J=9.4, 4.5, 4.3 Hz, 0.5H), 4.04-3.96 (m, 1H), 3.68-3.54 (m, 1H), 3.45-3.35 (m, 1.5H), 3.08 (td, J=12.9, 3.0 Hz, 0.5H), 3.01 (d, J=12.7 Hz, 0.5H), 2.73 (td, J=13.4, 4.5 Hz, 0.5H), 2.54-2.38 (m, 1H), 2.25-2.14 (m, 0.5H), 2.09-2.01 (m, 0.5H), 1.96-1.87 (m, 0.5H), 1.82-1.41 (m, 7H), 0.78 (s, 1.5H), 0.76 (s, 1.5H), 0.74 (s, 1.5H), 0.66 (s, 1.5H). [LCMS method: Inj. Vol.=10 uL; Start % B=0; Final % B=100; Gradient Time=4 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=3.70 min.]

Example 26

N-((1R,2S)-2-((S)-4-(4-Chlorophenyl)-4-hydroxy-3,3-dimethylpiperidine-1-carbonyl)cyclopentyl)-3-(hydroxymethyl)benzamide

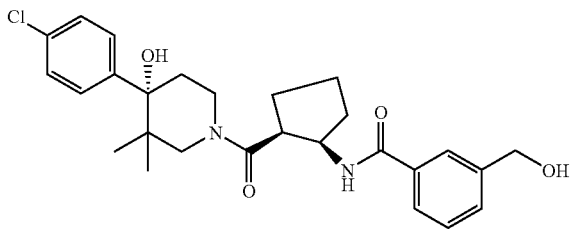 [SMILES: CC1(C)CN(C(=O)[C@H]2CCC[C@H]2NC(=O)c2cccc(CO)c2)CC[C@]1(O)c1ccc(Cl)cc1]

Example 26 was prepared from ((1S,2R)-2-aminocyclopentyl)((S)-4-(4-chlorophenyl)-4-hydroxy-3,3-dimethylpiperidin-1-yl)methanone, HCl and 3-(hydroxymethyl)benzoic acid using similar conditions as described in Example 21, step 5. MS (ESI$^+$)=485.3 (M)$^+$. $^1$H NMR (CD$_3$OD, 400 MHz) (NMR shows several rotamers) δ 7.80 (s, 0.3H), 7.73 (s, 0.7H), 7.69 (d, J=7.5 Hz, 0.3H), 7.63 (d, J=7.5 Hz, 0.7H), 7.59-7.50 (m, 1H), 7.49-7.40 (m, 2.3H), 7.36-7.27 (m, 2H), 7.24 (d, J=8.6 Hz, 0.7H), 4.80-4.71 (m, 0.7H), 4.69 (s, 0.6H), 4.66 (s, 1.4H), 4.63-4.50 (m, 0.7H), 4.14-3.97 (m, 1.4H), 3.66-3.49 (m, 2.2H), 3.13 (td, J=12.9, 3.0 Hz, 0.3H), 2.93 (d, J=12.5 Hz, 0.7H), 2.70 (td, J=13.5, 4.6 Hz, 0.7H), 2.46 (td, J=13.6, 4.7 Hz, 0.3H), 2.27-1.78 (m, 5H), 1.77-1.59 (m, 1H), 1.56-1.44 (m, 1H), 0.80 (s, 1H), 0.74 (s, 4H), 0.68 (s, 1H). [LCMS method: Inj. Vol.=10 uL; Start % B=0; Final % B=100; Gradient Time=4 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=3.59 min.]

Example 27

N-((1R,2S)-2-((S)-4-(4-Chlorophenyl)-4-hydroxy-3,3-dimethylpiperidine-1-carbonyl)cyclohexyl)-cis-3,4-dihydroxycyclopentanecarboxamide

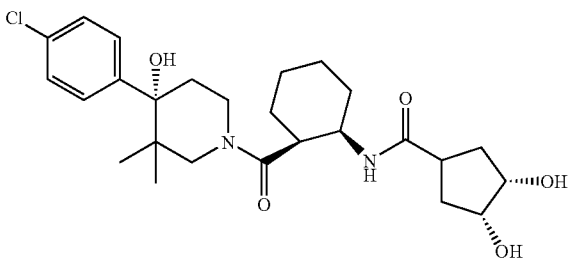 [SMILES: CC1(C)CN(C(=O)[C@H]2CCCC[C@H]2NC(=O)C2C[C@@H](O)[C@@H](O)C2)CC[C@]1(O)c1ccc(Cl)cc1]

Step 1: 2-Phenylpropan-2-yl 2,2,2-trichloroacetimidate

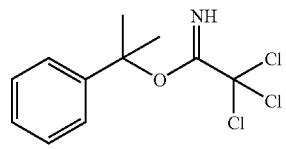

A suspension of 60% sodium hydride in mineral oil (0.42 g, 10.50 mmol) in diethyl ether (10 mL) was treated with the dropwise addition of a solution of 2-phenylpropan-2-ol (12.02 mL, 86 mmol) in diethyl ether (30 mL). Upon completion of addition, the mixture was stirred for 30 minutes, during which time a nearly clear solution was observed. After this time, the mixture was cooled to 0° C. and then treated with the dropwise addition of trichloroacetonitrile (8.18 mL, 82 mmol), which caused the mixture to turn dark brown. The reaction was allowed to warm to room temperature over 1 hour, and then was concentrated in vacuo to yield a residue. The residue was dissolved in hexanes (10 mL) and treated with methanol (0.424 mL, 10.48 mmol), and the resulting mixture was stirred vigorously for 5 minutes. The resulting black suspension was filtered through glass fiberglass filter paper, and the collected solids were rinsed 3× with hexanes. The combined filtrates were concentrated in vacuo to yield 2-phenylpropan-2-yl 2,2,2-trichloroacetimidate (23.8 g, 85 mmol, 99% yield) as an amber oil which was used as-is in the next step.

Step 2: 2-Phenylpropan-2-yl cyclopent-3-enecarboxylate

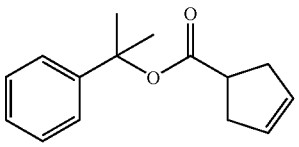 [SMILES: CC(C)(OC(=O)C1CC=CC1)c1ccccc1]

A solution of 2-phenylpropan-2-yl 2,2,2-trichloroacetimidate (23.85 g, 85 mmol) in cyclohexane (85 mL) was treated with a solution of cyclopent-3-enecarboxylic acid (4.77 g, 42.5 mmol) in methylene chloride (43 mL), and the mixture was stirred for about 16 hours at room temperature during which time a colorless solid precipitated. The precipitate was collected by filtration and rinsed with hexanes. The combined filtrates were concentrated in vacuo to yield a residue. The residue was purified over a 330 g silica gel column, eluting at 100 mL/min with a 0-5% ethyl acetate/hexanes gradient over 2 column volumes, then 5% ethyl acetate/hexanes for 2 column volumes, then a 5-40% ethyl acetate/hexanes gradient over 10 column volumes to yield 2-phenylpropan-2-yl cyclopent-3-enecarboxylate (8.84 g, 38.4 mmol, 90% yield) as a yellow oil.

Step 3: 2-Phenylpropan-2-yl cis-3,4-dihydroxycyclopentanecarboxylate

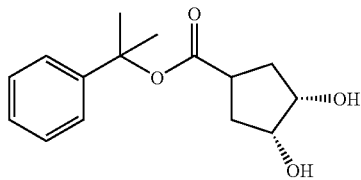 [SMILES: CC(C)(OC(=O)C1C[C@@H](O)[C@@H](O)C1)c1ccccc1]

A suspension of AD-Mix beta (1.3 g) and methanesulfonamide (83 mg, 0.868 mmol) in 1:1 t-butanol/water (8 mL) was cooled to 0° C. and treated with 2-phenylpropan-2-yl cyclopent-3-enecarboxylate (200 mg, 0.868 mmol). The mixture was stirred for 4 hours at 0° C. and then allowed to warm to room temperature where it stirred for 13 days. The resulting yellow suspension was treated with sodium sulfite (3 g), and the mixture was stirred for 30 minutes, during which time the color faded. After the 30 minute period, the mixture was diluted with water and extracted 3× with ethyl acetate. The combined organic phases were dried over sodium sulfate and concentrated in vacuo. The resulting residue was purified over a 40 g silica gel column, eluting at 40 mL/min with a 0-50% ethyl acetate/hexanes gradient over 15 minutes to yield 2-phenylpropan-2-yl cis-3,4-dihydroxycyclopentanecarboxylate (165 mg, 0.624 mmol, 71.9% yield) as a colorless oil.

Step 4: cis-3,4-Dihydroxycyclopentanecarboxylic acid

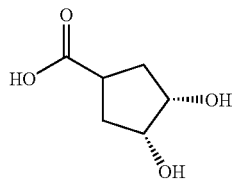

A suspension of 2-phenylpropan-2-yl 3,4-dihydroxycyclopentanecarboxylate (165 mg, 0.624 mmol) in 6 M HCl (1 mL, 6.00 mmol) was treated with a few drops of THF to increase solubility of the ester. The mixture was stirred for about 16 hours at room temperature, and then diluted with water (5 mL) and washed 3× with ether (5 mL). The aqueous phase was concentrated in vacuo to yield a residue. The residue was taken up on isopropanol and then concentrated 3× to remove residual water and yield cis-3,4-dihydroxycyclopentanecarboxylic acid (89 mg, 0.609 mmol, 98% yield) as a sticky amber solid which was used as-is in the next step.

Step 5: Example 27

Example 27 was prepared from ((1S,2R)-2-aminocyclohexyl)((S)-4-(4-chlorophenyl)-4-hydroxy-3,3-dimethylpiperidin-1-yl)methanone, HCl and 3,4-cis-dihydroxycyclopentanecarboxylic acid using similar conditions as described in Example 21, step 5. MS (ESI$^+$)=493.3 (M)$^+$. $^1$H NMR (CD$_3$OD, 500 MHz) (NMR shows several rotamers) δ 7.53-7.42 (m, 2H), 7.35-7.27 (m, 2H), 4.58-4.49 (m, 0.4H), 4.36-4.25 (m, 0.6H), 4.11-4.05 (m, 2H), 4.01-3.90 (m, 1.6H), 3.63 (td, J=13.0, 2.6 Hz, 0.6H), 3.56 (d, J=13.2 Hz, 0.4H), 3.26 (q, J=4.6 Hz, 0.4H), 3.19 ddd, J=8.9, 4.4, 4.3 Hz, 0.6H), 3.12-2.94 (m, 2H), 2.71 (td, J=13.5, 4.7 Hz, 0.6H), 2.56 (td, J=13.5, 4.8 Hz, 0.4H), 2.37-2.20 (m, 0.4H), 1.99-1.26 (m, 13H), 0.69-0.83 (m, 6H). [LCMS method: Inj. Vol.=10 uL; Start % B=0; Final % B=100; Gradient Time=4 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=3.48 min.]

Example 28

((S)-4-(4-Chlorophenyl)-4-hydroxy-3,3-dimethylpiperidin-1-yl)((1S,2R)-2-(m-tolylamino)cyclohexyl) methanone

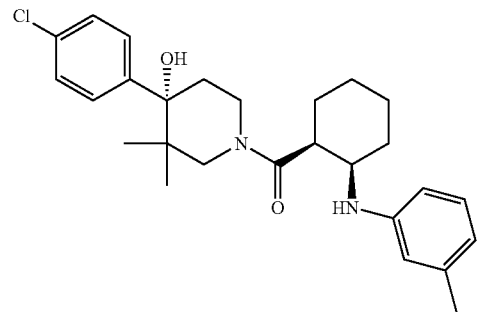 [SMILES: Cc1cccc(N[C@@H]2CCCC[C@@H]2C(=O)N2CC[C@](O)(c3ccc(Cl)cc3)C(C)(C)C2)c1]

((1S,2R)-2-Aminocyclohexyl)((S)-4-(4-chlorophenyl)-4-hydroxy-3,3-dimethylpiperidin-1-yl)methanone hydrochloride (38 mg, 0.095 mmole), m-tolylboronic acid (25.7 mg, 0.189 mmol), diacetoxycopper (17.2 mg, 0.095 mmol), Hunig's base (24.7 mg, 0.189 mmol) and dichloromethane (2 mL) were stirred at RT for 3 days. At the conclusion of this period, the reaction was passed through a silica gel plug, and the filtrate was evaporated to yield a residue. The residue was purified using preparative HPLC to yield Example 28 as a white solid (8.2 mg, 19% yield). MS (ESI$^+$)=455.29 (M+H)$^+$. $^1$H NMR (CDCl$_3$, 400 MHz)(NMR shows several rotamers) δ 7.30-7.51 (m, 5H), 7.21-7.28 (m, 3H), 4.68 (d, 0.5H, J=16 Hz), 4.14 (d, 0.5H, J=16 Hz), 3.55-3.80 (m, 2H), 3.04-3.38 (m, 2H), 2.57-2.75 (m, 1H), 2.40 (s, 3H), 2.06-2.30 (m, 2H), 1.76-1.92 (m, 2H), 1.32-1.76 (m, 6H), 0.68, 0.76, 0.85, 0.86 (4 s, 6H). [HPLC Method: Column=Chromalith Speedrod 4.6×50 mm; Inject volume=10 uL; Start % B=0; Final % B=100; Gradient time=4 min; Flow rate=4 ml/min; Wave-

Example 29

((S)-4-(4-Chlorophenyl)-4-hydroxy-3,3-dimethylpiperidin-1-yl)((1S,2R)-2-(m-tolylamino)cyclopentyl)methanone

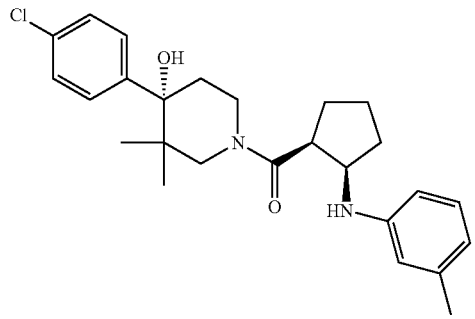 [SMILES: Cc1cccc(N[C@@H]2CCC[C@@H]2C(=O)N2CC[C@](O)(c3ccc(Cl)cc3)C(C)(C)C2)c1]

((1S,2R)-2-Aminocyclopentyl)((S)-4-(4-chlorophenyl)-4-hydroxy-3,3-dimethylpiperidin-1-yl)methanone hydrochloride (35 mg, 0.090 mmole), m-tolylboronic acid (24.7 mg, 0.181 mmol), diacetoxycopper (16.4 mg, 0.091 mmol), Hunig's base (23.36 mg, 0.181 mmol) and dichloromethane (2 mL) were stirred at RT for 3 days. At the conclusion of this period, the reaction was passed through a silica gel plug, and the filtrate was evaporated to yield a residue. The residue was purified using preparative HPLC to yield Example 29 as a white solid (14.9 mg, 21% yield). MS (ESI$^+$)=441.18 (M+H)$^+$. $^1$H NMR (CDCl$_3$, 400 MHz)(NMR shows several rotamers) δ 7.20-7.25 (m, 3H), 7.30-7.40 (m, 5H), 4.65 (d, 0.5H, J=16 Hz), 4.05-4.22 (m, 1H), 3.41-3.85 (m, 3H), 3.17-3.23 (m, 2H), 2.56-2.73 (m, 1H) 2.39, 2.40 (2 s, rotamers, 3H), 2.14-2.34 (m, 1H), 1.98-2.14 (m, 1H), 1.81-1.97 (m, 2H), 1.62-1.79 (m, 1H), 1.48-1.57 (m, 1H), 0.82, 0.86 (2s, 3H), 0.69, 0.78 (2 s, 3H). [HPLC Method: Column=Chromalith Speedrod 4.6×50 mm; Inject volume=10 uL; Start % B=0; Final % B=100; Gradient time=4 min; Flow rate=4 ml/min; Wavelength=254 nm; Solvent A=10% MeOH/90% H$_2$O 0.2% H$_3$PO$_4$; Solvent B=90% MeOH/10% H$_2$O 0.2% H$_3$PO$_4$; Retention time=3.73 min.]

Example 30

((1S,2R)-2-(Benzo[d]oxazol-2-ylamino)cyclopentyl)((S)-4-(4-chlorophenyl)-4-hydroxy-3,3-dimethylpiperidin-1-yl)methanone

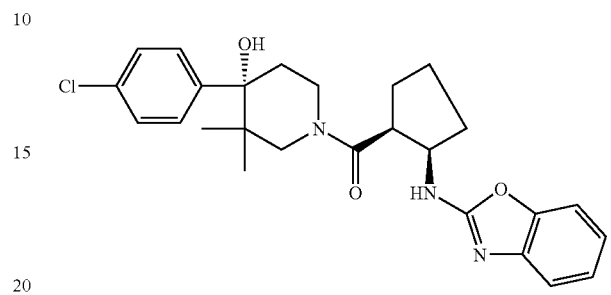

((1S,2R)-2-Aminocyclopentyl)((S)-4-(4-chlorophenyl)-4-hydroxy-3,3-dimethylpiperidin-1-yl)methanone hydrochloride (38 mg, 0.098 mmole), 2-chlorobenzooxazole (22.6 mg, 0.147 mmol), Hunig's base (31.7 mg, 0.245 mmol), and 1-butanol (0.5 mL) were microwaved in a sealed tube for 1 hr at 150° C. The reaction was then purified using preparative HPLC followed by silica gel chromatography (1:1 heptane: ethyl acetate) to yield Example 30 as a solid product (14.2 mg, 35% yield). MS (ESI$^+$)=468.26 (M+H)$^+$. $^1$H NMR (CDCl$_3$, 400 MHz)(NMR shows several rotamers) δ 7.21-7.38 (m, 6H), 7.13 (t, 1H, J=8 Hz), 7.00 (t, 1H, J=8 Hz), 6.62 (d, 0.5H, J=8 Hz), 6.35 (d, 0.5H, J=8 Hz), 4.70 (dm, 0.66H, J=8 Hz), 4.35-4.52 (2 m, 1H), 4.19 (dd, 0.33H, J=12 Hz), 3.90 (dm, 0.33H, J=12 Hz), 3.31-3.58 (m, 3H), 3.08 (dt, 0.66H, 12 Hz), 2.95 (d, 0.33H, J=12 Hz, 2.50-2.69 (2 dt, 1H, J=16 Hz), 1.85-2.20 (m, 3H), 1.63-1.77 (m, 1H), 1.46-1.59 (3 s, 6H). [HPLC Method: Column=Chromalith Speedrod 4.6×50 mm; Inject volume=10 uL; Start % B=0; Final % B=100; Gradient time=4 min; Flow rate=4 ml/min; Wavelength=254 nm; Solvent A=10% MeOH/90% H$_2$O 0.2% H$_3$PO$_4$; Solvent B=90% MeOH/10% H$_2$O 0.2% H$_3$PO$_4$; Retention time=3.11 min.]

Examples 31 to 95

Examples 31 to 95, as described in Table 1, were prepared in a similar manner as described for the preparation of Examples 1 to 30. The data in the "MS" column represents the values observed for the (M+H)$^+$ ions in MS experiments.

TABLE 1

| Example | Structure | Mass Spec (M + H)$^+$ |
|---|---|---|
| 31 | 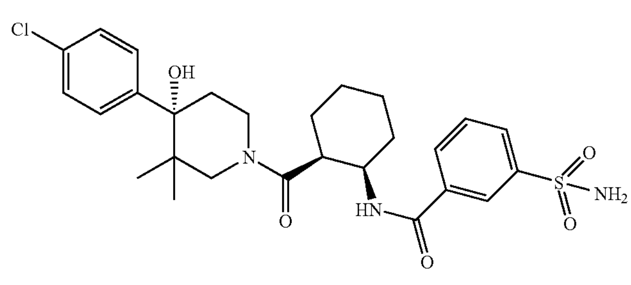 [SMILES: CC1(C)CN(C(=O)[C@H]2CCCC[C@H]2NC(=O)c2cccc(S(N)(=O)=O)c2)CC[C@]1(O)c1ccc(Cl)cc1] | 548 |

TABLE 1-continued
| Example | Structure | Mass Spec (M + H)+ |
|---|---|---|
| 32 | 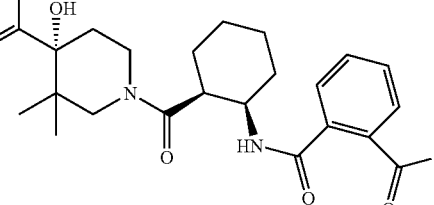 | 527 |
| 33 | 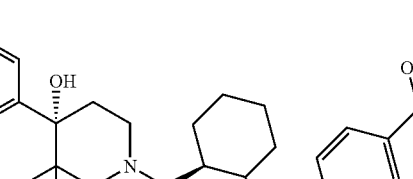 | 527 |
| 34 | 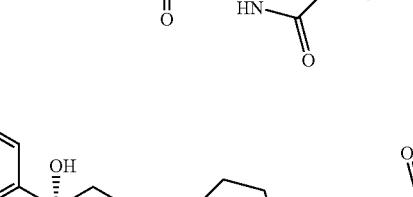 | 513 |
| 35 | 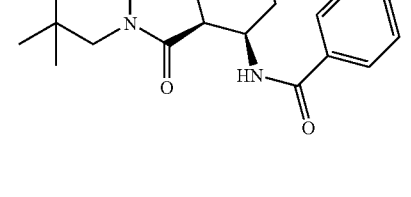 | 484 |
| 36 | 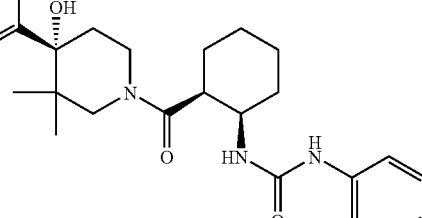 | 519 |

TABLE 1-continued
| Example | Structure | Mass Spec (M + H)+ |
|---|---|---|
| 37 | 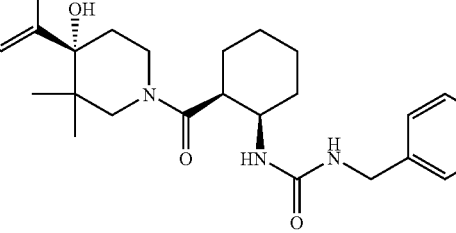 | 498 |
| 38 | 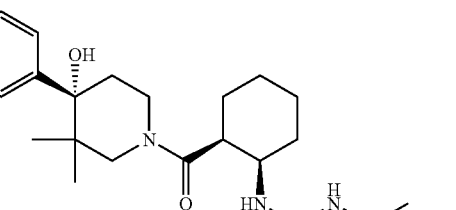 | 450 |
| 39 | 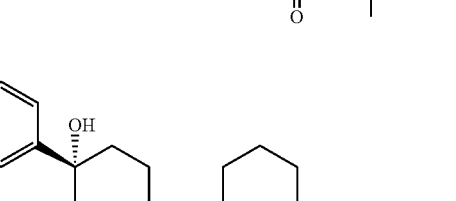 | 436 |
| 40 | 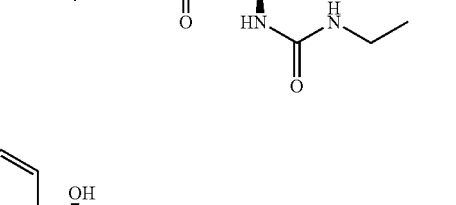 | 465 |
| 41 | 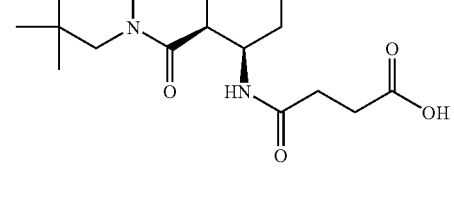 | 423 |

TABLE 1-continued
| Example | Structure | Mass Spec (M + H)+ |
|---------|-----------|--------------------|
| 42 | 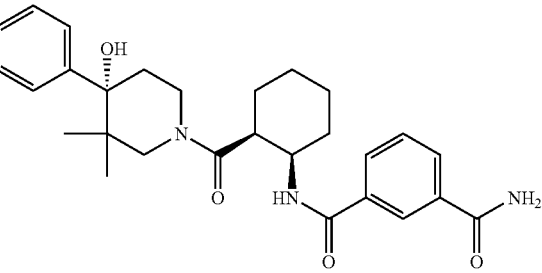 | 512 |
| 43 | 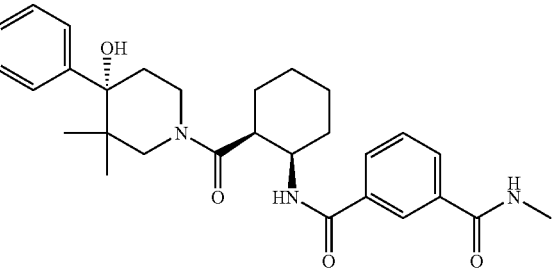 | 526 |
| 44 | 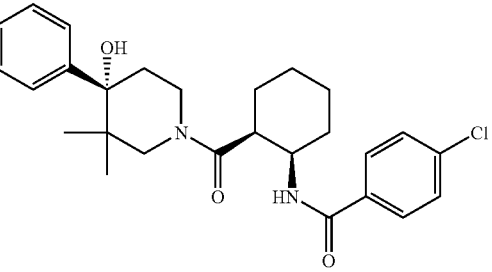 | 503 |
| 45 | 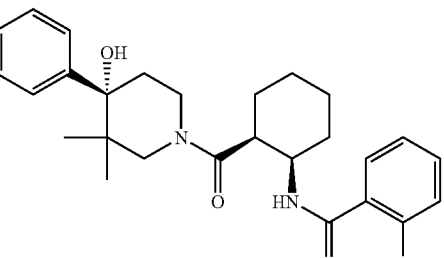 | 503 |
| 46 | 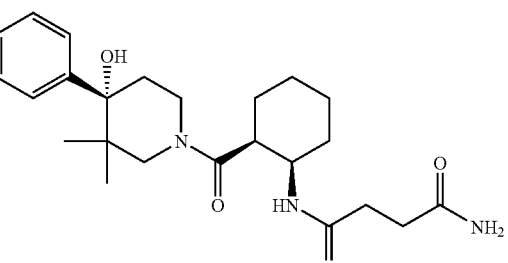 | 464 |

TABLE 1-continued
| Example | Structure | Mass Spec (M + H)+ |
|---|---|---|
| 47 | 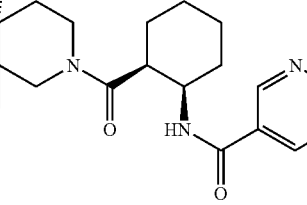 | 470 |
| 48 | 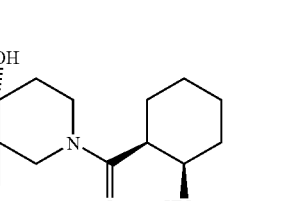 | 407 |
| 49 | 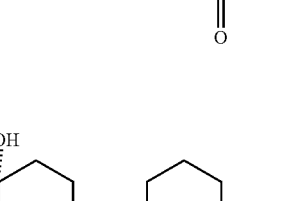 | 435 |
| 50 | 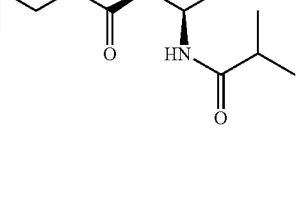 | 483 |
| 51 | 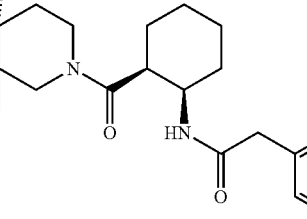 | 511 |

TABLE 1-continued

| Example | Structure | Mass Spec (M + H)+ |
|---|---|---|
| 52 | 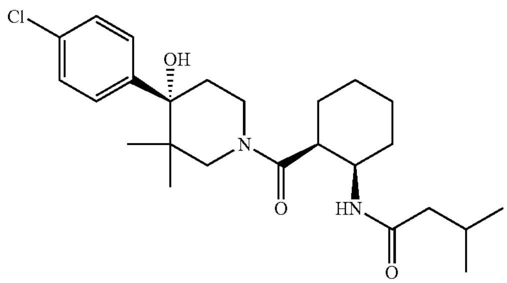 [SMILES: CC(C)CC(=O)N[C@@H]1CCCC[C@@H]1C(=O)N1CC[C@](O)(c2ccc(Cl)cc2)C(C)(C)C1] | 449 |
| 53 | 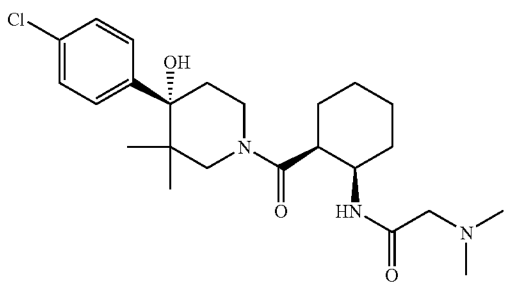 [SMILES: CN(C)CC(=O)N[C@@H]1CCCC[C@@H]1C(=O)N1CC[C@](O)(c2ccc(Cl)cc2)C(C)(C)C1] | 450 |
| 54 | 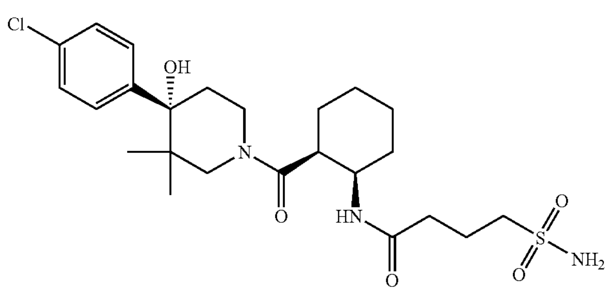 [SMILES: CC1(C)CN(C(=O)[C@H]2CCCC[C@H]2NC(=O)CCCS(N)(=O)=O)CC[C@]1(O)c1ccc(Cl)cc1] | 514 |
| 55 | 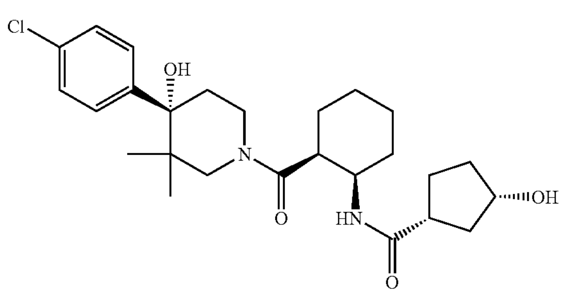 [SMILES: CC1(C)CN(C(=O)[C@H]2CCCC[C@H]2NC(=O)[C@@H]2CC[C@H](O)C2)CC[C@]1(O)c1ccc(Cl)cc1] | 477 |
| 56 | 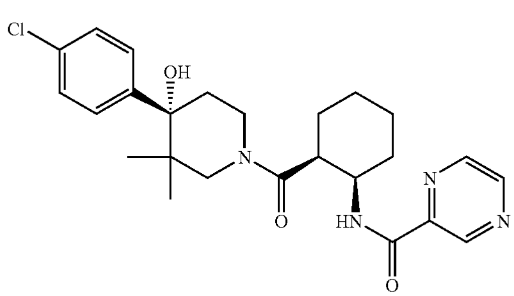 [SMILES: CC1(C)CN(C(=O)[C@H]2CCCC[C@H]2NC(=O)c2cnccn2)CC[C@]1(O)c1ccc(Cl)cc1] | 471 |

TABLE 1-continued
| Example | Structure | Mass Spec (M + H)+ |
|---|---|---|
| 57 | 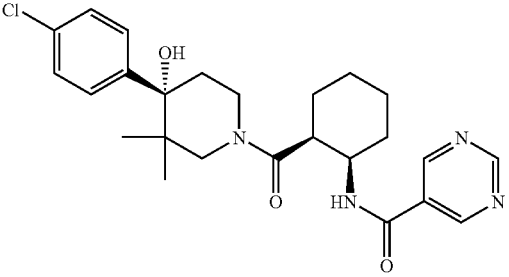 [SMILES: CC1(C)CN(C(=O)[C@H]2CCCC[C@H]2NC(=O)c2cncnc2)CC[C@]1(O)c1ccc(Cl)cc1] | 471 |
| 58 | 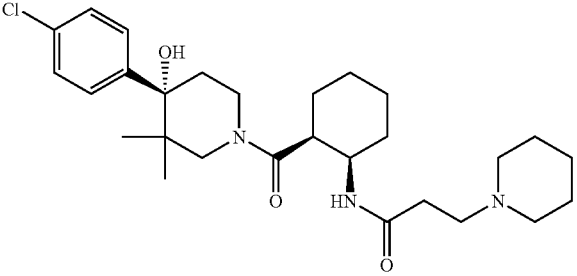 [SMILES: CC1(C)CN(C(=O)[C@H]2CCCC[C@H]2NC(=O)CCN2CCCCC2)CC[C@]1(O)c1ccc(Cl)cc1] | 504 |
| 59 | 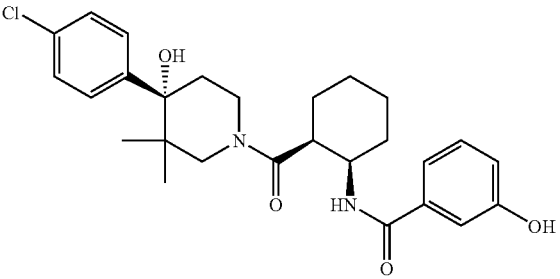 [SMILES: CC1(C)CN(C(=O)[C@H]2CCCC[C@H]2NC(=O)c2cccc(O)c2)CC[C@]1(O)c1ccc(Cl)cc1] | 485 |
| 60 | 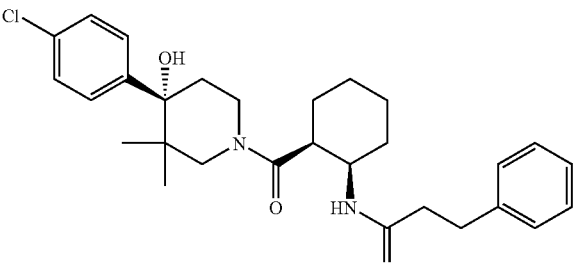 | 497 |
| 61 | 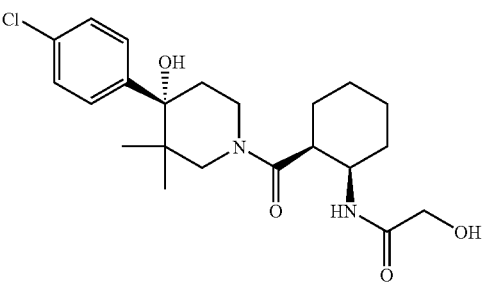 [SMILES: CC1(C)CN(C(=O)[C@H]2CCCC[C@H]2NC(=O)CO)CC[C@]1(O)c1ccc(Cl)cc1] | 423 |

TABLE 1-continued
| Example | Structure | Mass Spec (M + H)+ |
|---|---|---|
| 62 | 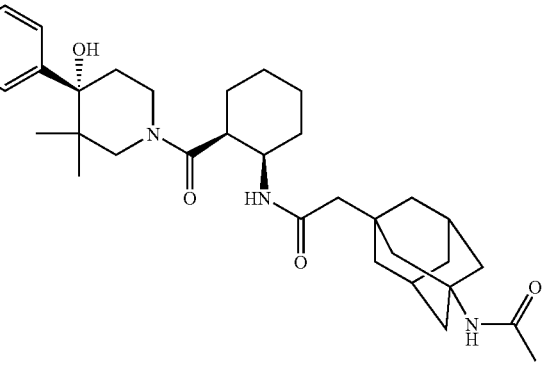 | 598 |
| 63 | 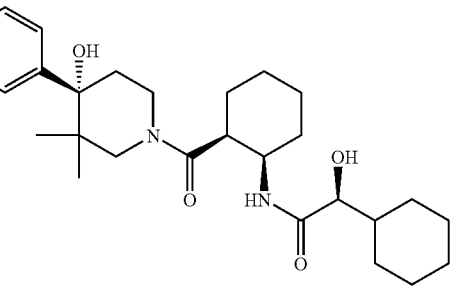 | 505 |
| 64 | 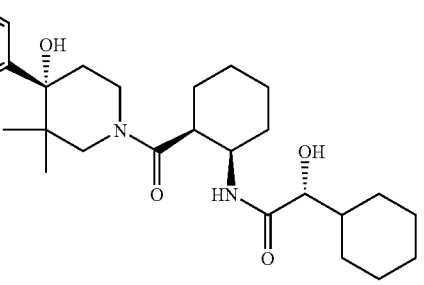 | 505 |
| 65 | 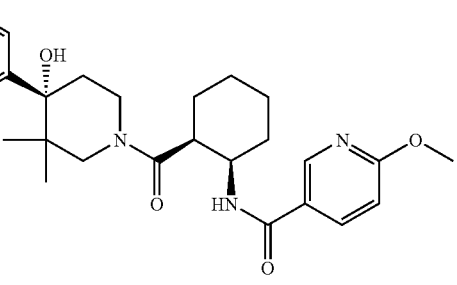 | 500 |
| 66 | 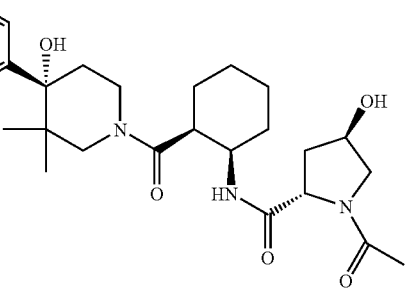 | 520 |

TABLE 1-continued

| Example | Structure | Mass Spec (M + H)+ |
|---|---|---|
| 67 | 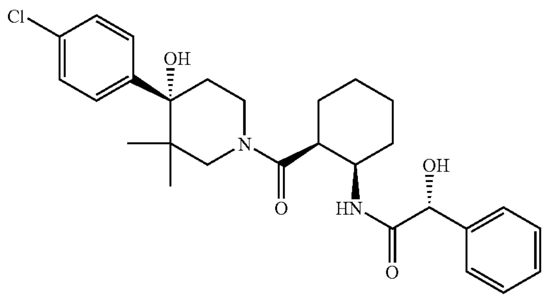 [SMILES: CC1(C)CN(C(=O)[C@H]2CCCC[C@H]2NC(=O)[C@H](O)c2ccccc2)CC[C@]1(O)c1ccc(Cl)cc1] | 499 |
| 68 | 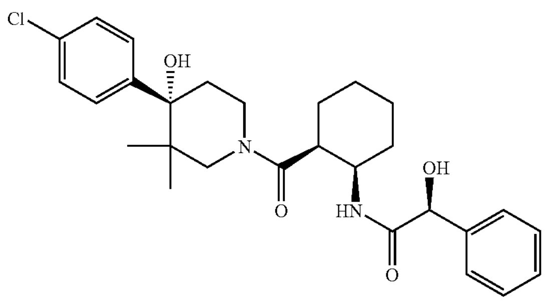 [SMILES: CC1(C)CN(C(=O)[C@H]2CCCC[C@H]2NC(=O)[C@@H](O)c2ccccc2)CC[C@]1(O)c1ccc(Cl)cc1] | 499 |
| 69 | 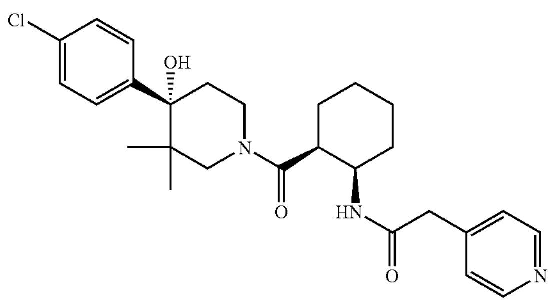 [SMILES: CC1(C)CN(C(=O)[C@H]2CCCC[C@H]2NC(=O)Cc2ccncc2)CC[C@]1(O)c1ccc(Cl)cc1] | 484 |
| 70 | 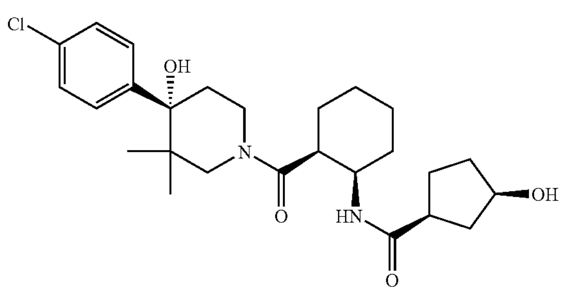 [SMILES: CC1(C)CN(C(=O)[C@H]2CCCC[C@H]2NC(=O)[C@H]2CC[C@@H](O)C2)CC[C@]1(O)c1ccc(Cl)cc1] | 477 |
| 71 | 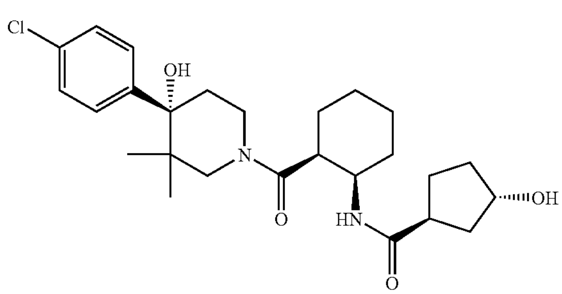 [SMILES: CC1(C)CN(C(=O)[C@H]2CCCC[C@H]2NC(=O)[C@H]2CC[C@H](O)C2)CC[C@]1(O)c1ccc(Cl)cc1] | 477 |

TABLE 1-continued

| Example | Structure | Mass Spec (M + H)+ |
|---------|-----------|--------------------|
| 72 | 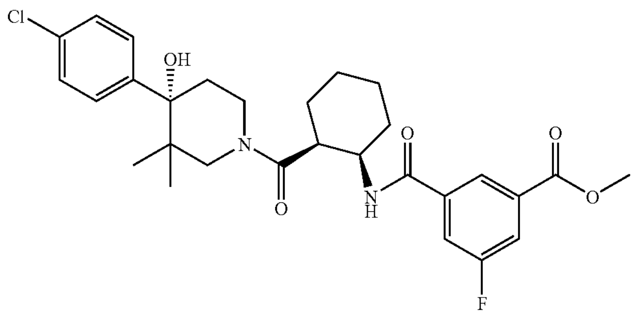 [SMILES: COC(=O)c1cc(F)cc(C(=O)N[C@@H]2CCCC[C@@H]2C(=O)N2CC[C@](O)(c3ccc(Cl)cc3)C(C)(C)C2)c1] | 545 |
| 73 | 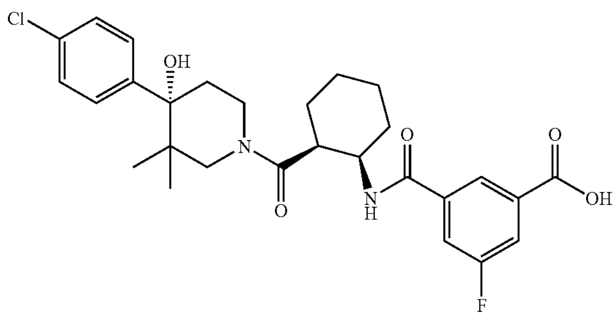 [SMILES: CC1(C)CN(C(=O)[C@H]2CCCC[C@H]2NC(=O)c2cc(F)cc(C(=O)O)c2)CC[C@]1(O)c1ccc(Cl)cc1] | 531 |
| 74 | 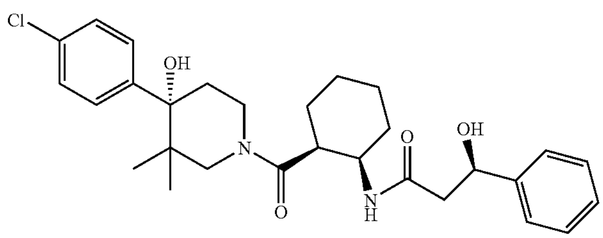 [SMILES: CC1(C)CN(C(=O)[C@H]2CCCC[C@H]2NC(=O)C[C@@H](O)c2ccccc2)CC[C@]1(O)c1ccc(Cl)cc1] | 513 |
| 75 | 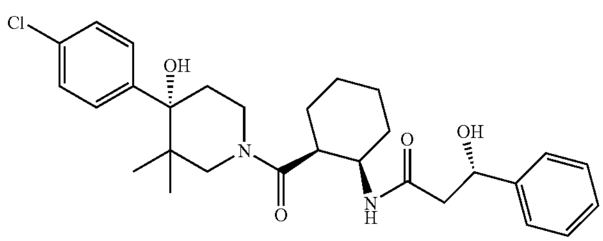 [SMILES: CC1(C)CN(C(=O)[C@H]2CCCC[C@H]2NC(=O)C[C@H](O)c2ccccc2)CC[C@]1(O)c1ccc(Cl)cc1] | 513 |
| 76 | 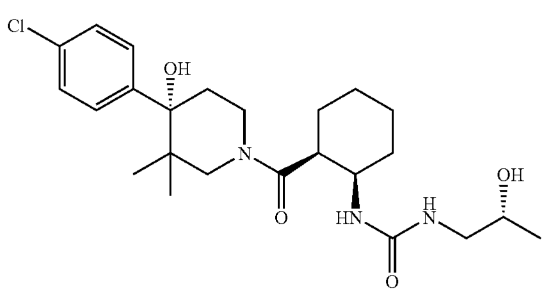 [SMILES: C[C@@H](O)CNC(=O)N[C@@H]1CCCC[C@@H]1C(=O)N1CC[C@](O)(c2ccc(Cl)cc2)C(C)(C)C1] | 466 |

TABLE 1-continued

| Example | Structure | Mass Spec (M + H)+ |
|---|---|---|
| 77 | 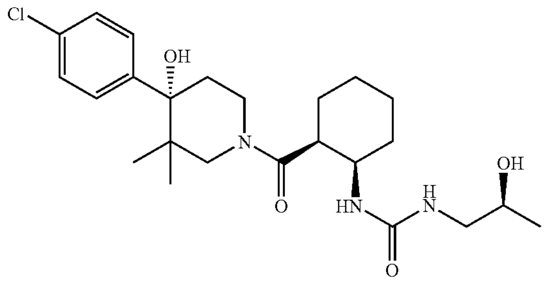 | 466 |
| 78 | 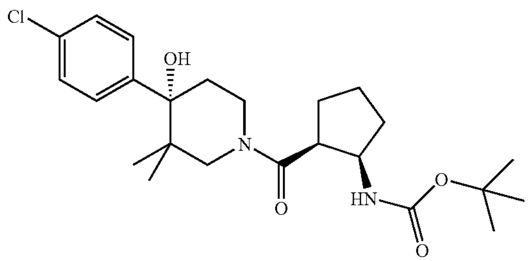 [SMILES: CC(C)(C)OC(=O)N[C@@H]1CCC[C@@H]1C(=O)N1CC[C@](O)(c2ccc(Cl)cc2)C(C)(C)C1] | 451 |
| 79 | 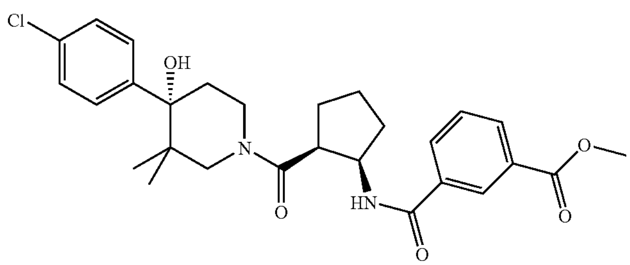 [SMILES: COC(=O)c1cccc(C(=O)N[C@@H]2CCC[C@@H]2C(=O)N2CC[C@](O)(c3ccc(Cl)cc3)C(C)(C)C2)c1] | 513 |
| 80 | 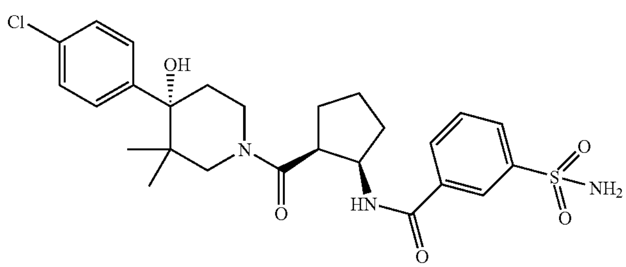 [SMILES: CC1(C)CN(C(=O)[C@H]2CCC[C@H]2NC(=O)c2cccc(S(N)(=O)=O)c2)CC[C@]1(O)c1ccc(Cl)cc1] | 534 |
| 81 | 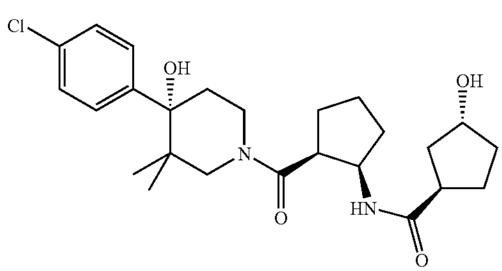 [SMILES: CC1(C)CN(C(=O)[C@H]2CCC[C@H]2NC(=O)[C@@H]2CC[C@@H](O)C2)CC[C@]1(O)c1ccc(Cl)cc1] | 463 |

TABLE 1-continued

| Example | Structure | Mass Spec (M + H)+ |
|---|---|---|
| 82 | 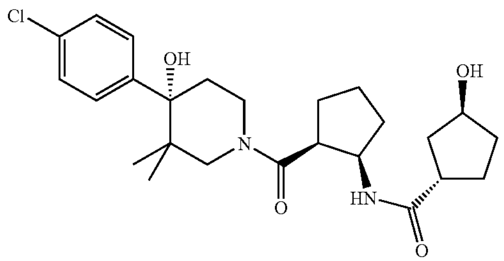 [SMILES: CC1(C)CN(C(=O)[C@H]2CCC[C@H]2NC(=O)[C@H]2CC[C@H](O)C2)CC[C@]1(O)c1ccc(Cl)cc1] | 463 |
| 83 | 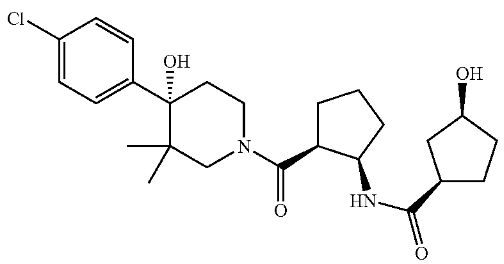 [SMILES: CC1(C)CN(C(=O)[C@H]2CCC[C@H]2NC(=O)[C@@H]2CC[C@H](O)C2)CC[C@]1(O)c1ccc(Cl)cc1] | 463 |
| 84 | 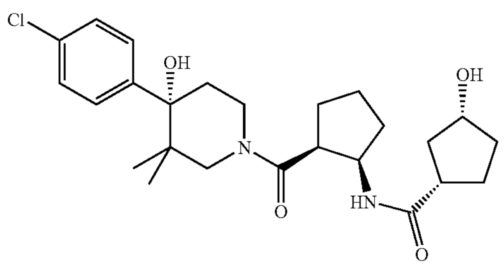 [SMILES: CC1(C)CN(C(=O)[C@H]2CCC[C@H]2NC(=O)[C@H]2CC[C@@H](O)C2)CC[C@]1(O)c1ccc(Cl)cc1] | 463 |
| 85 | 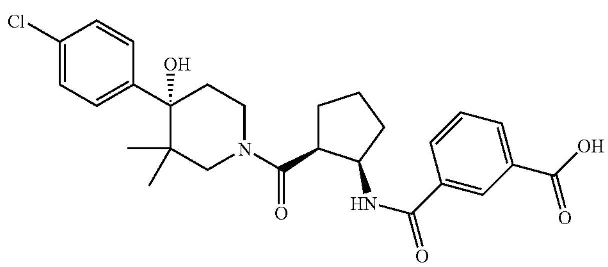 [SMILES: CC1(C)CN(C(=O)[C@H]2CCC[C@H]2NC(=O)c2cccc(C(=O)O)c2)CC[C@]1(O)c1ccc(Cl)cc1] | 499 |
| 86 | 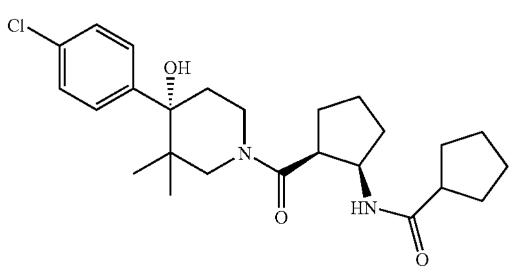 [SMILES: CC1(C)CN(C(=O)[C@H]2CCC[C@H]2NC(=O)C2CCCC2)CC[C@]1(O)c1ccc(Cl)cc1] | 447 |
| 87 | 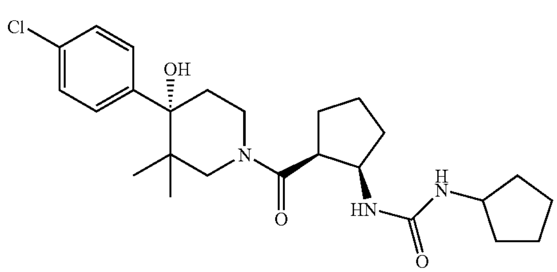 [SMILES: CC1(C)CN(C(=O)[C@H]2CCC[C@H]2NC(=O)NC2CCCC2)CC[C@]1(O)c1ccc(Cl)cc1] | 462 |

TABLE 1-continued
| Example | Structure | Mass Spec (M + H)+ |
|---------|-----------|---------------------|
| 88 | 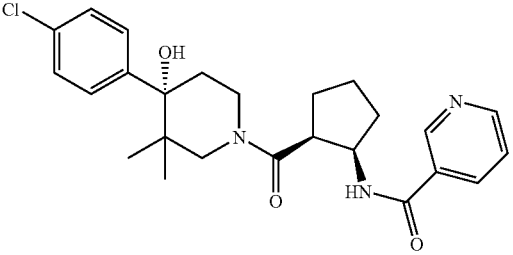 [SMILES: CC1(C)CN(C(=O)[C@H]2CCC[C@H]2NC(=O)c2cccnc2)CC[C@]1(O)c1ccc(Cl)cc1] | 456 |
| 89 | 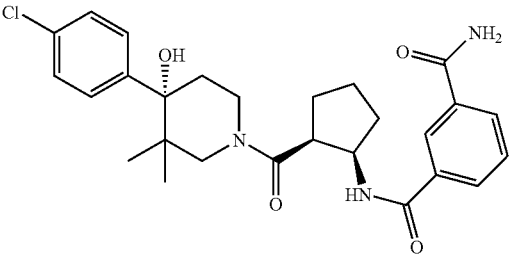 [SMILES: CC1(C)CN(C(=O)[C@H]2CCC[C@H]2NC(=O)c2cccc(C(N)=O)c2)CC[C@]1(O)c1ccc(Cl)cc1] | 498 |
| 90 | 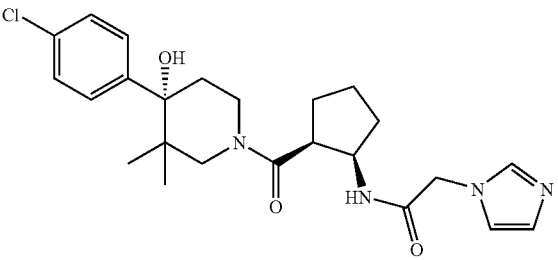 [SMILES: CC1(C)CN(C(=O)[C@H]2CCC[C@H]2NC(=O)Cn2ccnc2)CC[C@]1(O)c1ccc(Cl)cc1] | 459 |
| 91 | 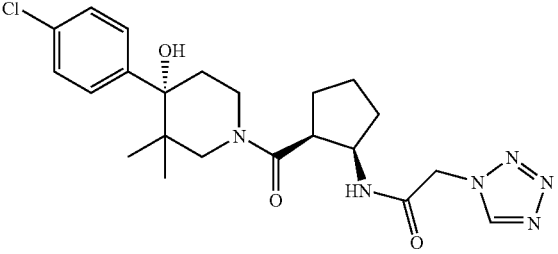 [SMILES: CC1(C)CN(C(=O)[C@H]2CCC[C@H]2NC(=O)Cn2cnnn2)CC[C@]1(O)c1ccc(Cl)cc1] | 483 |
| 92 | 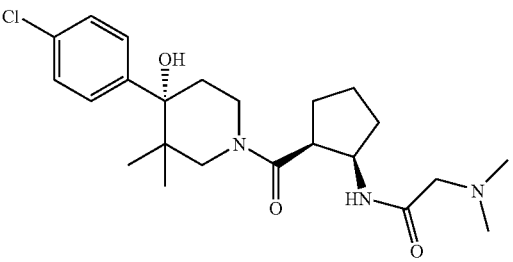 [SMILES: CN(C)CC(=O)N[C@@H]1CCC[C@@H]1C(=O)N1CC[C@](O)(c2ccc(Cl)cc2)C(C)(C)C1] | 436 |

TABLE 1-continued

| Example | Structure | Mass Spec (M + H)+ |
|---|---|---|
| 93 | 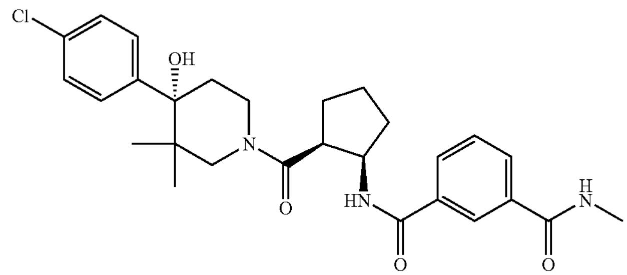 [SMILES: CNC(=O)c1cccc(C(=O)N[C@@H]2CCC[C@@H]2C(=O)N2CC[C@](O)(c3ccc(Cl)cc3)C(C)(C)C2)c1] | 512 |
| 94 | 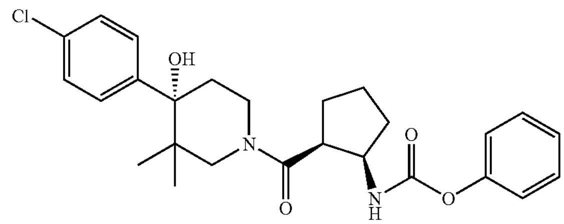 [SMILES: CC1(C)CN(C(=O)[C@H]2CCC[C@H]2NC(=O)Oc2ccccc2)CC[C@]1(O)c1ccc(Cl)cc1] | 471 |
| 95 | 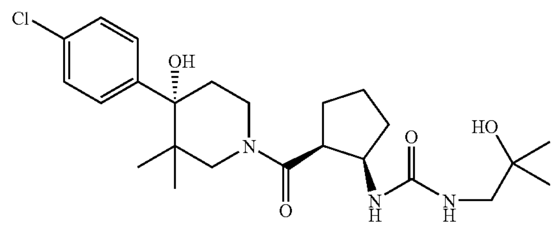 [SMILES: CC(C)(O)CNC(=O)N[C@@H]1CCC[C@@H]1C(=O)N1CC[C@](O)(c2ccc(Cl)cc2)C(C)(C)C1] | 466 |

Example 96

N-((cis)-2-((S)-4-(4-Chlorophenyl)-4-hydroxy-3,3-dimethylpiperidine-1-carbonyl)cyclobutyl)benzamide, isomer 2

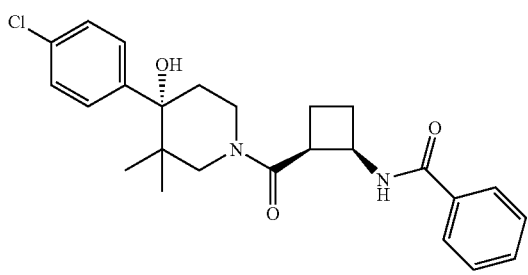 [SMILES: CC1(C)CN(C(=O)[C@H]2CC[C@H]2NC(=O)c2ccccc2)CC[C@]1(O)c1ccc(Cl)cc1]

Step 1: (±)-(cis)-2-(tert-Butoxycarbonylamino)cyclobutanecarboxylic acid

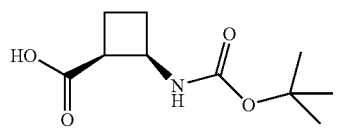

A mixture of (±)-(cis)-2-(benzyloxycarbonylamino)cyclobutanecarboxylic acid (100 mg, 0.401 mmol), BOC-anhydride (0.102 mL, 0.441 mmol), 1 M aqueous potassium hydroxide (0.441 mL, 0.441 mmol), and 10% palladium on carbon (42.7 mg, 0.401 mmol) was hydrogenated at 45 psi for 3 hours. After this time, the catalyst was removed by filtration and rinsed with methanol. The combined filtrate and rinsings were concentrated in vacuo to yield the title compound (83 mg, 0.386 mmol, 96% yield) as a colorless film. LCMS (ESI+)=238.3 (M+Na)+.

Step 2: tert-Butyl (±)-(cis)-2-((S)-4-(4-chlorophenyl)-4-hydroxy-3,3-dimethylpiperidine-1-carbonyl)cyclobutylcarbamate

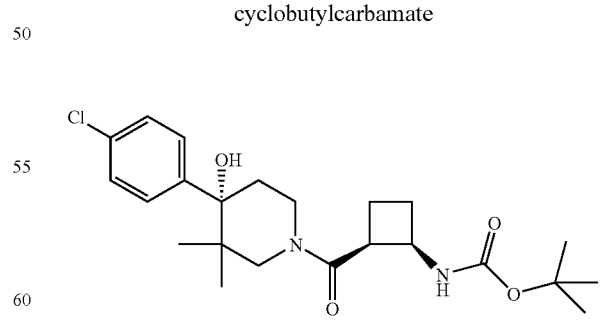

A mixture of (S)-4-(4-chlorophenyl)-3,3-dimethylpiperidin-4-ol (91 mg, 0.381 mmol), (±)-(cis)-2-(tert-butoxycarbonylamino)cyclobutanecarboxylic acid (82 mg, 0.381 mmol), and triethylamine (0.186 mL, 1.333 mmol) in methylene chloride (5 mL) was treated with BOP (168 mg, 0.381 mmol), and the mixture was stirred overnight at room temperature. At the conclusion of this period, the solvent was evaporated with a stream of nitrogen, and the resulting residue was taken up in ethyl acetate. The resulting mixture was washed 3× with saturated sodium carbonate, 3× with 1 N HCl, once with water, and once with brine, then the organic phase was concentrated in vacuo to yield the title compound (160 mg, 96% yield) as a colorless glass. The material was used as-is without further purification. MS (ESI$^+$)=437.4 (M+H)$^+$.

Step 3: ((±)-(cis)-2-Aminocyclobutyl)((S)-4-(4-chlorophenyl)-4-hydroxy-3,3-dimethylpiperidin-1-yl)methanone hydrochloride

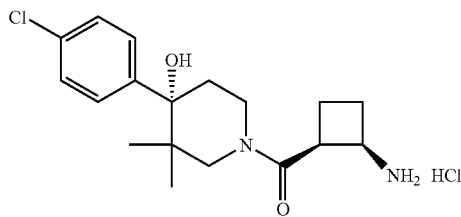 [SMILES: CC1(C)CN(C(=O)[C@H]2CC[C@H]2N)CC[C@]1(O)c1ccc(Cl)cc1 ; Cl]

A solution of tert-butyl (±)-(cis)-2-((S)-4-(4-chlorophenyl)-4-hydroxy-3,3-dimethylpiperidine-1-carbonyl)cyclobutylcarbamate (160 mg, 0.366 mmol) in 4 M HCl in dioxane (5 mL, 20.00 mmol HCl) was stirred at room temperature for 3 hours. After this time, the mixture was concentrated in vacuo, then concentrated 3× from methylene chloride to remove residual HCl and dioxane, to yield the title compound as a colorless solid which was used without purification in the next step. MS (ESI$^+$)=327.3 (M+H)$^+$.

Step 4: N-((cis)-2-((S)-4-(4-Chlorophenyl)-4-hydroxy-3,3-dimethylpiperidine-1-carbonyl)cyclobutyl)benzamide, isomer 2

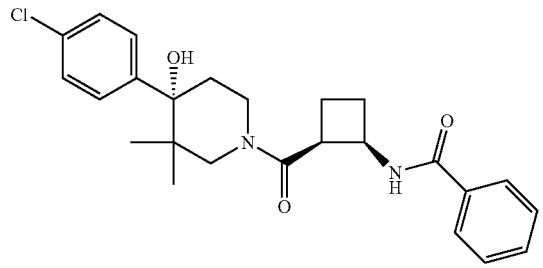 [SMILES: CC1(C)CN(C(=O)[C@H]2CC[C@H]2NC(=O)c2ccccc2)CC[C@]1(O)c1ccc(Cl)cc1]

A mixture of ((±)-(cis)-2-aminocyclobutyl)((S)-4-(4-chlorophenyl)-4-hydroxy-3,3-dimethylpiperidin-1-yl)methanone, HCl (19 mg, 0.051 mmol), benzoic acid (6.22 mg, 0.051 mmol), and triethylamine (0.025 mL, 0.178 mmol) in DMF (0.5 mL) was treated with BOP (22.51 mg, 0.051 mmol), and the resulting mixture was stirred overnight at room temperature. At the conclusion of this period, the solvent was evaporated with a stream of nitrogen, and the resulting residue was taken up in ethyl acetate. The resulting mixture was washed 3× with saturated sodium carbonate, and 3× with 1 N HCl, then the organic phase was concentrated in vacuo to yield a residue. The residue was purified via prep HPLC using the following conditions: A=H$_2$O+0.05% TFA, B=acetonitrile+0.05% TFA; Column: Phenomenex Luna 5µ, C18(2) 250×21.2 mm Flow: 15 mL/min; Gradient: 0% B over 5 min, 0-100% B over 30 min, 100% B for 5 min. Two diastereomers were isolated. Fractions containing each isomer were combined and freeze-dried to yield N-((cis)-2-((S)-4-(4-chlorophenyl)-4-hydroxy-3,3-dimethylpiperidine-1-carbonyl)cyclobutyl)benzamide, isomer 1 (3.6 mg, 8.16 µmol, 16.04% yield), MS (ESI)=441.3 (M+H)$^+$, and N-((cis)-2-((S)-4-(4-chlorophenyl)-4-hydroxy-3,3-dimethylpiperidine-1-carbonyl)cyclobutyl)benzamide, isomer 2 (4.2 mg, 9.52 µmol, 18.71% yield), MS (ESI$^+$)=441.3 (M+H)$^+$. $^1$H NMR (CD$_3$OD 500 MHz) (NMR shows multiple rotamers) δ 7.83 (d, J=8.7 Hz, 0.5H), 7.76 (d, J=8.7 Hz, 1.5H), 7.61-7.40 (m, 4.5H), 7.35 (d, J=8.7 Hz, 0.5H), 7.28 (d, J=8.7 Hz, 1.5H), 7.25 (d, J=8.7 Hz, 0.5H), 5.00 (q, J=8.3 Hz, 0.75H), 4.09 (dd, J=12.4, 1.8 Hz, 0.75H), 4.02-3.95 (m, 0.75H), 3.92-3.88 (m, 0.25H), 3.81-3.75 (m, 0.75H), 3.52 (d, J=13.3 Hz, 0.25H), 3.40-3.34 (m, 0.75H), 3.34-3.32 (m, 0.25H), 3.29-3.24 (m, 0.25H), 3.17-3.11 (m, 0.25H), 2.99 (d, J=12.4 Hz, 0.75H), 2.66 (td, J=13.4, 4.8 Hz, 0.75H), 2.50 (td, J=13.6, 4.8 Hz, 0.25H), 2.54-2.29 (m, 2.75H), 2.32-2.20 (m, 0.25H), 2.14-1.97 (m, 1H), 1.53-1.41 (m, 1H), 1.36-1.29 (m, 1H), 0.78 (s, 0.8H), 0.75 (s, 2.2H), 0.73 (s, 2.2H), 0.68 (s, 0.8H). [HPLC Method: Inj. Vol.=5 uL; Start % B=10, 12 Min. 100%; 15 min. 100%; Wavelength 1=220 nm; Wavelength 2=254 nm; Solvent A=0.05% TFA in H$_2$O:MeCN (95:5); Solvent B=0.05% TFA in H$_2$O:MeCN (5:95); Column 1: Sunfire C18 3.5 um, 4.6×150 mm; Retention Time=10.48 min.; Column 2: Xbridge Phenyl 3.5 um, 4.6×150 mm; Retention Time=9.41 min.; Flow=1.0 mL/min on each column.]

Example 97

N-((cis)-2-((S)-4-(4-Chlorophenyl)-4-hydroxy-3,3-dimethylpiperidine-1-carbonyl)cyclobutyl)-3-sulfamoylbenzamide, isomer 2

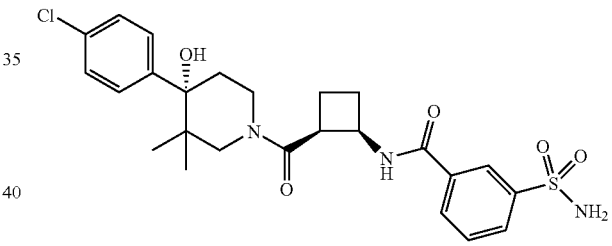

Example 97 was prepared from ((±)-(cis)-2-aminocyclobutyl)((S)-4-(4-chlorophenyl)-4-hydroxy-3,3-dimethylpiperidin-1-yl)methanone, HCl and 3-sulfamoylbenzoic acid using the methods described in Example 96. During preparative HPLC, two diastereomers were separated but isomer 1 was 50% pure and was discarded. Fractions containing the second isomer were combined and freeze-dried to yield Example 97 as a colorless powder. MS (ESI$^+$)=520.3 (M+H)$^+$. $^1$H NMR (CD$_3$OD, 500 MHz) (NMR shows multiple rotamers) δ 8.32 (s, 0.25H), 8.29 (s, 0.75H), 8.09 (d, J=7.2 Hz, 0.25H), 8.06 (d, J=7.7 Hz, 0.75H), 8.02 (d, J=6.6 Hz, 0.25H), 7.96 (d, J=7.7 Hz, 0.75H), 7.72-7.63 (m, 1H), 7.43 (d, J=8.3 Hz, 1.5H), 7.38 (d, J=8.8 Hz, 0.5H), 7.31-7.23 (m, 2H), 5.00 (q, J=7.7 Hz, 0.75H), 4.09 (d, J=12.7 Hz, 0.75H), 4.04-3.97 (m, 0.75H), 3.96-3.89 (m, 0.25H), 3.79 (d, J=13.8 Hz, 0.75H), 3.53 (d, J=13.2 Hz, 0.25H), 3.39-3.32 (m, 1H), 3.18-3.10 (m, 0.5H), 2.99 (d, J=12.7 Hz, 1H), 2.67 (td, J=13.5, 5.0 Hz, 0.75H), 2.58-2.49 (m, 0.25H), 2.48-2.30 (m, 3H), 2.26-2.16 (m, 0.25H), 2.14-2.03 (m, 1H), 1.50 (d, J=13.8 Hz, 0.25H), 1.45 (d, J=13.8 Hz, 0.75H), 0.78 (s, 0.8H), 0.75 (s, 1.2H), 0.73 (s, 1.2H), 0.67 (s, 0.8H). [HPLC Method: Inj. Vol.=5 uL; Start % B=10, 12 Min. 100%; 15 Min. 100%; Wavelength 1=220 nm; Wavelength 2=254 nm; Solvent A=0.05% TFA in H$_2$O:MeCN (95:5); Solvent B=0.05% TFA in H₂O:MeCN (5:95); Column 1: Sunfire C18 3.5 um, 4.6× 150 mm; Retention Time=8.94 min.; Column 2: Xbridge Phenyl 3.5 um, 4.6×150 mm; Retention Time=8.48 min.; Flow=1.0 mL/min on each column.]

Example 98

N-((±)-(cis)-2-((S)-4-(4-Chlorophenyl)-4-hydroxy-3,3-dimethylpiperidine-1-carbonyl)cyclobutyl)cyclopentanecarboxamide

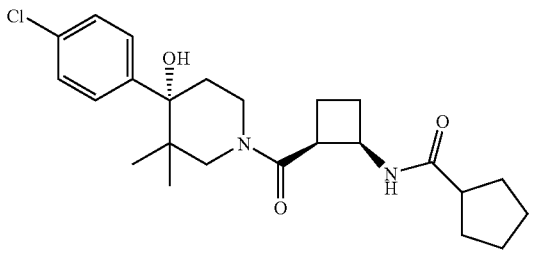 [SMILES: CC1(C)CN(C(=O)[C@H]2CC[C@H]2NC(=O)C2CCCC2)CC[C@]1(O)c1ccc(Cl)cc1]

Example 98 was prepared from ((±)-(cis)-2-aminocyclobutyl)((S)-4-(4-chlorophenyl)-4-hydroxy-3,3-dimethylpiperidin-1-yl)methanone, HCl and cyclopentane carboxylic acid using the methods described in Example 96. Example 98 was isolated as a mixture of the two cis-cyclobutane diastereomers. MS (ESI⁺)=433.3 (M+H)⁺. ¹H NMR (CD₃OD, 500 MHz) (NMR shows multiple rotamers) δ 7.49-7.40 (m, 2H), 7.29 (d, J=8.3 Hz, 2H), 4.79-4.66 (m, 1H), 4.57 (d, J=12.7 Hz, 0.5H), 4.07 (d, J=12.1 Hz, 0.5H), 4.03 (d, J=12.7 Hz, 0.25H), 3.94-3.76 (m, 1.25H), 3.71 (d, J=13.2 Hz, 0.5H), 3.53-3.43 (m, 0.25H), 3.40-3.32 (m, 1H), 3.23 (d, J=13.8 Hz, 0.5H), 3.18-3.00 (m, 1H), 2.70-2.52 (m, 2H), 2.42-2.26 (m, 2H), 2.22-2.06 (m, 1H), 2.04-1.83 (m, 2.5H), 1.83-1.43 (m, 8H), 0.80-0.76 (m, 3H), 0.73 (s, 1H), 0.71 (s, 1.75H), 0.70 (s, 0.25H). [HPLC Method: Inj. Vol.=5 uL; Start % B=10, 12 Min. 100%; 15 Min. 100%; Wavelength 1=220 nm; Wavelength 2=254 nm; Solvent A=0.05% TFA in H₂O:MeCN (95:5); Solvent B=0.05% TFA in H₂O:MeCN (5:95); Column 1: Sunfire C18 3.5 um, 4.6×150 mm; Retention Time=10.11 min.; Column 2: Xbridge Phenyl 3.5 um, 4.6×150 mm; Retention Time=8.99, 9.02 min.; Flow=1.0 mL/min on each column.]

Example 99

(1R,3R)—N-((±)-(cis)-2-((S)-4-(4-Chlorophenyl)-4-hydroxy-3,3-dimethylpiperidine-1-carbonyl)cyclobutyl)-3-hydroxycyclopentanecarboxamide

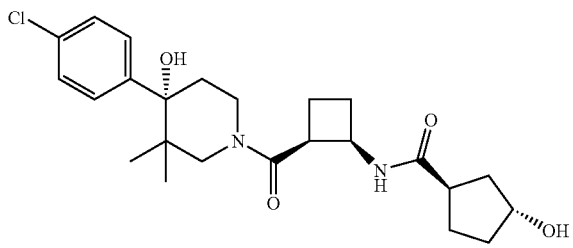 [SMILES: CC1(C)CN(C(=O)[C@H]2CC[C@H]2NC(=O)[C@@H]2CC[C@@H](O)C2)CC[C@]1(O)c1ccc(Cl)cc1]

Example 99 was prepared from ((±)-(cis)-2-aminocyclobutyl)((S)-4-(4-chlorophenyl)-4-hydroxy-3,3-dimethylpiperidin-1-yl)methanone, HCl and sodium (1R,3R)-3-hydroxycyclopentanecarboxylate using the methods described in Example 96. Example 99 was isolated as a mixture of the two cis-cyclobutane diastereomers. MS (ESI⁺)=449.3 (M+H)⁺. ¹H NMR (CD₃OD, 500 MHz) (NMR shows multiple rotamers) δ 7.49-7.40 (m, 2H), 7.31-7.27 (m, 2H), 4.79-4.73 (m, 0.6H), 4.73-4.65 (m, 0.4H), 4.58 (d, J=13.2 Hz, 0.4H), 4.39-4.30 (m, 1H), 4.08 (dd, J=12.7, 1.7 Hz, 0.4H), 4.03 (dd, J=12.7, 1.7 Hz, 0.25H), 3.93-3.86 (m, 0.5H), 3.86-3.76 (m, 0.75H), 3.71 (d, J=13.2 Hz, 0.5H), 3.52-3.42 (m, 0.25H), 3.40-3.32 (m, 0.75H), 3.27-3.20 (m, 0.5H), 3.14-3.01 (m, 1H), 2.99-2.83 (m, 1H), 2.64 (td, J=13.5, 4.4 Hz, 0.5H), 2.57 (td, J=13.5, 5.0 Hz, 0.5H), 2.44-2.24 (m, 2H), 2.20-1.40 (m, 9.5H), 0.81-0.76 (m, 3H), 0.74 (s, 1H), 0.73-0.70 (m, 1.8H), 0.69 (s, 0.2H). [HPLC Method: Inj. Vol.=5 uL; Start % B=10, 12 Min. 100%; 15 Min. 100%; Wavelength 1=220 nm; Wavelength 2=254 nm; Solvent A=0.05% TFA in H₂O:MeCN (95:5); Solvent B=0.05% TFA in H₂O:MeCN (5:95); Column 1: Sunfire C18 3.5 um, 4.6×150 mm; Retention Time=7.53 min.; Column 2: Xbridge Phenyl 3.5 um, 4.6×150 mm; RT=7.23 min.; Flow=1.0 mL/min on each column.]

Example 100

3-((1R,2S)-2-((S)-4-(4-Cyanophenyl)-4-hydroxy-3,3-dimethylpiperidine-1-carbonyl)cyclohexylcarbamoyl)benzoic acid

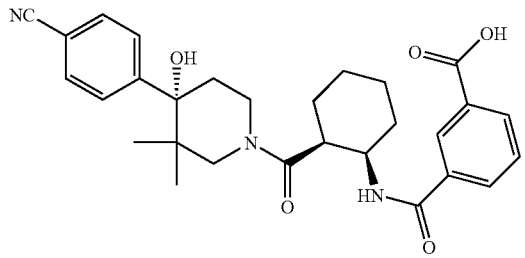

To a solution of 3-((1R,2S)-2-((S)-4-(4-chlorophenyl)-4-hydroxy-3,3-dimethylpiperidine-1-carbonyl)cyclohexylcarbamoyl)benzoic acid (from Example 4, 35 mg, 0.068 mmol) in N-methyl-2-pyrrolidinone (2 ml) and water (0.1 ml) was sequentially added zinc cyanide (8.81 mg, 0.075 mmol), Pd₂(dba)₃ (3.12 mg, 3.41 μmol), and S-Phos (2.80 mg, 6.82 μmol) at RT. Upon completion of addition, the reaction was purged with nitrogen gas, sealed and then heated in a microwave oven at 150° C. for 30 min. At the conclusion of this period, the reaction was purified by preparatory HPLC/MS to yield Example 100 (4.0 mg, 6.48 μmol, 9.49% yield) as a white solid. MS found: (M+H)⁺=504.18. ¹H NMR (CD₃OD, 400 MHz) (NMR shows several rotamers) δ 8.30 (d, 1H, J=8.0 Hz), 8.11 (d, 0.5H, J=8.0 Hz), 8.07 (d, 0.5H, J=8.0 Hz), 7.89 (t, 1H, J=8.0 Hz), 7.61 (app. d, 1H, J=8.0 Hz), 7.58 (app. d, 1H, J=8.0 Hz), 7.55-7.45 (m, 3H), 4.51 (m, 0.5H), 4.34 (m, 0.5H), 4.11 (m, 0.5H), 3.97-3.89 (m, 1H), 3.61-3.47 (m, 1H), 3.33 (t, 3H, J=8 Hz), 3.31-3.25 (m, 1H), 3.06-2.91 (m, 1H), 2.73 (s, 3H), 2.72-2.65 (m, 0.5H), 2.53-2.31 (m, 1H), 2.26 (t, 2H, J=8 Hz), 2.14-2.03 (m, 0.5H), 2.01-1.80 (m, 2H), 1.80-1.77 (m, 0.5H), 1.77-1.62 (m, 3.5H), 1.62-1.32 (m, 3.5H), 0.68 (s, 0.5×3H), 0.67 (s, 0.5×3H), 0.66 (s, 0.5×3H), 0.58 (s, 0.5×3H). [LCMS method: Inj. Vol.=10 uL: Start % B=0; Final % B=100; Gradient Time=2 min; Flow Rate=5 ml/min; Wavelength=220 nm; Solvent A=10% MeOH-90% H₂O-0.1% TFA; Solvent B=90% MeOH-10% H₂O-0.1% TFA; Column 1=Waters Sunfire S5 C18 4.6×50 mm (2 min. grad); Retention Time=1.72 minutes.]

Example 101

Example 101, as described in Table 2, was prepared in a similar manner as described for the preparation of Example 100. The data in the "MS" column represents the values observed for the (M+H)⁺ ions in MS experiments.

TABLE 2

| Example | Structure | Mass Spec (M + H)+ |
|---|---|---|
| 101 | 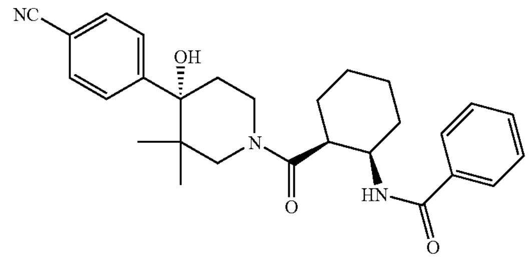 | 460 |

Examples 102 and 103

N-((1R,2S)-2-((S)-4-(4-Chlorophenyl)-4-hydroxy-3,3-dimethylpiperidine-1-carbonyl)-1-methylcyclopentyl)benzamide and N-((1S,2R)-2-((S)-4-(4-chlorophenyl)-4-hydroxy-3,3-dimethylpiperidine-1-carbonyl)-1-methylcyclopentyl)benzamide

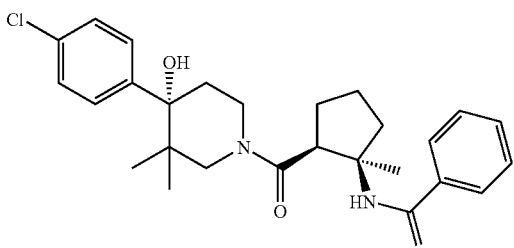

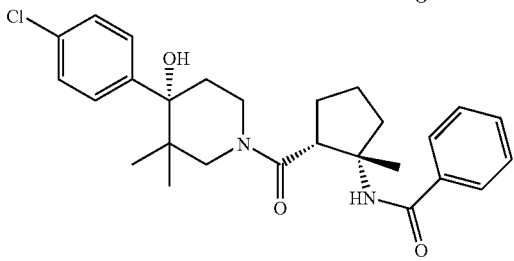

Step 1: tert-Butyl (1R,2S)-2-((S)-4-(4-chlorophenyl)-4-hydroxy-3,3-dimethylpiperidine-1-carbonyl)-1-methylcyclopentylcarbamate and tert-Butyl (1S,2R)-2-((S)-4-(4-chlorophenyl)-4-hydroxy-3,3-dimethylpiperidine-1-carbonyl)-1-methylcyclopentylcarbamate, respectively

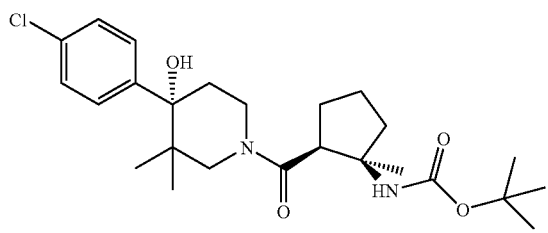

-continued

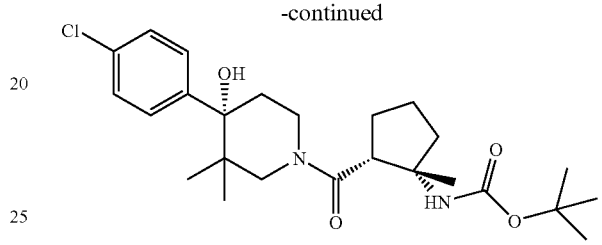

(S)-4-(4-Chlorophenyl)-3,3-dimethylpiperidin-4-ol, (246 mg, 1.028 mmol), cis- and trans-(1S,2R)-2-(tert-butoxycarbonylamino)-2-methylcyclopentanecarboxylic acid (250 mg, 1.028 mmol), HOBt (189 mg, 1.233 mmol), EDC (236 mg, 1.233 mmol) and triethylamine (0.286 ml, 2.055 mmol) were mixed in dichloromethane (20 ml) at 25° C. with stirring for 20 hours. The reaction mixture was worked-up by adding methylene chloride and then rinsing with saturated sodium carbonate (1×). The methylene chloride layer was dried over sodium sulfate and stripped to give an amber glass. The amber glass was purified over silica gel (using 9:1 to 3:1 to 1:1 hexanes/EtOAc to 100% EtOAc) to yield 450 mg of a white glass as a mixture of two cis-diastereomer products. The two cis-diastereomers were isolated by Supercritical Fluid Chromatography. Peak 1 gave tert-butyl (1R,2S)-2-((S)-4-(4-chlorophenyl)-4-hydroxy-3,3-dimethylpiperidine-1-carbonyl)-1-methylcyclopentylcarbamate (210 mg, 0.452 mmol, 43.9% yield) as a white glass and it was labeled as Isomer A. MS found: (M+H)+=465.29. Peak 2 gave tert-butyl (1S,2R)-2-((S)-4-(4-chlorophenyl)-4-hydroxy-3,3-dimethylpiperidine-1-carbonyl)-1-methylcyclopentylcarbamate (200 mg, 0.430 mmol, 41.9% yield) as a white glass and it was labeled as Isomer B. MS found: (M+H)+=465.29.

Step 2A: ((1R,2S)-2-Amino-2-methylcyclopentyl)((S)-4-(4-chlorophenyl)-4-hydroxy-3,3-dimethylpiperidin-1-yl)methanone, HCl

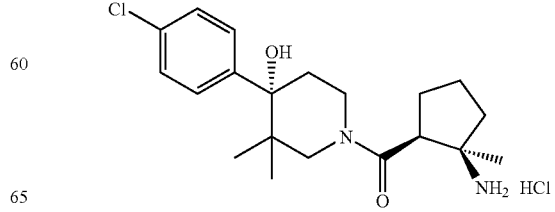

tert-Butyl (1R,2S)-2-((S)-4-(4-chlorophenyl)-4-hydroxy-3,3-dimethylpiperidine-1-carbonyl)-1-methylcyclopentyl-carbamate (Isomer A from Step 1, 205 mg, 0.441 mmol) was dissolved in dioxane (4 ml) at 60° C. with stirring and then 4N HCl in dioxane (0.551 ml, 2.204 mmol) was added. Upon completion of addition, the reaction was stirred for 3 hours. After this time, the reaction was analyzed by LC/MS, which indicated the desired product with an (M+H)$^+$=365.28. Methylene chloride was added to the reaction and then the reaction was worked-up by stripping the reaction from methylene chloride (5×) to obtain the title compound (160 mg, 0.399 mmol, 90% yield) as a white glass.

Step 2B: ((1S,2R)-2-Amino-2-methylcyclopentyl)((S)-4-(4-chlorophenyl)-4-hydroxy-3,3-dimethylpiperidin-1-yl)methanone, HCl

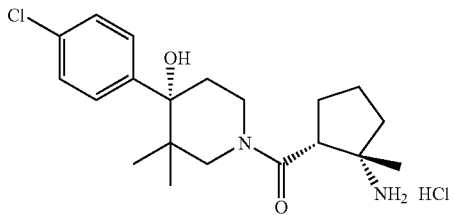 [SMILES: CC1(C)CN(C(=O)[C@@H]2CCC[C@]2(C)N)CC[C@]1(O)c1ccc(Cl)cc1 ; Cl]

The title compound was prepared was prepared in a similar manner as described in Step 2A set forth above using tert-butyl (1S,2R)-2-((S)-4-(4-chlorophenyl)-4-hydroxy-3,3-dimethylpiperidine-1-carbonyl)-1-methylcyclopentylcarbamate (Isomer B from Step 1, 195 mg, 0.419 mmol), dioxane (4 ml), and 4N HCl in dioxane (0.524 ml, 2.097 mmol). The title compound (150 mg, 0.374 mmol, 89% yield) was obtained as a white glass.

Step 3A: Example 102

((1R,2S)-2-Amino-2-methylcyclopentyl)((S)-4-(4-chlorophenyl)-4-hydroxy-3,3-dimethylpiperidin-1-yl)methanone, HCl (from Step 2A above, 25 mg, 0.062 mmol), benzoic acid (7.61 mg, 0.062 mmol), HOBt (11.45 mg, 0.075 mmol), EDC (14.33 mg, 0.075 mmol) and triethylamine (0.017 ml, 0.125 mmol) were mixed in methylene chloride (3 ml) at 25° C. with stirring for 20 hours. The reaction was worked-up by adding methylene chloride and then rinsing with saturated sodium carbonate (1×). The methylene chloride layer was dried over sodium sulfate and stripped to give a colorless oil. The colorless oil was purified by preparative HPLC/MS to yield Example 102 (18 mg, 0.031 mmol, 61.9% yield) as a white solid. MS found: (M+H)$^+$=469.16. $^1$H NMR (CD$_3$OD, 400 MHz) (NMR shows several rotamers) δ 9.32 (s, 0.25H), 9.12 (s, 0.25H), 7.79 (m, 2H), 7.58-7.40 (m, 5H), 7.35-7.26 (m, 2H), 4.68 (m, 0.5H), 4.23-4.15 (m, 1H), 3.72-3.60 (m, 1.5H), 3.38-3.33 (m, 1H), 3.25-3.10 (m, 1.5H), 3.02-2.86 (s, 1H), 2.74-2.56 (m, 1H), 2.22-1.94 (m, 2H), 1.90-1.75 (m, 2H), 1.74-1.64 (m, 1H), 1.67 (s, 0.5×3H), 1.63-1.50 (m, 1H), 1.55 (s, 0.5×3H), 0.85 (s, 0.5×3H), 0.80 (s, 0.5×3H), 0.79 (s, 0.5×3H), 0.70 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.33 minutes.]

Step 3B: Example 103

(1S,2R)-2-Amino-2-methylcyclopentyl)((S)-4-(4-chlorophenyl)-4-hydroxy-3,3-dimethylpiperidin-1-yl)methanone, HCl (from Step 2B above, 25 mg, 0.069 mmol), benzoic acid (8.37 mg, 0.069 mmol), HOBt (12.59 mg, 0.082 mmol), EDC (15.76 mg, 0.082 mmol) and triethylamine (0.019 ml, 0.137 mmol) were mixed in methylene chloride (3 ml) at 25° C. with stirring for 20 hours. After this time, the reaction was worked-up by adding methylene chloride and then rinsing with saturated sodium carbonate (1×). The methylene chloride layer was dried over sodium sulfate and stripped to give a colorless oil. The colorless oil was purified by preparative HPLC/MS to yield Example 103 (12 mg, 0.021 mmol, 37.0% yield) as a white solid. MS found: (M+H)$^+$=469.14. $^1$H NMR (CD$_3$OD, 400 MHz) (NMR shows several rotamers) δ 10.15 (s, 0.25H), 9.30 (s, 0.25H), 7.83 (d, 2H, J=8 Hz), 7.78 (d, 2H, J=8 Hz), 7.56-7.42 (m, 5H), 7.35-7.29 (m, 2H), 4.65 (m, 0.5H), 4.22-4.15 (m, 1H), 3.68 (m, 0.5H), 3.59 (s, 1H), 3.20-3.04 (m, 2H), 3.04-2.94 (s, 0.5H), 2.78-2.60 (m, 1H), 2.24-2.07 (m, 1.5H), 1.99-1.75 (m, 2.5H), 1.72-1.65 (m, 2H), 1.56 (s, 0.5×3H), 1.55 (s, 0.5×3H), 0.86 (s, 0.5×3H), 0.85 (s, 0.5×3H), 0.82 (s, 0.5×3H), 0.76 (s, 0.5×3H). [LCMS method: Inj. Vol.=10 uL; Start % B=0; Final % B=100; Gradient Time=2 min; Flow Rate=4 ml/min; Wavelength=220 nm; Solvent A=10% MeOH-90% H$_2$O-0.1% TFA; Solvent B=90% MeOH-10% H$_2$O-0.1% TFA; Column 1=Waters Sunfire C18 4.6×50 mm (4 min. grad); Retention Time=2.35 minutes.]

Example 104

Example 104, as described in Table 3, was prepared in a similar manner as described for the preparation of Examples 102 and 103. The data in the "MS" column represents the values observed for the (M+H)$^+$ ions in MS experiments.

TABLE 3

| Example | Structure | Mass Spec (M + H)$^+$ |
|---|---|---|
| 104 | 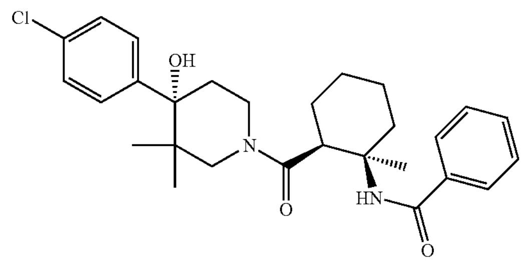 [SMILES: CC1(C)CN(C(=O)[C@H]2CCCC[C@@]2(C)NC(=O)c2ccccc2)CC[C@]1(O)c1ccc(Cl)cc1] | 483 |

Example 105

1-((1R,2S)-2-((S)-4-(4-Chlorophenyl)-4-hydroxy-3,3-dimethylpiperidine-1-carbonyl)cyclopentyl)-3-((S)-3-hydroxy-3-methylbutan-2-yl)urea

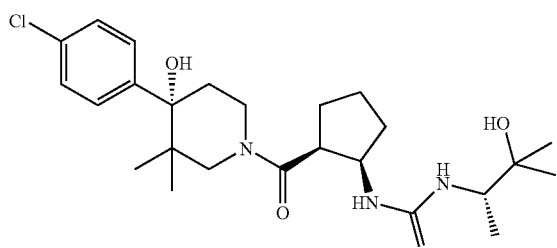

Step 1: (S)-tert-Butyl 3-hydroxy-3-methylbutan-2-ylcarbamate

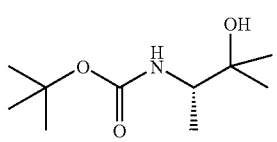

To a colorless solution of (S)-methyl 2-(tert-butoxy carbonylamino)propanoate (2.0 g, 9.84 mmol) in THF (14 mL) at 0° C. was added 3.0M CH₃MgBr (13.97 mL, 41.9 mmol) dropwise via an addition funnel during a 10 minute period, during which time the solution turned yellow then colorless with white solids present. Upon completion of addition, the reaction mixture was allowed to warm to RT where it stirred overnight. After this time, under a nitrogen atmosphere, the reaction mixture was carefully worked-up by slowly adding dropwise saturated ammonium chloride (25 ml). Gas evolution and foaming were observed. Upon completion of addition, the resulting suspension became a solution, which was extracted (2×) with methylene chloride. The organic layers were combined, dried over sodium sulfate and then concentrated to yield the title compound (2.00 g, 9.84 mmol, 100% yield) as a colorless oil. MS found: (M+H–t-butyl)⁺=148.06.

Step 2: (S)-3-Amino-2-methylbutan-2-ol.HCl

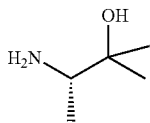

(S)-tert-Butyl 3-hydroxy-3-methylbutan-2-ylcarbamate (2.00 g, 9.84 mmol) was dissolved in dioxane (5 mL) at 25° C. with stirring under nitrogen and then 4N HCl in dioxane (7.38 mL, 29.5 mmol) was added, followed by 1 ml of t-butanol. Upon completion of addition, the reaction was stirred for 3 hours during which time some solids precipitated and the reaction became darker in color. The reaction mixture was analyzed by LC/MS, which indicated that the reaction was essentially complete, judged by the lack of the 148 mass for starting material minus t-butyl. Et₂O (50 ml) was added to the reaction mixture. Upon completion of addition, the reaction mixture was stirred for 10 minutes. The resulting solids were collected by filtration and then quickly concentration under high vacuum to yield the title compound (1.19 g, 8.52 mmol, 87% yield) as a tan solid.

Step 3: Phenyl (1R,2S)-2-((S)-4-(4-Chlorophenyl)-4-hydroxy-3,3-dimethylpiperidine-1-carbonyl)cyclopentylcarbamate

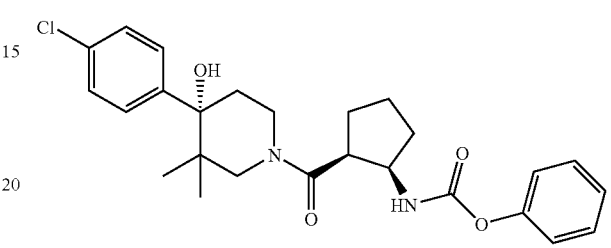

((1S,2R)-2-Aminocyclopentyl)((S)-4-(4-chlorophenyl)-4-hydroxy-3,3-dimethylpiperidin-1-yl)methanone, HCl (see Example 8, Step 1, 90 mg, 0.232 mmol) and triethylamine (0.032 mL, 0.232 mmol) were mixed in methylene chloride (5 mL) at 25° C. with stirring and then cooled to 0° C. Once at the prescribed temperature, a solution of phenyl carbonochloridate (36.4 mg, 0.232 mmol) in 2 mL of methylene chloride was added dropwise. Upon completion of addition, the reaction was stirred for 30 minutes. After this time, the reaction was worked-up by rinsing with 1N HCl (1×) followed by saturated sodium bicarbonate (1×). The organic layer was dried over sodium sulfate and stripped to give a white glass. The white glass was purified over silica gel (in 3:1 to 1:1 hexanes/EtOAc to 100% EtOAc) to yield the title compound (90 mg, 0.191 mmol, 82% yield) as a white glass. MS found: (M+H)⁺=471.18.

Step 4: Example 105

Phenyl (1R,2S)-2-((S)-4-(4-chlorophenyl)-4-hydroxy-3,3-dimethylpiperidine-1-carbonyl)cyclopentylcarbamate (30 mg, 0.064 mmol), (S)-3-amino-2-methylbutan-2-ol.HCl (from Step 2) (8.89 mg, 0.064 mmol) and Hunig's base (0.011 mL, 0.064 mmol) were mixed in acetonitrile (3 mL) at RT and then microwaved at 140° C. for 1 hour. After this time, the reaction was concentrated and then purified by preparative HPLC/MS. The resulting MeOH/water mixture was stripped to dryness and then methylene chloride was added. Upon completion of addition, the mixture was dried with sodium sulfate and then stripped to yield Example 105 (20 mg, 0.042 mmol, 65.4% yield) as a white solid. MS found: (M+H–t-butyl)⁺=480.17. ¹H NMR (CD₃OD, 400 MHz) (NMR shows several rotamers) δ 7.46 (d, 1.5H, J=8.0 Hz), 7.42 (d, 0.5H, J=8.0 Hz), 7.29 (d, 2H, J=8.0 Hz), 4.57 (m, 0.5H), 4.42 (q, 0.75H, J=8 Hz), 4.26 (q, 0.25H, J=8 Hz), 4.06-3.97 (m, 2H), 3.66-3.32 (m, 3.5H), 3.14-3.00 (m, 1H), 2.70 (m, 0.75H), 2.52 (m, 0.25H), 2.18-2.06 (m, 1H), 2.06-1.72 (m, 4H), 1.68-1.55 (m, 2H), 1.58-1.47 (m, 1H), 1.20-1.13 (m, 6H), 1.12-1.06 (m, 3H), 0.82-0.70 (m, 6H). [LCMS method: Inj. Vol.=10 uL; Start % B=0; Final % B=100; Gradient Time=2 min; Flow Rate=5 ml/min; Wavelength=220 nm; Solvent A=10% MeOH-90% H₂O-0.1% TFA; Solvent B=90%

MeOH-10% H$_2$O-0.1% TFA; Column 1=Waters Sunfire S5 C18 4.6×50 mm (2 min. grad); Retention Time=1.78 minutes.]

Example 106

Example 106, as described in Table 4, was prepared in a similar manner as described for the preparation of Example 105. The data in the "MS" column represents the values observed for the (M+H)$^+$ ions in MS experiments.

TABLE 4

| Example | Structure | Mass Spec (M + H)$^+$ |
|---|---|---|
| 106 | [chemical structure] | 494 |

UTILITY

In general, compounds of the present invention, such as particular compounds disclosed in the preceding examples, have been shown to be modulators of chemokine receptor activity. By displaying activity as modulators of chemokine receptor activity, compounds of the present invention are expected to be useful in the treatment of human diseases associated with chemokines and their cognate receptors.

CCR1 Ligand Binding Scintillation Proximity Assay (SPA)

For radioligand competition studies, a final concentration of 1×10$^5$ THP-1 monocytic leukemia cells are combined with 100 μg of LS WGA PS beads (Amersham, Cat.#: RPNQ 0260) in 40 μl of assay buffer (RPMI 1640 without phenol red, 50 mM HEPES, 5 mM MgCl$_2$, 1 mM CaCl$_2$, 0.1% BSA). The THP-1 cell/bead mixture is added to each well of a 384-well assay plate (PerkinElmer, Cat. #:6007899) containing test compound in 3-fold serial dilution, with final concentrations ranging from 8 μM to 140 μM. A final concentration of 0.1 nM [$^{125}$I]-MIP-1α (PerkinElmer, Cat. # NEX298) in 20 μl assay buffer is added to the reaction. Sealed assay plates are incubated at room temperature for 12 h then analyzed by LEADseeker™.

The competition data of the test compound over a range of concentrations is plotted as percentage inhibition of radioligand specific bound in the absence of test compound (percent of total signal). After correcting for non-specific binding, IC$_{50}$ values are determined. The IC$_{50}$ value is defined as the concentration of test compound needed to reduce [$^{125}$I]-MIP-1α specific binding by 50% and is calculated using the four parameter logistic equation to fit the normalized data. The Ki values are determined by application of the Cheng-Prusoff equation to the IC$_{50}$ values, where K$_i$=IC$_{50}$/(1+ ligand concentration/K$_d$) The Kd of [$^{125}$I]-MIP-1α in THP-1 cells is 0.1 nM. Each experiment is run in duplicate.

Compounds of the present invention were tested in the assay described immediately above and the results shown in Table 5 below were obtained.

TABLE 5

| Example | CCR1 IC$_{50}$ (nM) | Replicates* |
|---|---|---|
| 2 | 2.1 | 2 |
| 7 | 12.1 | 1 |
| 9 | 11.5 | 1 |
| 10 | 1065 | 1 |
| 11 | 17.2 | 1 |
| 35 | 18.5 | 1 |

TABLE 5-continued

| Example | CCR1 IC$_{50}$ (nM) | Replicates* |
|---|---|---|
| 41 | 996.7 | 2 |
| 57 | 18.7 | 1 |
| 58 | 931.8 | 1 |
| 60 | 15.7 | 1 |
| 61 | 767.5 | 1 |
| 67 | 857.8 | 1 |
| 68 | 580.6 | 1 |
| 76 | 14.6 | 1 |
| 80 | 1.0 | 1 |
| 83 | 14.0 | 1 |
| 84 | 1.5 | 1 |
| 85 | 1.6 | 1 |
| 86 | 1.3 | 1 |
| 89 | 1.8 | 1 |
| 100 | 11.3 | 1 |
| 104 | 818 | 1 |
| 106 | 0.7 | 1 |

*number of individual assay determinations

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjögren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

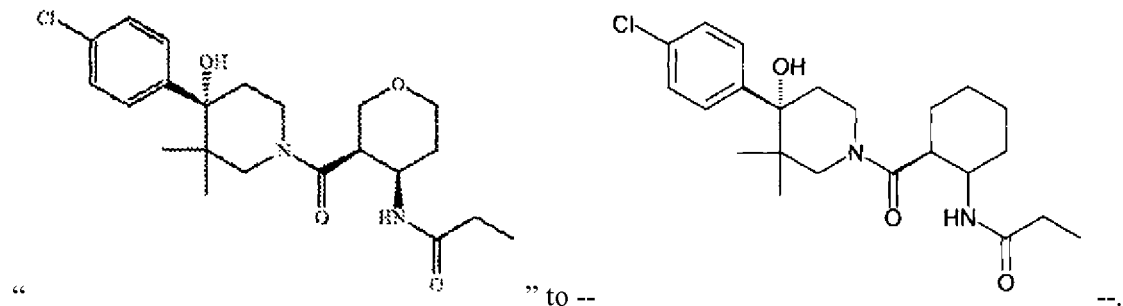

What is claimed is:
1. A compound of Formula (I):

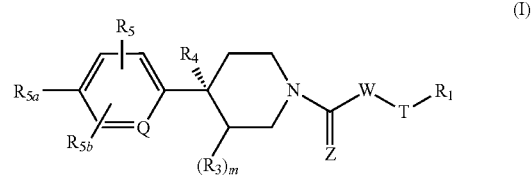

or a stereoisomer or pharmaceutically acceptable salt thereof, wherein:
Q is CH or N;
Z is O or S;
W is

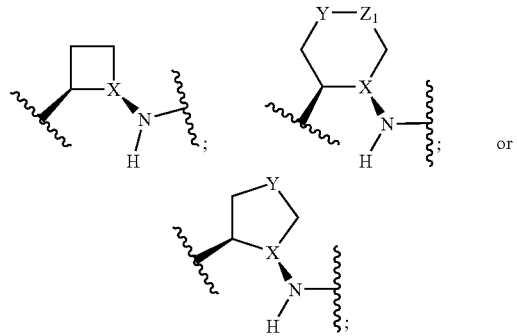

X is $C(R_8)$;
Y is $CH(R_{1a})$, $CH_2$, O, S, S(O), $S(O)_2$, $N(R_8)$, $C(=O)$ or

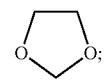

$Z_1$ is $CH(R_7)$, $CH_2$, O, S, $N(R_8)$, S(O) or $S(O)_2$;
T is a bond,

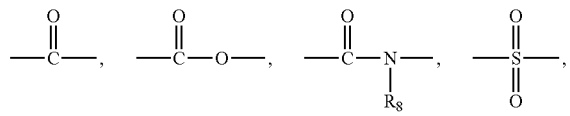

-continued

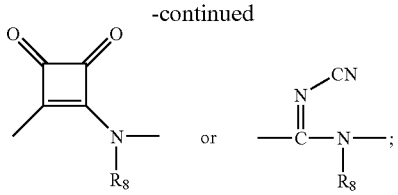

R$_1$ is alkyl, cycloalkyl, aryl, heterocyclyl or heteroaryl, all of which may be optionally substituted with 0-5 R$_{1a}$; provided that R$_1$ is not unsubstituted phenyl when T is

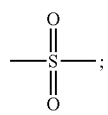

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is F, OH, CN or —NH$_2$;

R$_5$ is hydrogen, halo, —CN or -Oalkyl;

R$_{5a}$ is hydrogen, halo, —CN or alkynyl;

R$_{5b}$ is hydrogen, halo, —CN or -Oalkyl;

R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 2;

r is 0-5;

provided that:

(1) R$_5$, R$_{5a}$ and R$_{5b}$ are not all H when T is a bond and R$_4$ is OH.

2. The compound of claim 1, or a stereoisomer or pharmaceutically acceptable salt thereof, wherein the compound is a compound of formula (Ia):

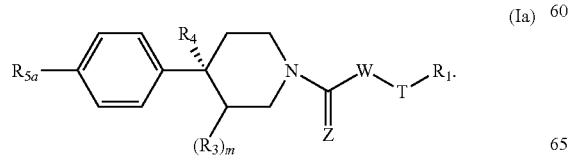

(Ia)

3. The compound of claim 1, or a stereoisomer or pharmaceutically acceptable salt thereof, wherein:

Z is O or S;

W is

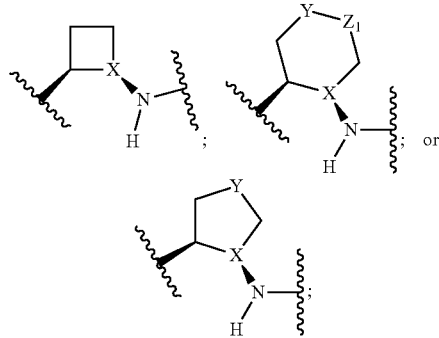

X is C(R$_8$);

Y is CH(R$_{1a}$), CH$_2$, O, S, S(O), S(O)$_2$, N(R$_8$), C(=O) or

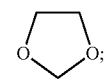

Z$_1$ is CH(R$_7$), CH$_2$, O, S, N(R$_8$), S(O) or S(O)$_2$;

T is

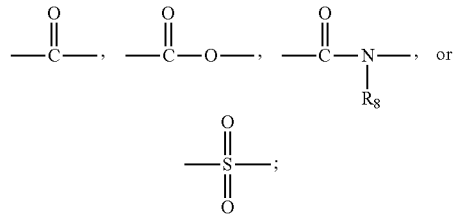

R$_1$ is alkyl, cycloalkyl, aryl, heterocyclyl or heteroaryl, all of which may be optionally substituted with 0-5 R$_{1a}$; provided that R$_1$ is not unsubstituted phenyl when T is

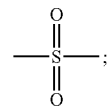

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_4$ is F, OH, CN or —NH$_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 2; and r is 0-4.

4. The compound of claim 1, or a stereoisomer or pharmaceutically acceptable salt thereof, wherein:

Z is O or S;
W is

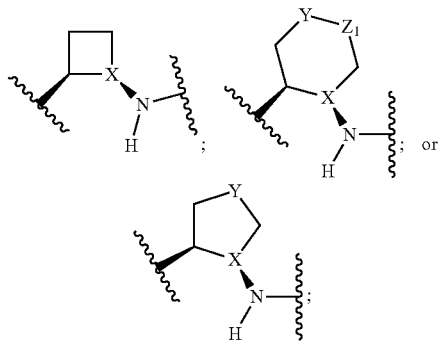

X is C($R_8$);
Y is CH($R_{1a}$), $CH_2$, O, S, $S(O)_2$, N($R_8$), C(=O) or

$Z_1$ is CH($R_7$), $CH_2$, O, S, N($R_8$) or $S(O)_2$;
T is

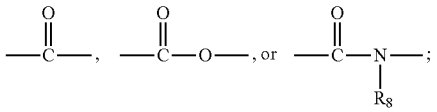

$R_1$ is alkyl, cycloalkyl, aryl, heterocyclyl or heteroaryl, all of which may be optionally substituted with 0-5 $R_{1a}$;
$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)N$R_9R_9$, —N$R_9R_9$, —S(O)$_2$N$R_9R_9$, —N$R_9$S(O)$_2$($CF_2$)$_r$$CF_3$, —C(=O)N$R_9$S(O)$_2R_6$, —S(O)$_2$N$R_9$C(=O)O$R_6$, —S(O)$_2$N$R_9$C(=O)N$R_9R_9$, —C(=O)N$R_9$S(O)$_2$($CF_2$)$_r$$CF_3$, —C(=O)($CR_8R_8$)$_r$$R_{10}$, —N$R_9$C(=O)H, —N$R_9$C(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —N$R_9$C(=O)O$R_6$, —N$R_9$S(O$_2$)$R_6$, =O, —OC(=O)N$R_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O($CR_8R_8$)$_r$$R_{10}$, —OH, —SH, —C(=O)N$R_{14}R_{14}$, —S(O)$_2$N$R_{14}R_{14}$, —C(=O)N$R_{14}$S(O)$_2R_6$, —S(O)$_2$N$R_{14}$C(=O)O$R_6$, —S(O)$_2$N$R_{14}$C(=O)N$R_{14}R_{14}$, —C(=O)N$R_{14}$S(O)$_2$($CF_2$)$_r$$CF_3$, —C(=O)($CR_8R_8$)$_r$$R_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)N$R_9R_9$, —N$R_9R_9$, —S(O)$_2$N$R_9R_9$, —N$R_9$S(O)$_2$($CF_2$)$_r$$CF_3$, —C(=O)N$R_9$S(O)$_2R_6$, —S(O)$_2$N$R_9$C(=O)O$R_6$, —S(O)$_2$N$R_9$C(=O)N$R_9R_9$, —C(=O)N$R_9$S(O)$_2$($CF_2$)$_r$$CF_3$, —C(=O)($CR_8R_8$)$_r$$R_{10}$, —N$R_9$C(=O)H, —N$R_9$C(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —N$R_9$C(=O)O$R_6$, —N$R_9$S(O$_2$)$R_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_4$ is F, OH, CN or —$NH_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —C(=O)N$R_9R_9$, —N$R_9R_9$, —S(O)$_2$N$R_9R_9$, —N$R_9$S(O)$_2$($CF_2$)$_r$$CF_3$, —C(=O)N$R_9$S(O)$_2R_6$, —S(O)$_2$N$R_9$C(=O)O$R_6$, —S(O)$_2$N$R_9$C(=O)N$R_9R_9$, —C(=O)N$R_9$S(O)$_2$($CF_2$)$_r$$CF_3$, —C(=O)($CR_8R_8$)$_r$$R_{10}$, —N$R_9$C(=O)H, —N$R_9$C(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —N$R_9$C(=O)O$R_6$, —N$R_9$S(O$_2$)$R_6$, =O, —OC(=O)N$R_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)N$R_9R_9$, —N$R_9R_9$, —S(O)$_2$N$R_9R_9$, —N$R_9$S(O)$_2$($CF_2$)$_r$$CF_3$, —C(=O)N$R_9$S(O)$_2R_6$, —S(O)$_2$N$R_9$C(=O)O$R_6$, —S(O)$_2$N$R_9$C(=O)N$R_9R_9$, —C(=O)N$R_9$S(O)$_2$($CF_2$)$_r$$CF_3$, —C(=O)($CR_8R_8$)$_r$$R_{10}$, —N$R_9$C(=O)H, —N$R_9$C(=O)($CR_8R_8$)$_r$$R_{10}$, —OC(=O)($CR_8R_8$)$_r$$R_{10}$, —S(=O)($CR_8R_8$)$_r$$R_{10}$, —S(O)$_2$($CR_8R_8$)$_r$$R_{10}$, —N$R_9$C(=O)O$R_6$, —N$R_9$S(O$_2$)$R_6$, aryloxy, arylalkyl or arylalkyloxyalkyl;

$R_8$, at each occurrence, is independently hydrogen or alkyl;
$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{14}$, at each occurrence, is independently selected from hydrogen, alkyl, cycloalkyl or phenyl;

m is 2; and r is 0-3.

5. The compound of claim 1, or a stereoisomer or pharmaceutically acceptable salt thereof, wherein:

Z is O;

W is

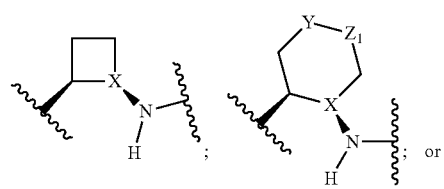

-continued

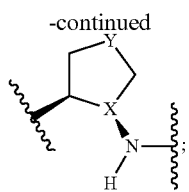

X is C(R$_8$);
Y is CH(R$_{1a}$), CH$_2$, O, S, S(O)$_2$, N(R$_8$) or C(=O);
$Z_1$ is CH(R$_7$), CH$_2$, O, S or N(R$_8$);
T is

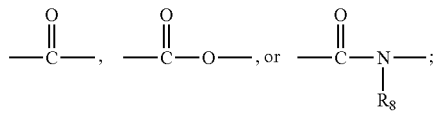

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or aryalkyloxyalkyl;

$R_3$, at each occurrence, is independently OH or alkyl; or two $R_3$'s together with the carbon atom to which they are attached may form a 3- to 6-membered ring;

$R_4$ is F, OH, or —$NH_2$;

$R_5$ is hydrogen, halo or —CN;

$R_{5a}$ is halo, —CN or alkynyl;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C(=O)OR_6$, —S$(O)_2NR_9C(=O)NR_9R_9$, —C(=O)$NR_9S(O)_2(CF_2)_rCF_3$, —C(=O)$(CR_8R_8)_rR_{10}$, —$NR_9C(=O)H$, —$NR_9C(=O)(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C(=O)OR_6$, —$NR_9S(O_2)R_6$, =O, —OC(=O)$NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —S$(O)_3H$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C(=O)OR_6$, —S$(O)_2NR_9C(=O)NR_9R_9$, —C(=O)$NR_9S(O)_2(CF_2)_rCF_3$, —C(=O)$(CR_8R_8)_rR_{10}$, —$NR_9C(=O)H$, —$NR_9C(=O)(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C(=O)OR_6$, —$NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O$(CR_8R_8)_rR_{10}$, —OH, —SH, —C(=O)$NR_{14}R_{14}$, —S$(O)_2NR_{14}R_{14}$, —C(=O)$NR_{14}S(O)_2R_6$, —S$(O)_2NR_{14}C(=O)OR_6$, —S$(O)_2NR_{14}C(=O)NR_{14}R_{14}$, —C(=O)$NR_{14}S(O)_2(CF_2)_rCF_3$, —C(=O)$(CR_8R_8)_rR_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S$(O)_3H$, —C(=O)$NR_{14}R_{14}$, —$NR_{14}R_{14}$, —S$(O)_2NR_{14}R_{14}$, —$NR_{14}S(O)_2(CF_2)_rCF_3$, —C(=O)$NR_{14}S(O)_2R_6$, —S$(O)_2NR_{14}C(=O)OR_6$, —S$(O)_2NR_{14}C(=O)NR_{14}R_{14}$, —C(=O)$NR_{14}S(O)_2(CF_2)_rCF_3$, —C(=O)$(CR_8R_8)_rR_{14}$, —$NR_{14}C(=O)H$, —$NR_{14}C(=O)(CR_8R_8)_rR_{14}$, —OC(=O)$(CR_8R_8)_rR_{14}$, —S(=O)$(CR_8R_8)_rR_{14}$, —S$(O)_2(CR_8R_8)_rR_{14}$, —$NR_{14}C(=O)OR_6$, —$NR_{14}S(O_2)R_6$, —OC(=O)$NR_{14}R_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S$(O)_3H$, —C(=O)$NR_{14}R_{14}$, —$NR_{14}R_{14}$, —S$(O)_2NR_{14}R_{14}$, —$NR_{14}S(O)_2(CF_2)_rCF_3$, —C(=O)$NR_{14}S(O)_2R_6$, —S$(O)_2NR_{14}C(=O)OR_6$, —S$(O)_2NR_{14}C(=O)NR_{14}R_{14}$, —C(=O)$NR_{14}S(O)_2(CF_2)_rCF_3$, —C(=O)$(CR_8R_8)_rR_{14}$, —$NR_{14}C(=O)H$, —$NR_{14}C(=O)(CR_8R_8)_rR_{14}$, —OC(=O)$(CR_8R_8)_rR_{14}$, —S(=O)$(CR_8R_8)_rR_{14}$, —S$(O)_2(CR_8R_8)_rR_{14}$, —$NR_{14}C(=O)OR_6$, —$NR_{14}S(O_2)R_6$, —OC(=O)$NR_{14}R_{14}$, aryloxy or arylalkyl;

$R_{14}$, at each occurrence, is independently selected from hydrogen, alkyl, cycloalkyl or phenyl;

m is 2; and r is 0-2.

6. The compound of claim 1, or a stereoisomer or pharmaceutically acceptable salt thereof, wherein:

Z is O;

W is

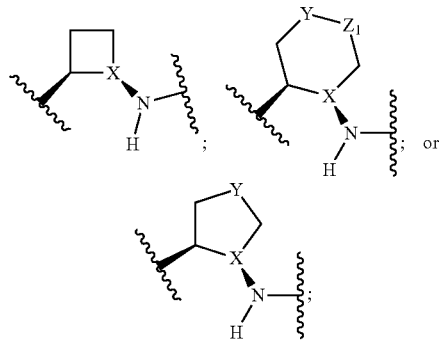

X is $C(R_8)$;

Y is $CH(R_{1a})$, $CH_2$, O, S, $S(O)_2$, $N(R_8)$, or C(=O);

$Z_1$ is $CH(R_7)$, $CH_2$, O or $N(R_8)$;

T is

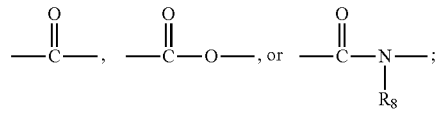

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$; or any two $R_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_3$, at each occurrence, is independently OH or alkyl; or two $R_3$'s together with the carbon atom to which they are attached may form a 3- to 6-membered ring;

$R_4$ is F, OH, or —NH$_2$;

$R_5$ is hydrogen, halo or —CN;

$R_{5a}$ is halo or —CN;

$R_{5b}$ is hydrogen, halo or —CN;

$R_6$, at each occurrence, is independently alkyl, cycloalkyl, cycloalkylalkyl, aryl, arylalkyl, heteroaryl or heteroarylalkyl;

$R_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or any two $R_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=)NR$_{14}$R$_{14}$, aryloxy or arylalkyl;

R$_{14}$, at each occurrence, is independently selected from hydrogen, alkyl, cycloalkyl or phenyl;

m is 2; and r is 0-2.

7. The compound of claim 1, or a stereoisomer or pharmaceutically acceptable salt thereof, wherein:

Z is O;

W is

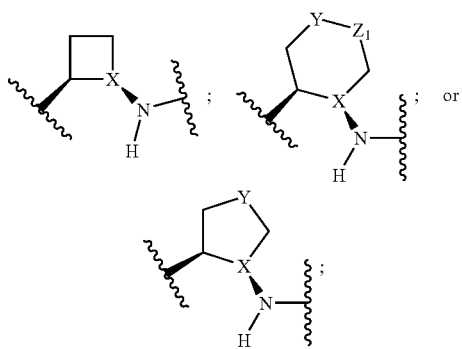

X is C(R$_8$);
Y is CH(R$_{1a}$), CH$_2$, O, S or S(O)$_2$;
Z$_1$ is CH(R$_7$), CH$_2$ or O;
T is

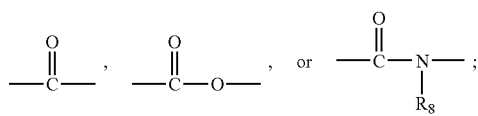

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$; —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$; or any two R$_{1a}$'s attached to the same carbon atom may form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is F, OH, or —NH$_2$;

R$_5$ is hydrogen, halo or —CN;

R$_{5a}$ is halo or —CN;

R$_{5b}$ is hydrogen, halo or —CN;

R$_6$, at each occurrence, is independently alkyl, cycloalkyl, cycloalkylalkyl, aryl, arylalkyl, heteroaryl or heteroarylalkyl;

R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;

R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S; or any two R$_9$'s may be taken to form a 3- to 6-membered ring, wherein the carbon atoms of said ring may be optionally replaced with a heteroatom selected from N, O, and S and the N heteroatom of said ring may be optionally substituted with one or more of the following: hydrogen, alkyl, haloalkyl, aryl, alkenyl, alkynyl, cycloalkyl, cycloalkylalkyl, heteroaryl, heteroarylalkyl, heterocyclyl, heterocyclylalkyl, —C(=O)O(CR$_8$R$_8$)$_r$R$_{10}$, —OH, —SH, —C(=O)NR$_{14}$R$_{14}$, —S(O)$_2$NR$_{14}$R$_{14}$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{10}$ or arylalkyl;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=)NR$_{14}$R$_{14}$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;

R$_{14}$, at each occurrence, is independently selected from hydrogen, alkyl, cycloalkyl or phenyl;

m is 2; and r is 0-2.

8. The compound of claim 1, or a stereoisomer or pharmaceutically acceptable salt thereof, wherein:

Z is O;

W is

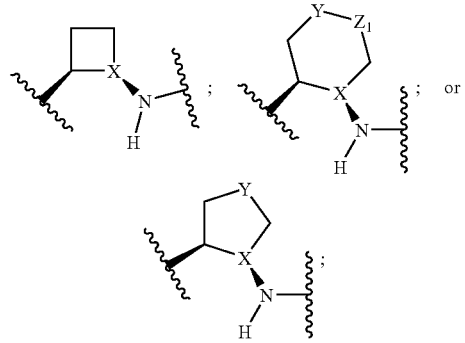

X is C(R$_8$);
Y is CH(R$_{1a}$), CH$_2$, O or S;
Z$_1$ is CH(R$_7$) or CH$_2$;
T is

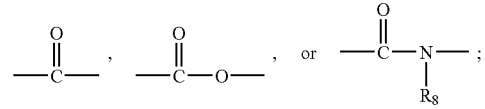

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, aryloxy, arylalkyl or arylalkyloxyalkyl;

R$_3$, at each occurrence, is independently OH or alkyl; or two R$_3$'s together with the carbon atom to which they are attached may form a 3- to 6-membered ring;

R$_4$ is F or OH;
R$_5$ is hydrogen, halo or —CN;
R$_{5a}$ is halo or —CN;
R$_{5b}$ is hydrogen, halo or —CN;
R$_6$, at each occurrence, is independently alkyl, cycloalkyl, cycloalkylalkyl, aryl, arylalkyl, heteroaryl or heteroarylalkyl;
R$_7$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 R$_{7b}$;
R$_{7b}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O)$_2$R$_6$, aryloxy, arylalkyl or arylalkyloxyalkyl;
R$_8$, at each occurrence, is independently hydrogen or alkyl;
R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;
R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O)$_2$R$_6$, —OC(=O)NR$_{14}$R$_{14}$, aryloxy or arylalkyl;
R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, aryloxy or arylalkyl;
R$_{14}$, at each occurrence, is independently selected from hydrogen, alkyl, cycloalkyl or phenyl;
m is 2; and
r is 0-2.

9. The compound of claim 1, or a stereoisomer or pharmaceutically acceptable salt thereof, wherein:
Z is O;
W is

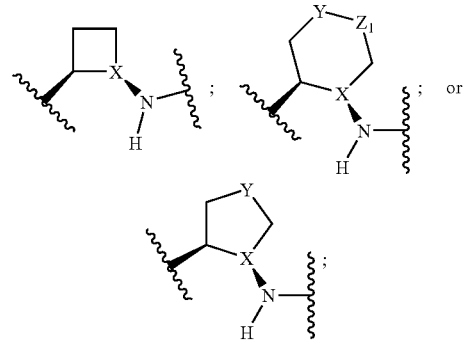

X is C(R$_8$);
Y is CH(R$_{1a}$), CH$_2$ or O;
Z$_1$ is CH(R$_7$) or CH$_2$;
T is

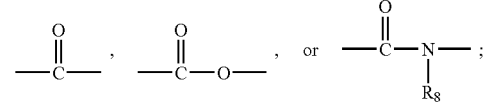

R$_1$ is alkyl, cycloalkyl, aryl, heterocyclyl or heteroaryl, all of which may be optionally substituted with 0-5 R$_{1a}$;
R$_{1a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{1b}$;

$R_{1b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C(=O)OR_6$, —S$(O)_2NR_9C(=O)NR_9R_9$, —C(=O)$NR_9S(O)_2(CF_2)_rCF_3$, —C(=O)$(CR_8R_8)_rR_{10}$, —$NR_9C(=O)H$, —$NR_9C(=O)(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C(=O)OR_6$, —$NR_9S(O_2)R_6$, aryloxy, arylalkyl or arylalkyloxyalkyl;

$R_3$, at each occurrence, is alkyl;

$R_4$ is OH;

$R_5$ is hydrogen or halo;

$R_{5a}$ is halo or —CN;

$R_{5b}$ is hydrogen or halo;

$R_6$, at each occurrence, is independently alkyl, cycloalkyl, aryl or heteroaryl;

$R_7$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C(=O)OR_6$, —S$(O)_2NR_9C(=O)NR_9R_9$, —C(=O)$NR_9S(O)_2(CF_2)_rCF_3$, —C(=O)$(CR_8R_8)_rR_{10}$, —$NR_9C(=O)H$, —$NR_9C(=O)(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C(=O)OR_6$, —$NR_9S(O_2)R_6$, =O, —OC(=O)$NR_9R_9$, aryloxy or arylalkyl, wherein the alkyl, aryl, cycloalkyl, cycloalkylalkyl, heteroaryl, heteroarylalkyl, heterocyclyl, heterocyclylalkyl, aryloxy and arylalkyl may be optionally substituted with 0-3 $R_{7b}$;

$R_{7b}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —C(=O)$NR_9R_9$, —$NR_9R_9$, —S$(O)_2NR_9R_9$, —$NR_9S(O)_2(CF_2)_rCF_3$, —C(=O)$NR_9S(O)_2R_6$, —S$(O)_2NR_9C(=O)OR_6$, —S$(O)_2NR_9C(=O)NR_9R_9$, —C(=O)$NR_9S(O)_2(CF_2)_rCF_3$, —C(=O)$(CR_8R_8)_rR_{10}$, —$NR_9C(=O)H$, —$NR_9C(=O)(CR_8R_8)_rR_{10}$, —OC(=O)$(CR_8R_8)_rR_{10}$, —S(=O)$(CR_8R_8)_rR_{10}$, —S$(O)_2(CR_8R_8)_rR_{10}$, —$NR_9C(=O)OR_6$, —$NR_9S(O_2)R_6$, aryloxy, arylalkyl or arylalkyloxyalkyl;

$R_8$, at each occurrence, is independently hydrogen or alkyl;

$R_9$, at each occurrence, is independently hydrogen, alkyl, cycloalkyl, aryl, heteroaryl or heterocyclyl, wherein the aryl, heteroaryl or heterocyclyl may be optionally substituted with 0-5 $R_{9a}$, and the heteroaryl or heterocyclyl contain 1-4 heteroatoms selected from N, O, and S;

$R_{9a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —C(=O)$NR_{14}R_{14}$, —$NR_{14}R_{14}$, —S$(O)_2NR_{14}R_{14}$, —$NR_{14}S(O)_2(CF_2)_rCF_3$, —C(=O)$NR_{14}S(O)_2R_6$, —S$(O)_2NR_{14}C(=O)OR_6$, —S$(O)_2NR_{14}C(=O)NR_{14}R_{14}$, —C(=O)$NR_{14}S(O)_2(CF_2)_rCF_3$, —C(=O)$(CR_8R_8)_rR_{14}$, —$NR_{14}C(=O)H$, —$NR_{14}C(=O)(CR_8R_8)_rR_{14}$, —OC(=O)$(CR_8R_8)_rR_{14}$, —S(=O)$(CR_8R_8)_rR_{14}$, —S$(O)_2(CR_8R_8)_rR_{14}$, —$NR_{14}C(=O)OR_6$, —$NR_{14}S(O_2)R_6$, —OC(=O)$NR_{14}R_{14}$, aryloxy or arylalkyl;

$R_{10}$, at each occurrence, is independently selected from alkyl, aryl or heterocyclyl, wherein the aryl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, cycloalkylalkyl, heteroaryl, heteroarylalkyl, heterocyclyl, heterocyclylalkyl, halo, —CN, —$NO_2$, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —C(=O)$NR_{14}R_{14}$, —$NR_{14}R_{14}$, —S$(O)_2NR_{14}R_{14}$, —$NR_{14}S(O)_2(CF_2)_rCF_3$, —C(=O)$NR_{14}S(O)_2R_6$, —S$(O)_2NR_{14}C(=O)OR_6$, —S$(O)_2NR_{14}C(=O)NR_{14}R_{14}$, —C(=O)$NR_{14}S(O)_2(CF_2)_rCF_3$, —C(=O)$(CR_8R_8)_rR_{14}$, —$NR_{14}C(=O)H$, —$NR_{14}C(=O)(CR_8R_8)_rR_{14}$, —OC(=O)$(CR_8R_8)_rR_{14}$, —S(=O)$(CR_8R_8)_rR_{14}$, —S$(O)_2(CR_8R_8)_rR_{14}$, —$NR_{14}C(=O)OR_6$, —$NR_{14}S(O_2)R_6$, —OC(=O)$NR_{14}R_{14}$, aryloxy or arylalkyl;

$R_{14}$, at each occurrence, is independently selected from hydrogen, alkyl, cycloalkyl or phenyl;

m is 2; and r is 0-2.

10. The compound of claim 1, or a stereoisomer or pharmaceutically acceptable salt thereof, wherein:

Z is O;

W is

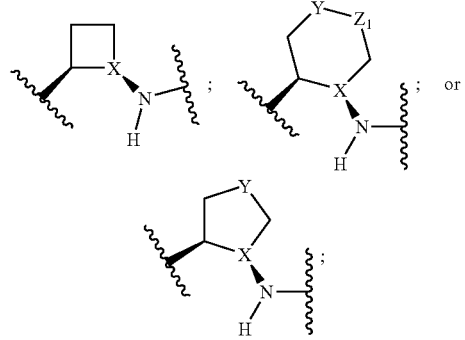

X is C($R_8$);

Y is CH($R_{1a}$) or $CH_2$;

$Z_1$ is CH($R_7$) or $CH_2$;

T is

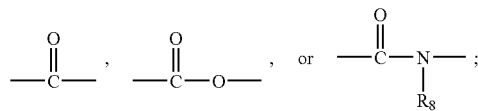

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, cycloalkyl, heteroaryl, heterocyclyl, halo, —CN, —$NO_2$, —C(=O)O$(CR_8R_8)_rR_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$, or aryloxy, wherein the alkyl, aryl, cycloalkyl, heteroaryl, heterocyclyl and aryloxy may be optionally substituted with 0-3 R$_{1b}$;

R$_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, or aryloxy;

R$_3$, at each occurrence, is alkyl;

R$_4$ is OH;

R$_5$ is hydrogen or halo;

R$_{5a}$ is halo;

R$_{5b}$ is hydrogen or halo;

R$_6$, at each occurrence, is independently alkyl, cycloalkyl, aryl or heteroaryl;

R$_7$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, =O, —OC(=O)NR$_9$R$_9$ or aryloxy, wherein the alkyl, aryl, cycloalkyl, heteroaryl, heterocyclyl and aryloxy may be optionally substituted with 0-3 R$_{7b}$;

R$_{7b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$ or aryloxy;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$ or aryloxy;

R$_{14}$, at each occurrence, is independently selected from hydrogen, alkyl, cycloalkyl or phenyl;

m is 2; and r is 0-2.

11. The compound of claim 1, or a stereoisomer or pharmaceutically acceptable salt thereof, wherein:

Z is O;

W is

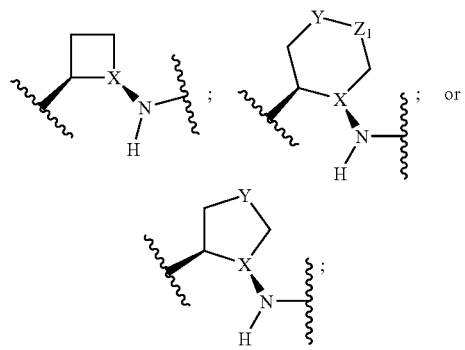

X is CH;
Y is CH$_2$;
Z$_1$ is CH$_2$;
T is

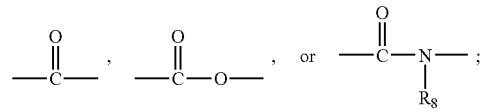

R$_1$ is alkyl, cycloalkyl, aryl or heteroaryl, all of which may be optionally substituted with 0-5 R$_{1a}$;

R$_{1a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, —OC(=O)NR$_9$R$_9$, or aryloxy, wherein the alkyl, aryl, cycloalkyl, heteroaryl, heterocyclyl and aryloxy may be optionally substituted with 0-3 R$_{1b}$;

R$_{1b}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_6$, —NR$_9$S(O$_2$)R$_6$, or aryloxy;

R$_3$, at each occurrence, is alkyl;

R$_4$ is OH;

R$_5$ is hydrogen or halo;

R$_{5a}$ is chloro;

R$_{5b}$ is hydrogen or halo;

R$_6$, at each occurrence, is independently alkyl, cycloalkyl, aryl or heteroaryl;

R$_8$, at each occurrence, is independently hydrogen or alkyl;

R$_9$, at each occurrence, is independently hydrogen, alkyl, cycloalkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S;

R$_{9a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$, or aryloxy;

R$_{10}$, at each occurrence, is independently selected from alkyl, aryl or heterocyclyl, wherein the aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heteroaryl, heterocyclyl, halo, —CN, —NO$_2$, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_6$, —NR$_{14}$S(O$_2$)R$_6$, —OC(=O)NR$_{14}$R$_{14}$ or aryloxy;

R$_{14}$, at each occurrence, is independently selected from hydrogen, alkyl, cycloalkyl or phenyl;

m is 2; and r is 0-2.

12. A pharmaceutical composition comprised of a pharmaceutically acceptable carrier and a therapeutically effective amount of a compound of claim 1.

13. The compound of claim 1, or a stereoisomer or pharmaceutically acceptable salt thereof, wherein the compound is selected from the group consisting of:

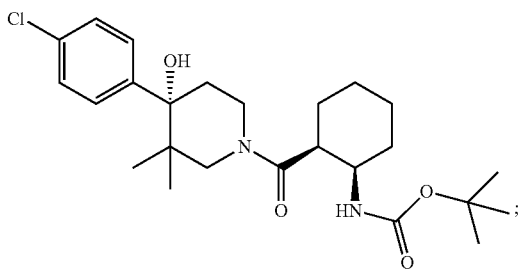

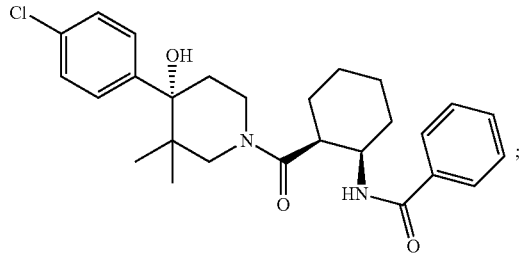

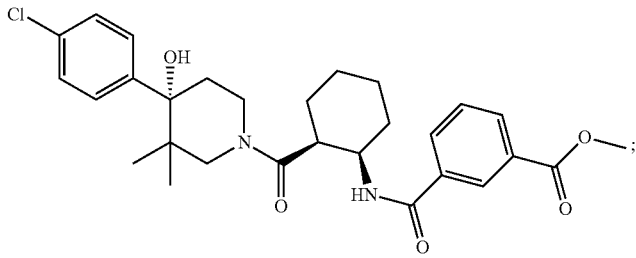

-continued
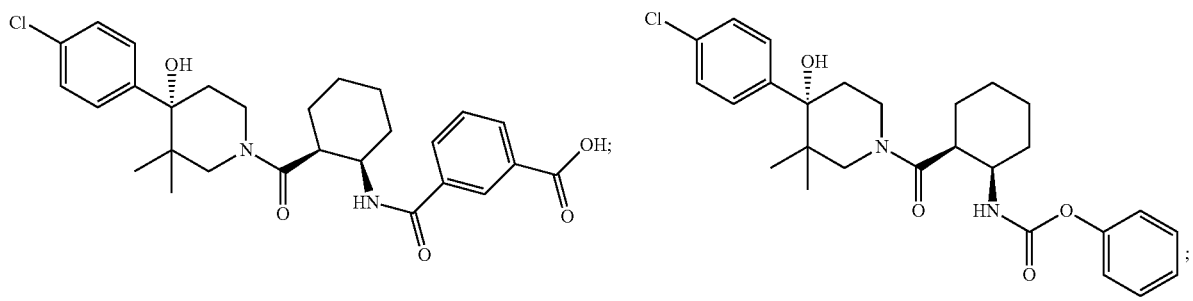
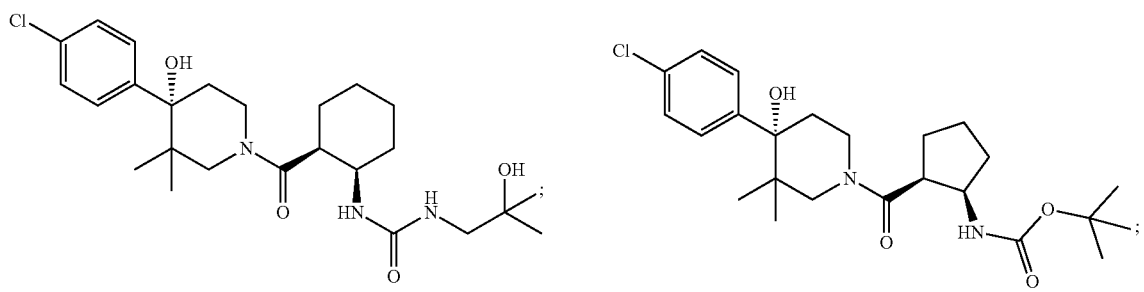
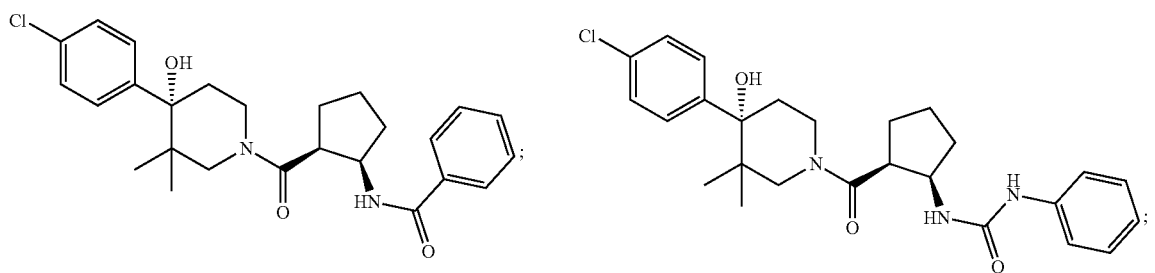
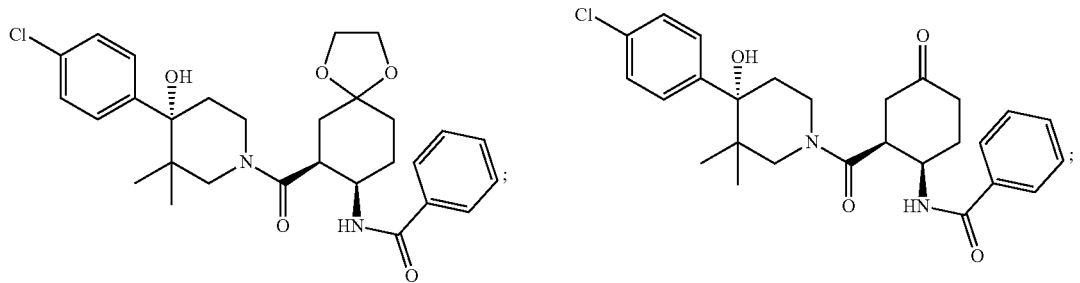
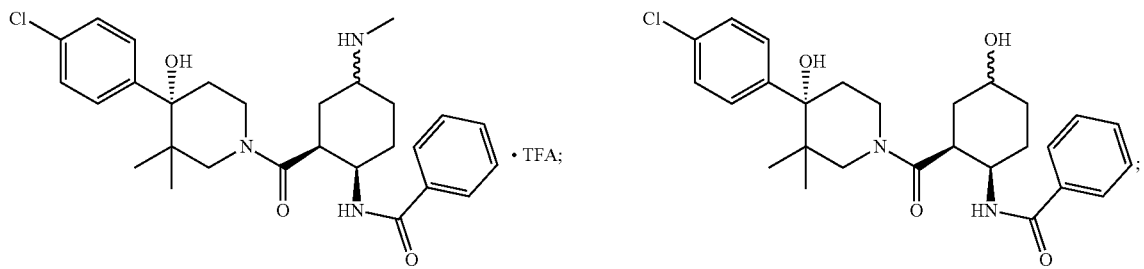

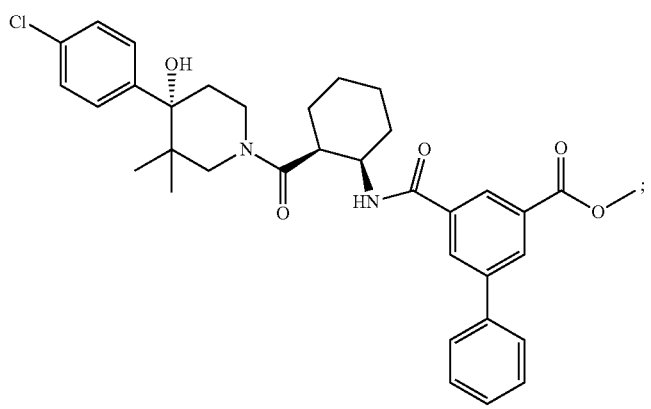
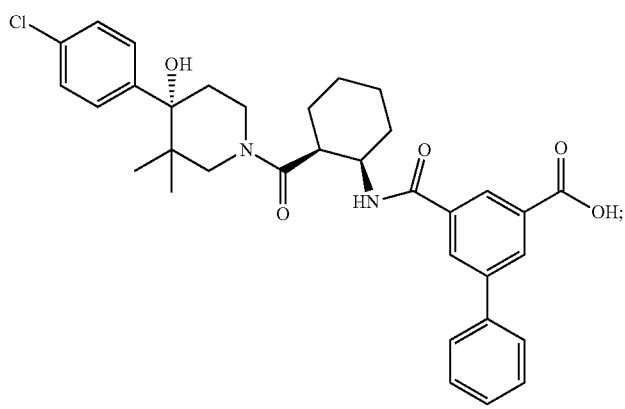
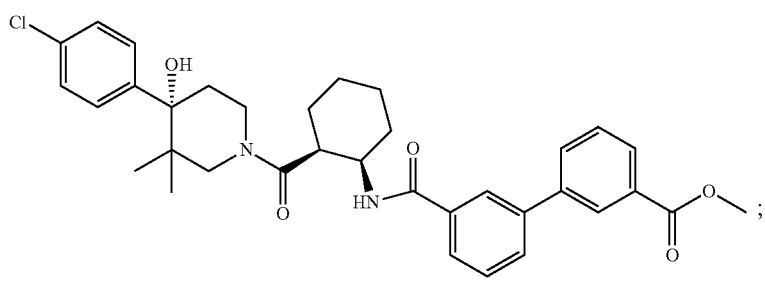
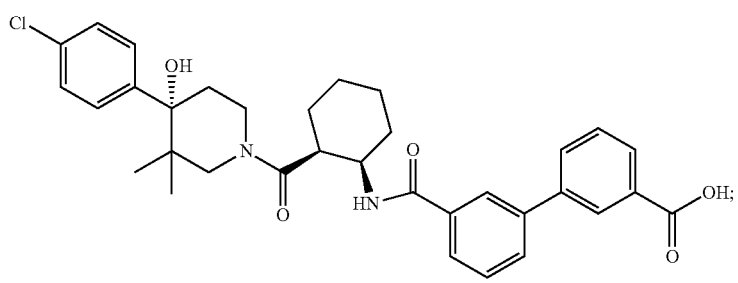
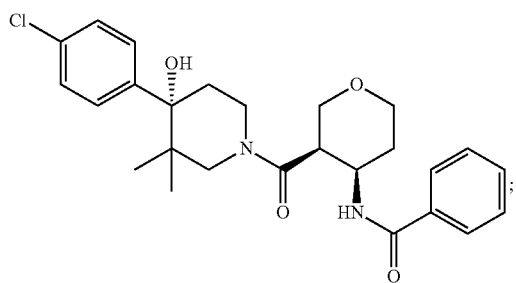
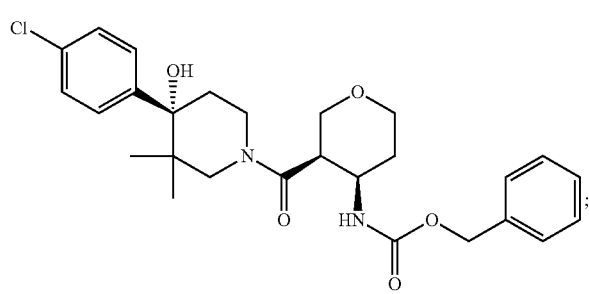

-continued
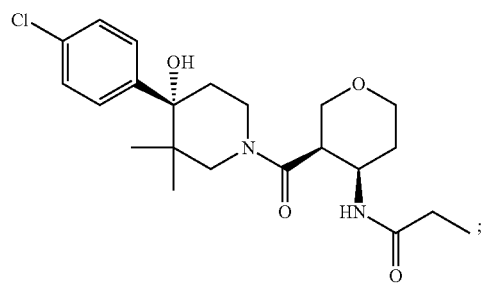
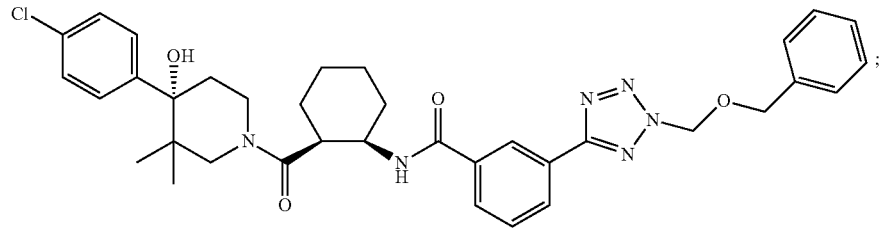
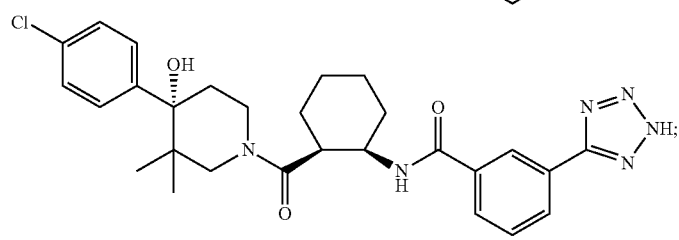
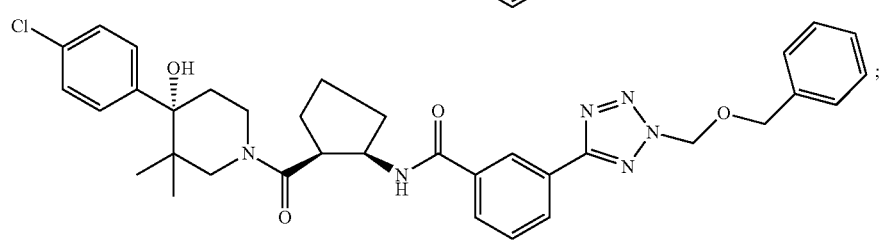
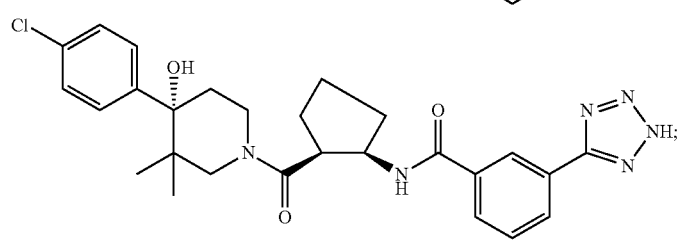
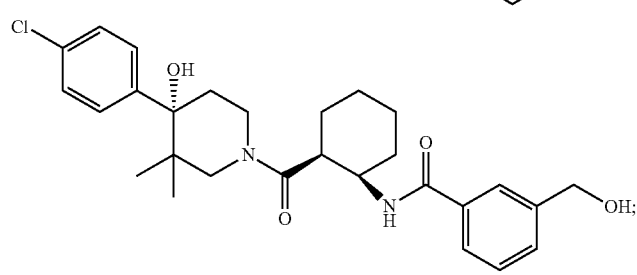
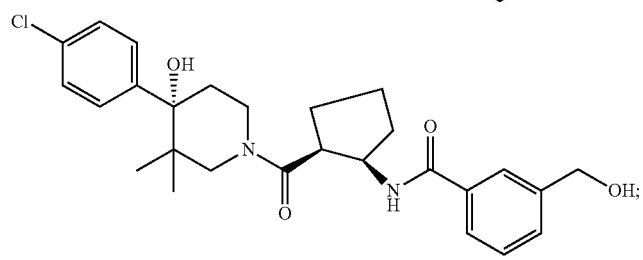

167 168
-continued
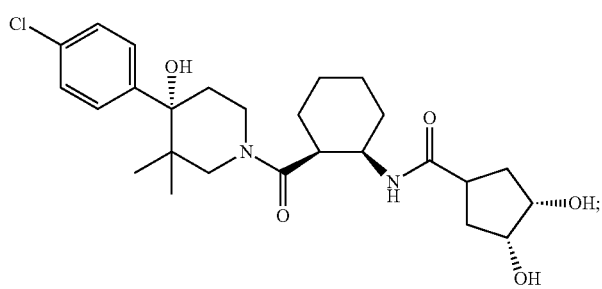
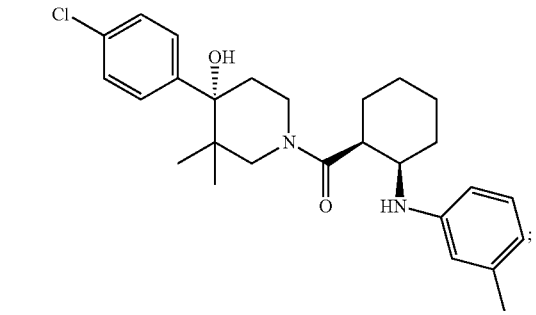
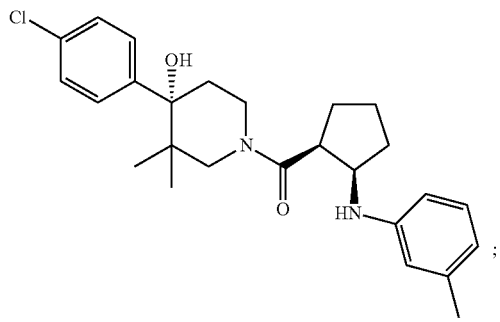
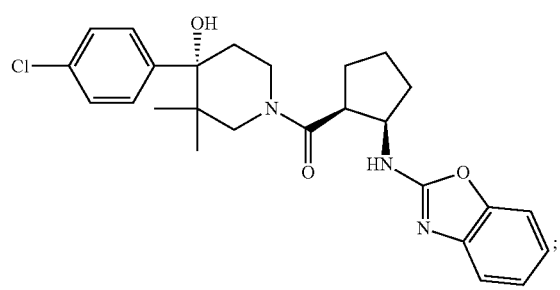
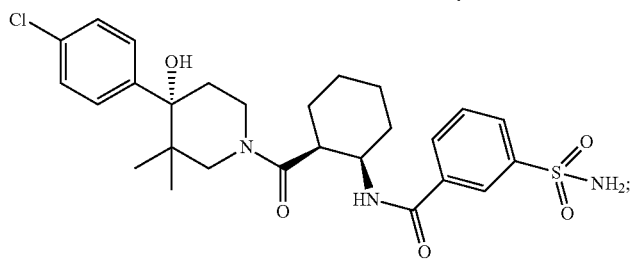
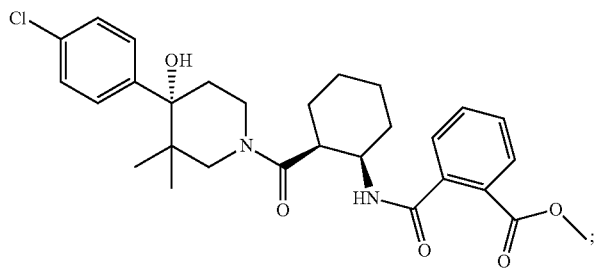
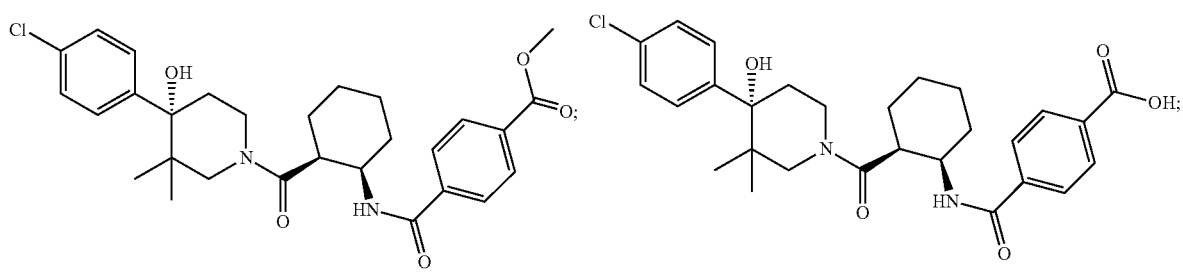
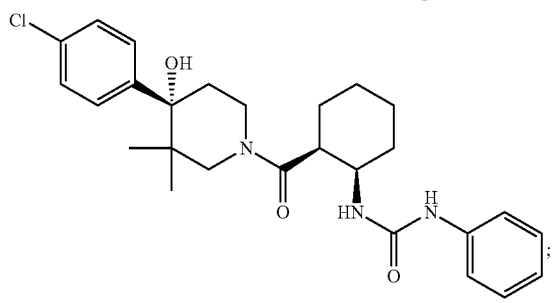

169 170
-continued
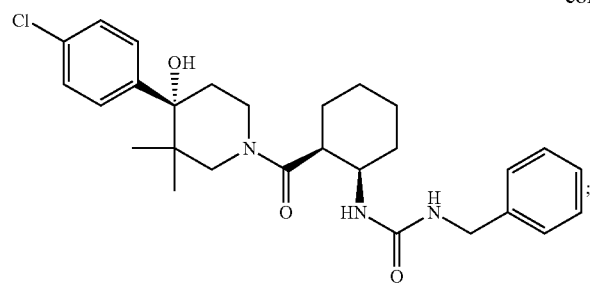
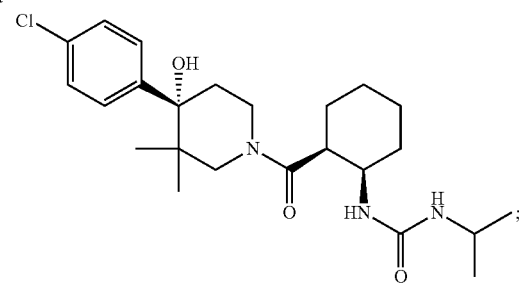
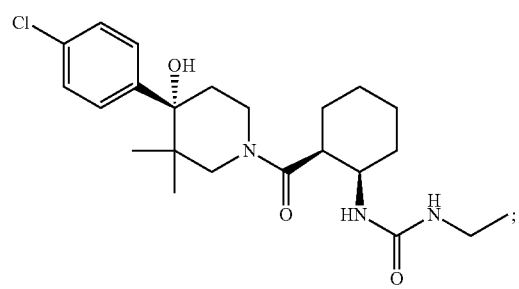
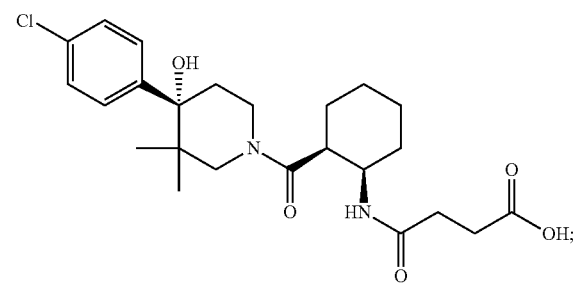
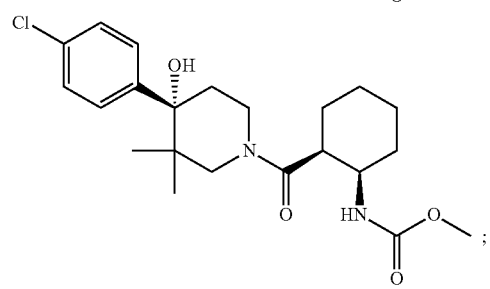
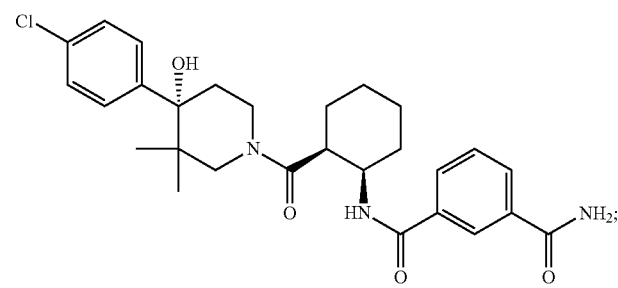
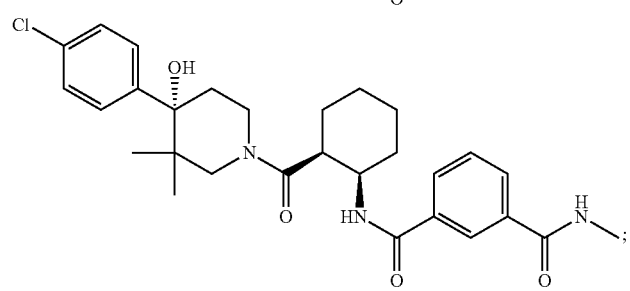
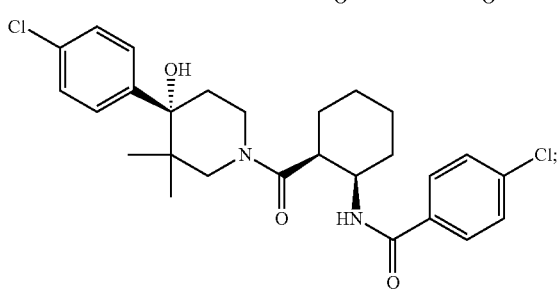
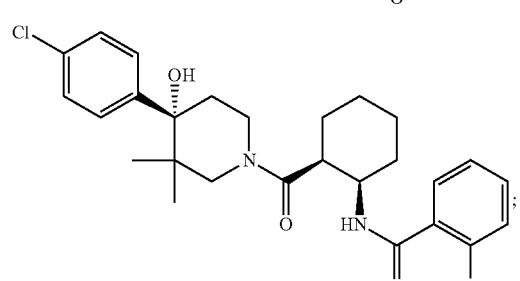
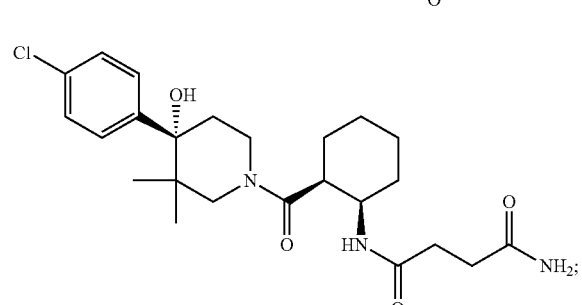
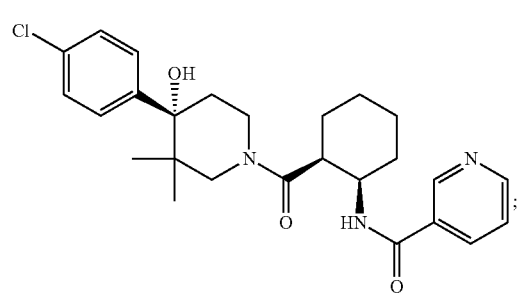
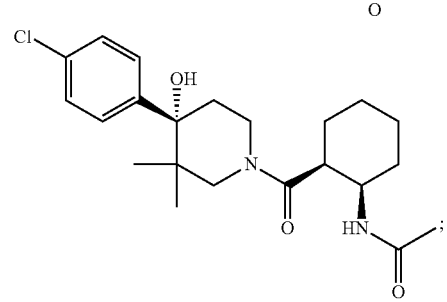

171
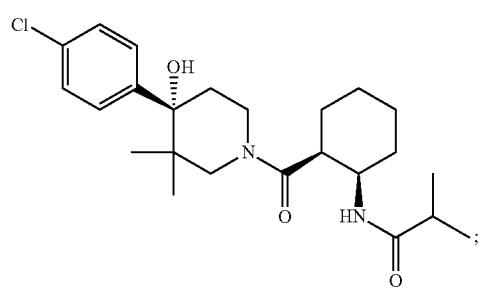
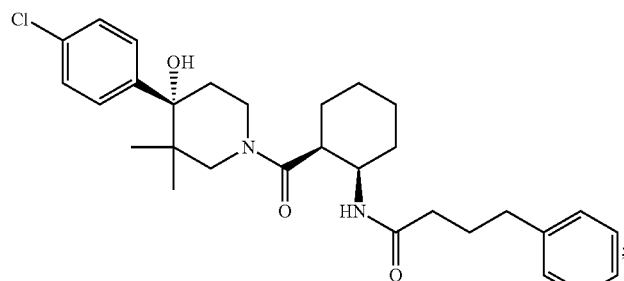
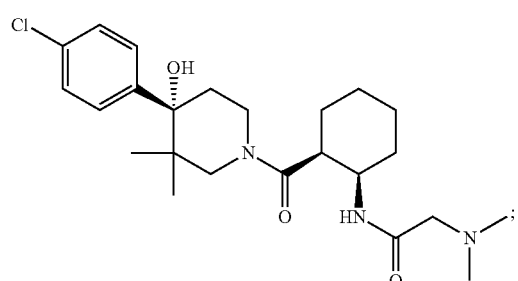
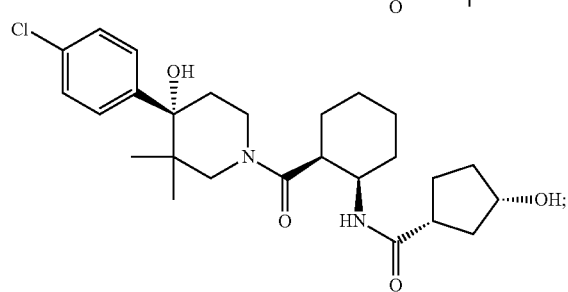
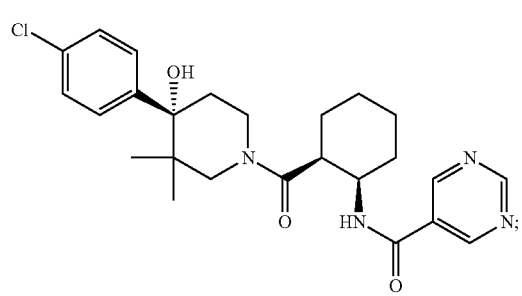
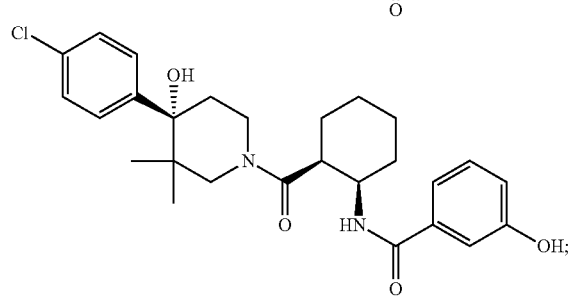
172
-continued
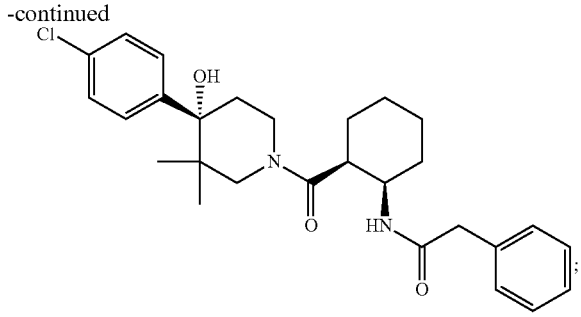
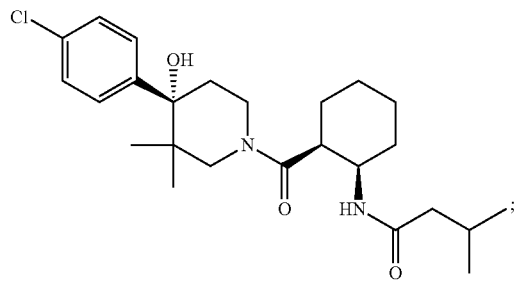
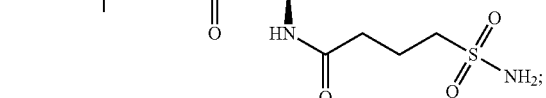
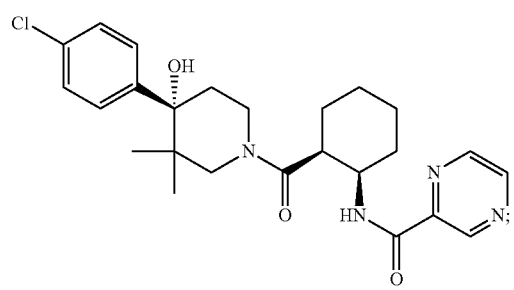
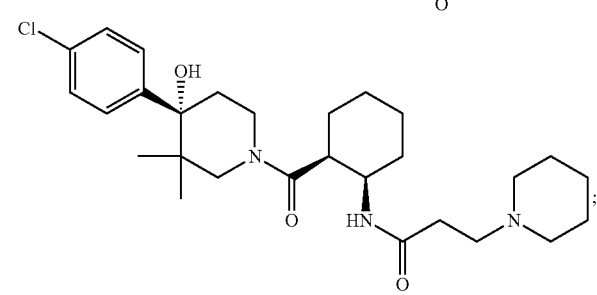
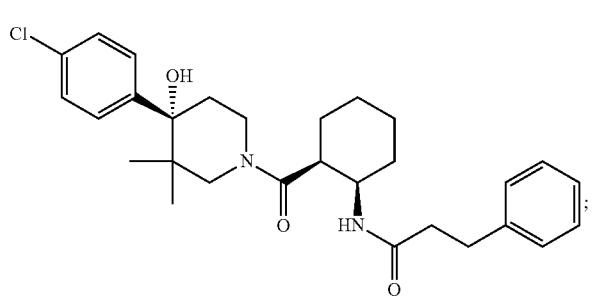

173                                              174
                                         -continued
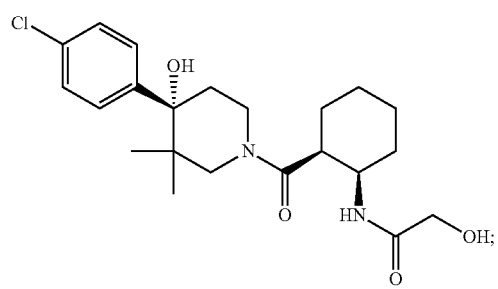
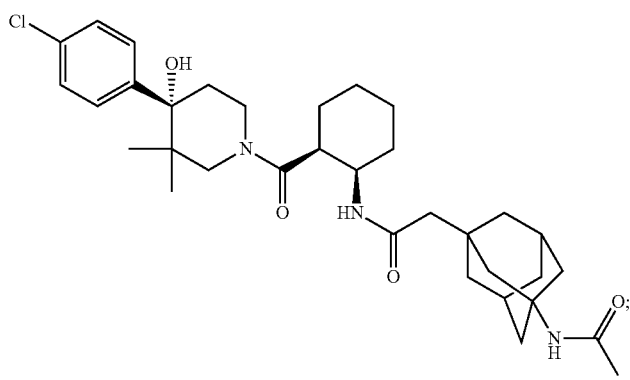
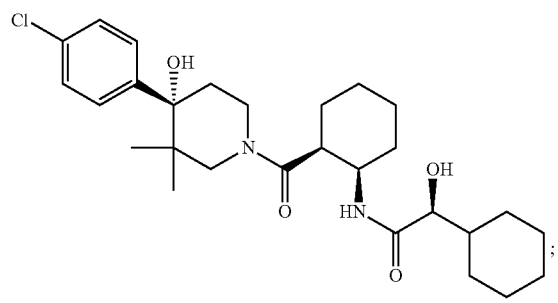
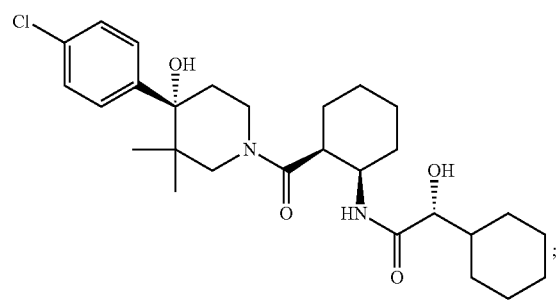
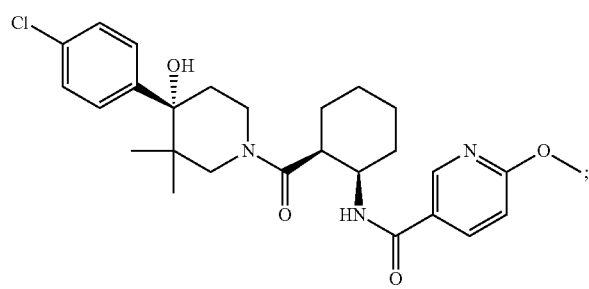
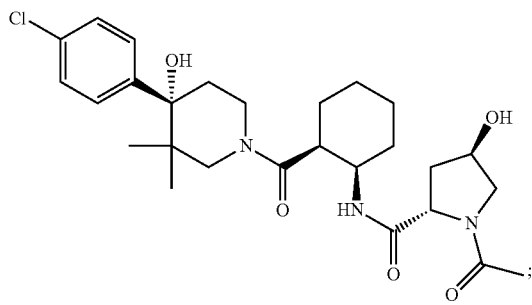
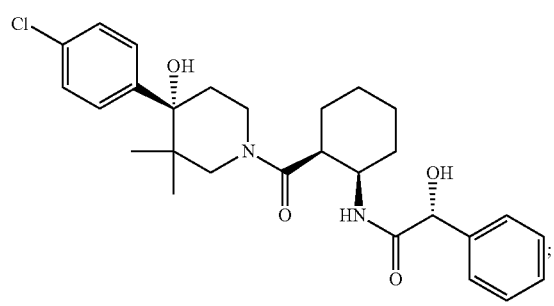
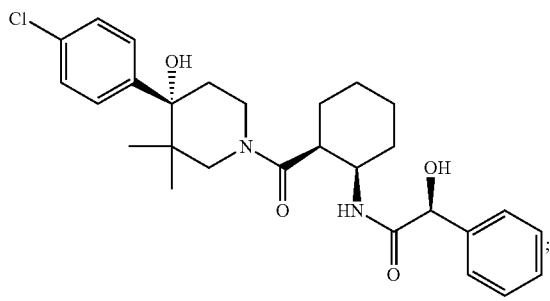
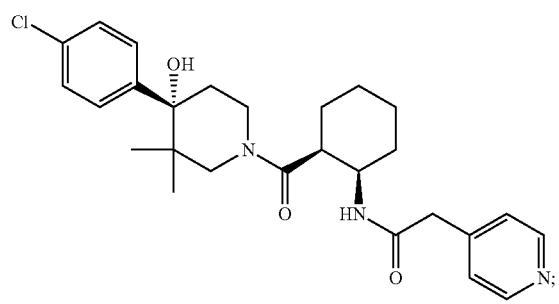
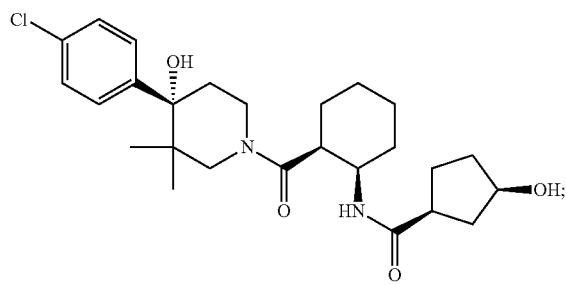

-continued
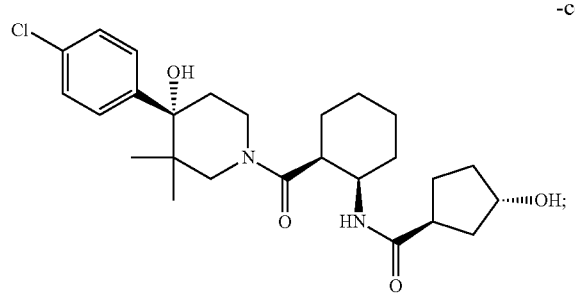
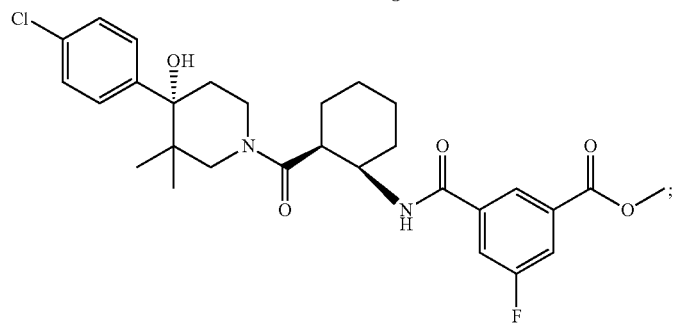
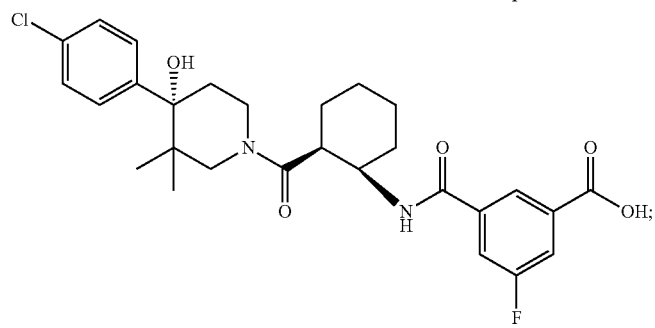
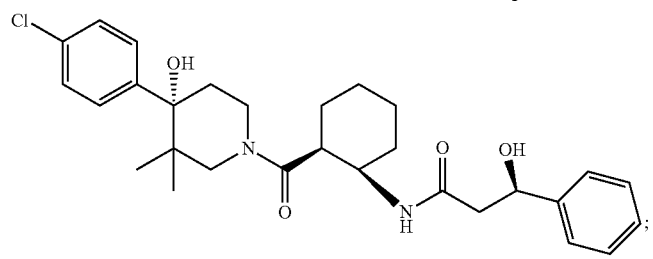
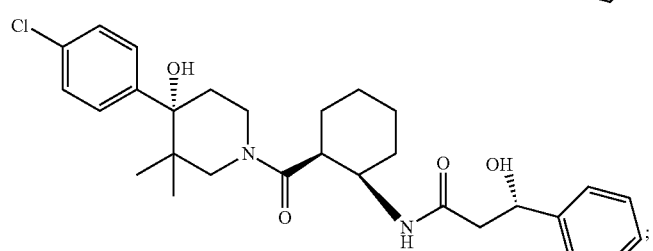
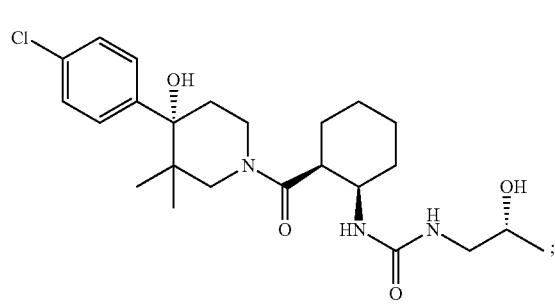
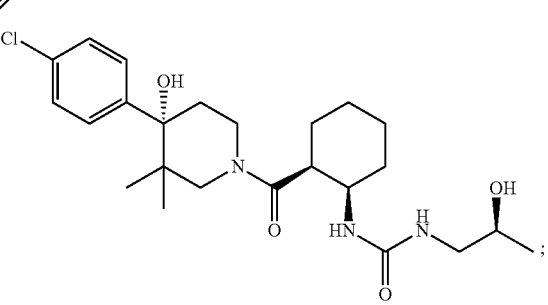

177
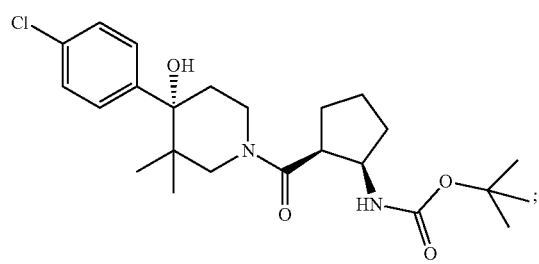
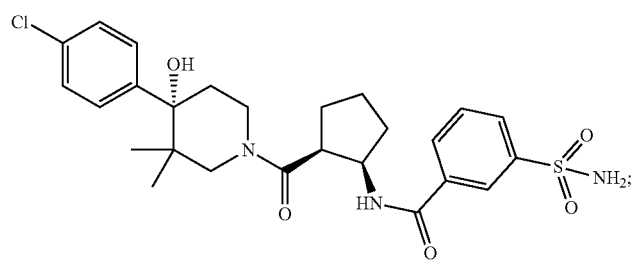
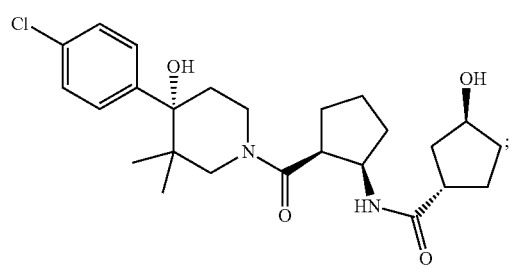
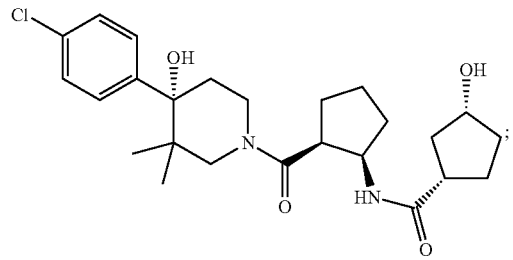
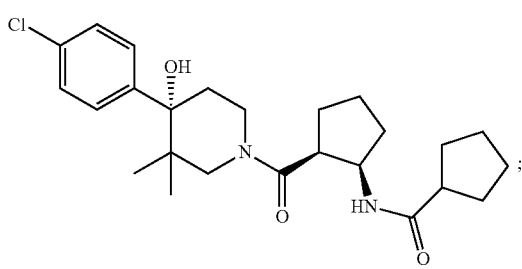
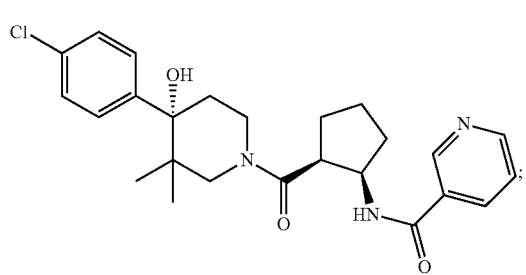
178
-continued
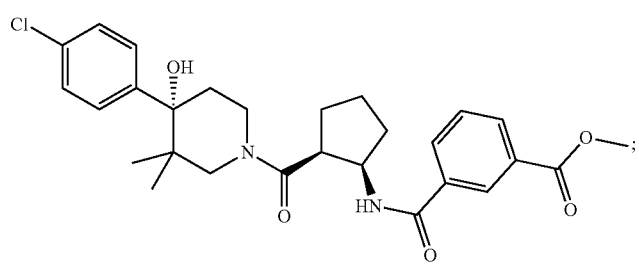
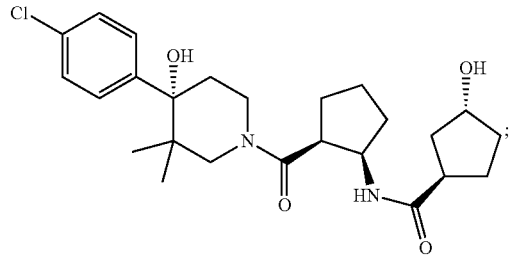
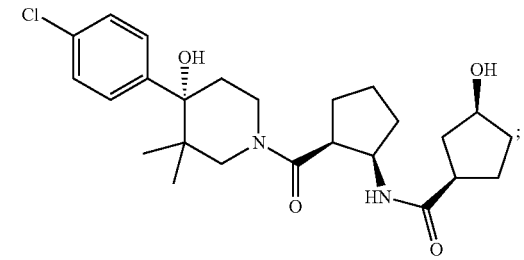
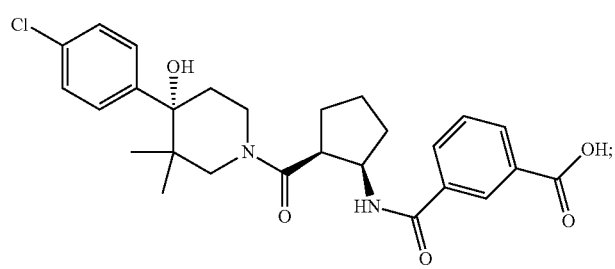
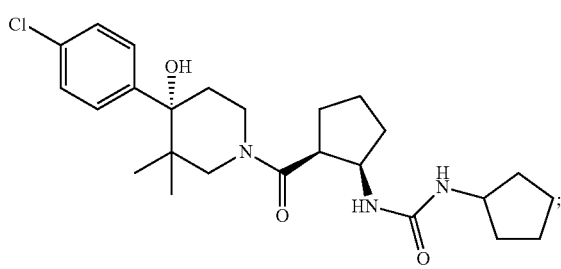

-continued
179
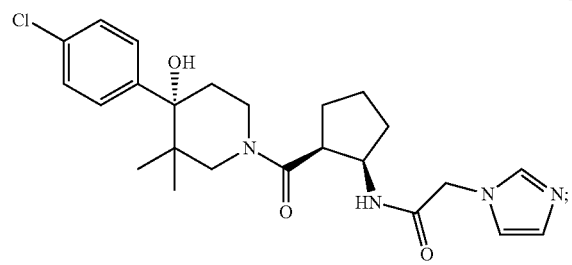
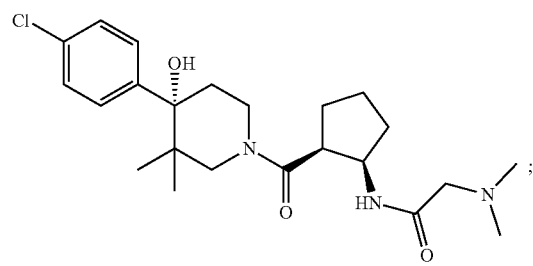
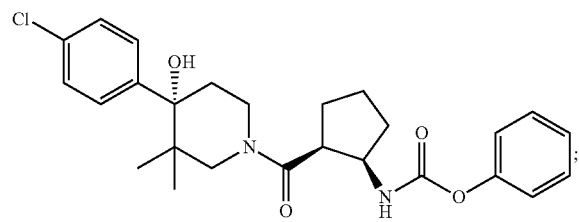
180
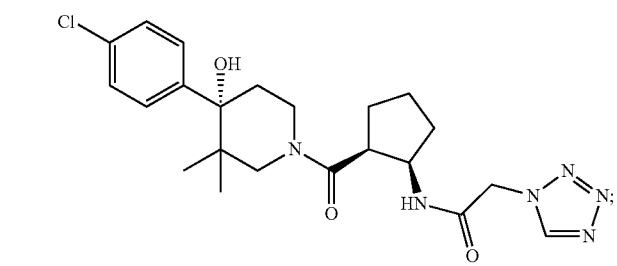
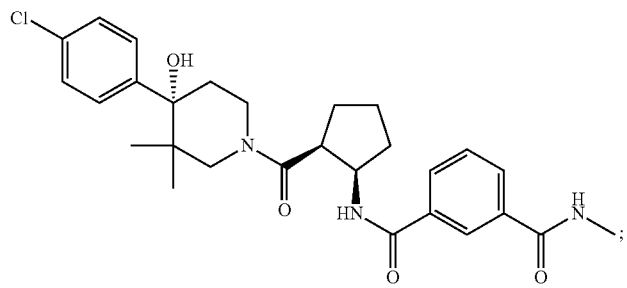
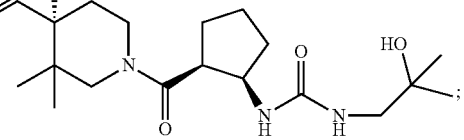
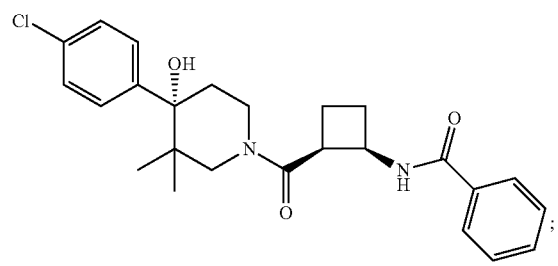
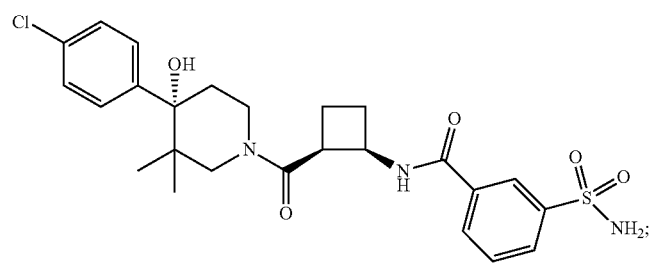
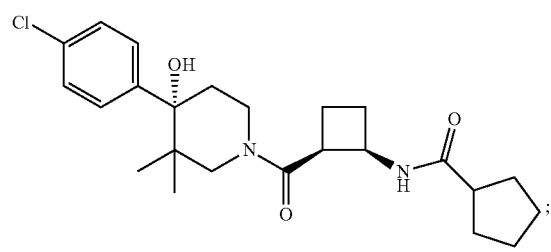
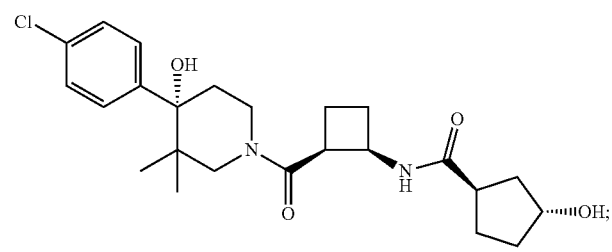

-continued
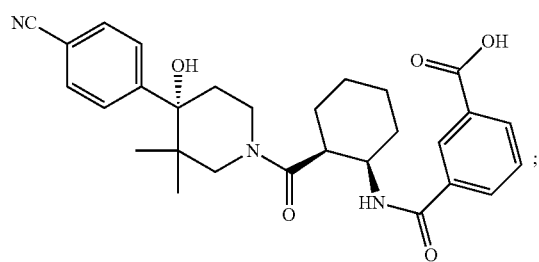
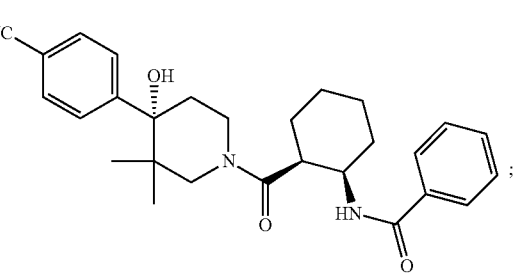
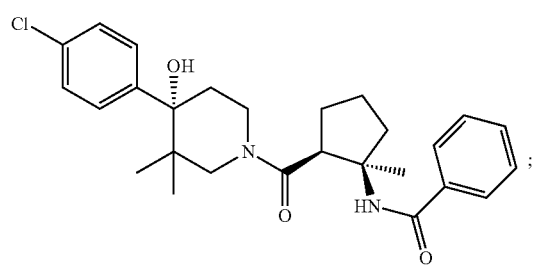
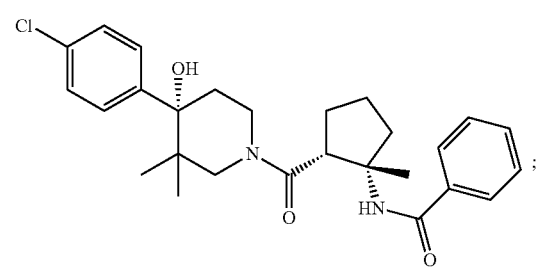
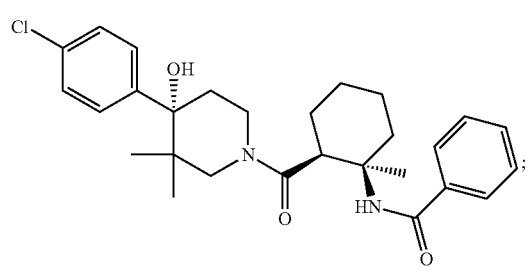
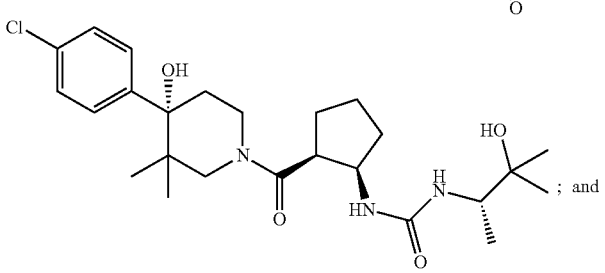
; and
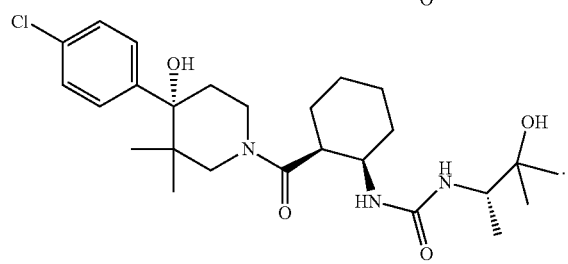
14. A pharmaceutical composition comprised of a pharmaceutically acceptable carrier and a therapeutically effective amount of a compound of claim 13.
* * * * *

UNITED STATES PATENT AND TRADEMARK OFFICE
CERTIFICATE OF CORRECTION

PATENT NO. : 8,536,198 B2
APPLICATION NO. : 12/670025
DATED : September 17, 2013
INVENTOR(S) : Joseph B. Santella et al.

It is certified that error appears in the above-identified patent and that said Letters Patent is hereby corrected as shown below:

On the Title Page:

Item (73), Assignee:
  Change "Priceton, NJ (US)" to -- Princeton, NJ (US) --.

In the Claims:

Claim 13:
  Column 164, structure at end of column, change

"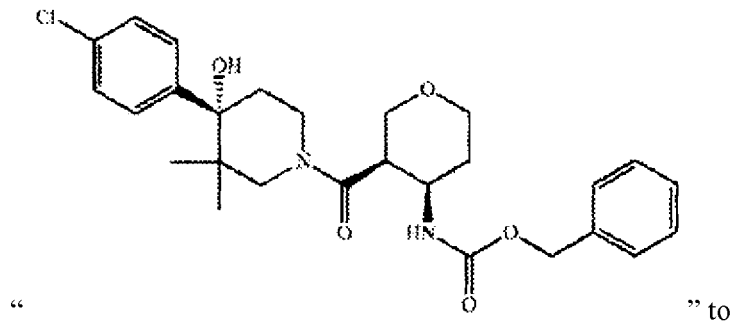" to

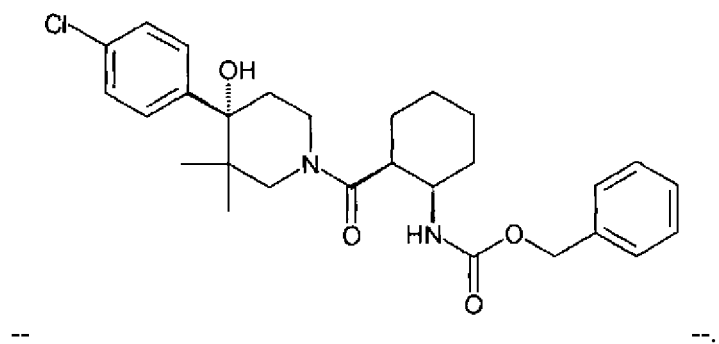

--.

CERTIFICATE OF CORRECTION (continued)

In the Claims:

Claim 13 (continued):

Column 165, first structure, change